(12) United States Patent
Beechem et al.

(10) Patent No.: US 11,708,602 B2
(45) Date of Patent: *Jul. 25, 2023

(54) SIMULTANEOUS QUANTIFICATION OF GENE EXPRESSION IN A USER-DEFINED REGION OF A CROSS-SECTIONED TISSUE

(71) Applicants: NanoString Technologies, Inc., Seattle, WA (US); Board of Regents, The University of Texas System, Austin, TX (US)

(72) Inventors: Joseph M. Beechem, Eugene, OR (US); Charles Warren, Bremerton, WA (US); Chris Merritt, Seattle, WA (US); Jaemyeong Jung, Bellevue, WA (US); Dwayne L. Dunaway, Seattle, WA (US); Scott Crowder, Seattle, WA (US); Kristina Sorg, Seattle, WA (US); Gordon B. Mills, Houston, TX (US)

(73) Assignees: NanoString Technologies, Inc., Seattle, WA (US); Board of Regents, The University of Texas System, Austin, TX (US)

( * ) Notice: Subject to any disclaimer, the term of this patent is extended or adjusted under 35 U.S.C. 154(b) by 766 days.

This patent is subject to a terminal disclaimer.

(21) Appl. No.: 16/596,596

(22) Filed: Oct. 8, 2019

(65) Prior Publication Data
US 2020/0040385 A1 Feb. 6, 2020

Related U.S. Application Data

(63) Continuation of application No. 15/211,230, filed on Jul. 15, 2016, now Pat. No. 10,640,816.

(60) Provisional application No. 62/323,023, filed on Apr. 15, 2016, provisional application No. 62/277,289, filed on Jan. 11, 2016, provisional application No. 62/261,657, filed on Dec. 1, 2015, provisional application No. 62/193,809, filed on Jul. 17, 2015.

(51) Int. Cl.
*C12Q 1/68* (2018.01)
*C12Q 1/6841* (2018.01)
*G01N 33/68* (2006.01)
*C12Q 1/6823* (2018.01)

(52) U.S. Cl.
CPC ......... *C12Q 1/6841* (2013.01); *C12Q 1/6823* (2013.01); *G01N 33/6845* (2013.01)

(58) Field of Classification Search
CPC . C12Q 1/6841; C12Q 1/6823; G01N 33/6845
See application file for complete search history.

(56) References Cited

U.S. PATENT DOCUMENTS

| | | |
|---|---|---|
| 5,320,814 A | 6/1994 | Walt et al. |
| 5,543,838 A | 8/1996 | Hosier et al. |
| 5,635,352 A | 6/1997 | Urdea et al. |
| 6,100,030 A | 8/2000 | McCasky Feazel et al. |
| 6,207,392 B1 | 3/2001 | Weiss et al. |
| 6,429,027 B1 | 8/2002 | Chee et al. |
| 6,596,257 B2 | 7/2003 | Bryan |
| 6,602,661 B1 | 8/2003 | Knezevic et al. |
| 6,690,470 B1 | 2/2004 | Baer et al. |
| 6,942,968 B1 | 9/2005 | Dickinson et al. |
| 7,060,507 B2 | 6/2006 | Akeson et al. |
| 7,132,519 B2 | 11/2006 | Monforte et al. |
| 7,214,477 B1 | 5/2007 | Emmert-Buck |
| 7,255,999 B2 | 8/2007 | Singh et al. |
| 7,402,399 B2 | 7/2008 | Mukherjeei et al. |
| 7,569,392 B2 | 8/2009 | Levy et al. |
| 7,648,828 B2 | 1/2010 | Chan-Hui et al. |
| 7,728,287 B2 | 6/2010 | Felton et al. |
| 8,003,312 B2 | 8/2011 | Krutzik et al. |
| 8,221,972 B2 | 7/2012 | Lemaire et al. |
| 8,309,306 B2 | 11/2012 | Nolan et al. |
| 8,349,574 B2 | 1/2013 | Bates et al. |
| 8,362,415 B2 | 1/2013 | Felton et al. |
| 8,486,623 B2 | 7/2013 | Monforte et al. |
| 8,637,650 B2 | 1/2014 | Cherkasov et al. |
| 8,753,824 B2 | 6/2014 | Papin et al. |
| 8,865,414 B2 | 10/2014 | Hennig et al. |
| 8,906,700 B2 | 12/2014 | Lim et al. |
| 9,046,477 B2 | 6/2015 | Emedcoles et al. |
| 9,228,948 B2 | 1/2016 | Emedcoles et al. |
| 9,297,762 B2 | 3/2016 | Emedcoles et al. |
| 9,304,084 B2 | 4/2016 | Emedcoles et al. |
| 9,376,677 B2 | 6/2016 | Mir |
| 9,376,678 B2 | 6/2016 | Gormley et al. |

(Continued)

FOREIGN PATENT DOCUMENTS

| | | |
|---|---|---|
| JP | 2008-542783 A | 11/2008 |
| WO | WO 97/07245 A1 | 2/1997 |

(Continued)

OTHER PUBLICATIONS

Agasti, S. S. et al., "Photocleavable DNA Barcode—Antibody Conjugates Allow Sensitive and Multiplexed Protein Analysis in Single Cells," J. Am. Chem. Soc., 134:18499-18502 (2012).

(Continued)

*Primary Examiner* — Kenneth R Horlick

(74) *Attorney, Agent, or Firm* — Cooley LLP; Ivor R. Elrifi; Matthew Pavao

(57) ABSTRACT

The present invention relates to, among other things, probes, compositions, methods, and kits for simultaneous, multiplexed detection and quantification of protein and/or nucleic acid expression in a user-defined region of a tissue, user-defined cell, and/or user-defined subcellular structure within a cell.

20 Claims, 59 Drawing Sheets

(58 of 59 Drawing Sheet(s) Filed in Color)

(56) References Cited

U.S. PATENT DOCUMENTS

| | | |
|---|---|---|
| 9,644,204 B2 | 5/2017 | Hindson et al. |
| 9,975,122 B2 | 5/2018 | Masquelier et al. |
| 10,053,723 B2 | 8/2018 | Hindson et al. |
| 10,071,377 B2 | 9/2018 | Bharadwaj et al. |
| 10,501,777 B2 | 12/2019 | Beechem et al. |
| 10,640,816 B2 | 5/2020 | Beechem et al. |
| 11,377,689 B2 | 7/2022 | Beechem et al. |
| 2001/0002315 A1 | 5/2001 | Schultz et al. |
| 2001/0007775 A1 | 7/2001 | Seul et al. |
| 2001/0023078 A1 | 9/2001 | Bawendi et al. |
| 2001/0029049 A1 | 10/2001 | Walt et al. |
| 2001/0034034 A1 | 10/2001 | Bruchez et al. |
| 2001/0053334 A1 | 12/2001 | Chen et al. |
| 2002/0028457 A1 | 3/2002 | Empedocles et al. |
| 2002/0034737 A1 | 3/2002 | Drmanac |
| 2002/0034827 A1 | 3/2002 | Singh et al. |
| 2002/0039728 A1 | 4/2002 | Kain et al. |
| 2002/0051971 A1 | 5/2002 | Stuelpnagel et al. |
| 2002/0068018 A1 | 6/2002 | Pepper et al. |
| 2002/0177141 A1 | 11/2002 | Chee et al. |
| 2002/0187515 A1 | 12/2002 | Chee et al. |
| 2003/0008323 A1 | 1/2003 | Ravkin et al. |
| 2003/0013091 A1 | 1/2003 | Dimitrov |
| 2003/0028981 A1 | 2/2003 | Chandler et al. |
| 2003/0148335 A1 | 8/2003 | Shen et al. |
| 2003/0152952 A1 | 8/2003 | Van Ness et al. |
| 2003/0186426 A1 | 10/2003 | Brewer et al. |
| 2004/0000519 A1 | 1/2004 | Yong et al. |
| 2005/0048498 A1 | 3/2005 | Woudenberg et al. |
| 2005/0131006 A1 | 6/2005 | Mukherjee et al. |
| 2005/0170439 A1 | 8/2005 | Chan-Hui et al. |
| 2005/0196786 A1 | 9/2005 | Levy |
| 2005/0233318 A1 | 10/2005 | Chee et al. |
| 2006/0063196 A1 | 3/2006 | Akeson et al. |
| 2007/0166708 A1 | 7/2007 | Dimitrov et al. |
| 2008/0038725 A1 | 2/2008 | Luo et al. |
| 2008/0038734 A1 | 2/2008 | Sorge et al. |
| 2008/0118934 A1 | 5/2008 | Gerdes et al. |
| 2010/0015607 A1 | 1/2010 | Geiss et al. |
| 2010/0047924 A1 | 2/2010 | Webster et al. |
| 2010/0075858 A1 | 3/2010 | Davis et al. |
| 2010/0112710 A1 | 5/2010 | Geiss et al. |
| 2010/0151472 A1 | 6/2010 | Nolan et al. |
| 2010/0178650 A1 | 7/2010 | Karsten et al. |
| 2010/0209913 A1 | 8/2010 | Endress et al. |
| 2010/0261026 A1 | 10/2010 | Ferree et al. |
| 2010/0262374 A1 | 10/2010 | Hwang et al. |
| 2011/0086774 A1 | 4/2011 | Dunaway et al. |
| 2011/0151451 A1 | 6/2011 | Lemaire et al. |
| 2011/0172115 A1 | 7/2011 | Thompson |
| 2011/0223613 A1 | 9/2011 | Gut |
| 2011/0245111 A1 | 10/2011 | Chee |
| 2013/0023433 A1 | 1/2013 | Luo et al. |
| 2013/0178372 A1 | 7/2013 | Geiss et al. |
| 2014/0120532 A1 | 5/2014 | Lee et al. |
| 2014/0120550 A1 | 5/2014 | Baranov |
| 2014/0121117 A1 | 5/2014 | Tanner |
| 2014/0371088 A1 | 12/2014 | Webster |
| 2015/0080233 A1 | 3/2015 | Bendall et al. |
| 2015/0099650 A1 | 4/2015 | Sood et al. |
| 2015/0132763 A1 | 5/2015 | Amorese et al. |
| 2015/0141297 A1 | 5/2015 | Lim et al. |
| 2015/0287578 A1 | 10/2015 | Bendall et al. |
| 2015/0329852 A1 | 11/2015 | Nolan |
| 2015/0368697 A1 | 12/2015 | Samusik et al. |
| 2016/0194701 A1 | 7/2016 | Beechem et al. |
| 2016/0362730 A1 | 12/2016 | Alexander et al. |
| 2017/0016053 A1 | 1/2017 | Beechem et al. |
| 2017/0016909 A1 | 1/2017 | Beechem et al. |
| 2017/0275669 A1 | 9/2017 | Weissleder et al. |
| 2018/0142286 A1 | 5/2018 | Dunaway et al. |
| 2019/0249248 A1 | 8/2019 | Beechem et al. |
| 2020/0040382 A1 | 2/2020 | Beechem et al. |
| 2021/0403998 A1 | 12/2021 | Beechem et al. |
| 2021/0403999 A1 | 12/2021 | Beechem et al. |
| 2022/0220555 A1 | 7/2022 | Beechem et al. |

FOREIGN PATENT DOCUMENTS

| | | |
|---|---|---|
| WO | WO 97/14028 A2 | 4/1997 |
| WO | WO 99/18434 A1 | 4/1999 |
| WO | WO 00/73777 A1 | 12/2000 |
| WO | WO 01/00875 A2 | 1/2001 |
| WO | WO 2007/000669 A2 | 1/2007 |
| WO | WO 2009/156725 A1 | 12/2009 |
| WO | WO 2010/081114 A2 | 7/2010 |
| WO | WO 2012/106385 A2 | 8/2012 |
| WO | WO 2012/140224 A1 | 10/2012 |
| WO | WO 2013/122996 A1 | 8/2013 |
| WO | WO 2014/060483 A1 | 4/2014 |
| WO | WO 2014/200767 A1 | 12/2014 |
| WO | WO 2015/128272 A2 | 9/2015 |
| WO | WO 2016/162309 A1 | 10/2016 |
| WO | WO 2017/015099 A1 | 1/2017 |
| WO | WO-2018026873 A1 | 2/2018 |
| WO | WO 2018/091676 A1 | 5/2018 |

OTHER PUBLICATIONS

Alfano, R. R. et al., "Optical Sensing, Imaging, and Manipulation for Biological and Biomedical Applications," SPIE—The International Society for Optical Engineering, Jul. 2000, vol. 4082, Taiwan, 342 pages.

Angelo, M. et al., "Multiplexed ion beam imaging of human breast tumors," Nature Medicine, 20(4):436-442 (2014).

Cesano, A. et al., "Abstract 1371: Spatially-resolved, multiplexed digital characterizatio nof protein distribution and abundance in FFPE tissue sections," AACR 107th Annual Meeting, Apr. 16-20, 2016, 5 pages.

Chow, S. et al., "Measurement of MAP Kinase Activation by Flow Cytometry Using Phospho-Specific Antibodies to MEK and ERK: Potential for Pharmacodynamic Monitoring of Signal Transduction Inhibitors," Cytometry (Communications in Clinical Cytometry), 46:72-78 (2001).

Crossetto, N. et al., "Spatially resolved transcriptomics and beyond," Nature Reviews Genetics, 16:57-66 (2015).

Dierck, K. et al., "Quantitative multiplexed profiling of cellular signaling networks using phosphotyrosine-specific DNA-tagged SH2 domains," Nature Methods, 3:737-744 (2006).

"Digital spatial profiling platform allows for spatially-resolved, high-plex quantification of mRNA distribution and abundance on FFPE and fresh frozen tissue sections," Poster #3434, Power Point Presentation, AACR Annual Meeting, Apr. 14-18, 2018, 1 page.

Drummond, E. S. et al., "Proteomic analysis of neurons microdissected from formalinfixed, paraffin-embedded Alzheimer's disease brain tissue," Scientific Reports, 5:15456 (2015), 8 pages. doi: 10.1038/srep15456.

Ferguson, J. A. et al., "High-Density Fiber-Optic DNA Random Microsphere Array," Analytical Chemistry, 72(22):5618-5624 (2000).

Frei, A. P. et al., "Highly multiplexed simultaneous detection of RNAs and proteins in single cells," Nature Methods, 13:269-275 (2016).

Geiss, G. K. et al., "Direct multiplexed measurement of gene expression with color-coded probe pairs," Nature Biotechnology, 26(3):317-326 (2008).

Gullberg, M. et al., "Cytokine detection by antibody-based proximity ligation," PNAS, 101(22):8420-8424 (2004).

Lind, K. & Kubista, M., "Development and evaluation of three real-time immuno-PCR assemblages for quantification of PSA," Journal of Immunological Methods, 304:107-116 (2005).

Steemers, F. J. et al., "Screening unlabeled DNA targets with randomly ordered fiber-optic gene arrays," Nature Biotechnology, 18:91-94 (2000).

Thiery-Lavenant, G. et al., "Targeted Multiplex Imaging Mass Spectrometry in Transmission Geometry for Subcellular Spatial Resolution," Journal of the American Society for Mass Spectrometry, 24:609-614 (2013).

(56) References Cited

OTHER PUBLICATIONS

Ullal, A. V. et al., "Cancer cell profiling by barcoding allows multiplexed protein analysis in fine needle aspirates," Science Translational Medicine, 6(219):219ra9 (2014), 22 pages, doi: 10.1126/scitranslmed.3007361.
Werner, J. H. et al., Current status of DNA sequencing by single molecule detection, Proc. SPIE 3602, Advances in Fluorescence Sensing Technology IV, pp. 355-366 (1999).
Zinchuk, V. et al., "Quantitative Colocalization Analysis of Multicolor Confocal Immunofluorescence Microscopy Images: Pushing Pixels to Explore Biological Phenomena," The Japan Society of Histochemistry and Cytochemistry, 40(4):101-111 (2007).
Zollinger, D. et al., "Abstract 3434: Digital spatial profiling platform allows for spatially resolved, high-plex quantification of mRNA distribution and abundance on FFPE and fresh frozen tissue sections," AACR Annual Meeting, Apr. 14-18, 2018, 2 pages.
"Membrane permeability," last updated Jul. 9, 2020, https://phys.libretexts.org/Courses/University_of_California_Davis/UCD%3A_Biophysics_241_-_Membrane_Biology/04%3A_Membrane-Protein_Interactions/4.01%3A_Membrane_Permeability; 5 pages.
Armani, M. et al., "2D-PCR: a method of mapping DNA in tissue sections," Lab Chip., 9(24):3526-3534 (2009); doi:10.1039/b910807f.
Bailey, R. C. et al., "DNA-Encoded Antibody Libraries: A Unified Platform for Multiplexed Cell Sorting and Detection of Genes and Proteins," J. Am. Chem. Soc., 129:1959-1967 (2007).
Lee, H. et al., "Colour-barcoded magnetic microparticles for multiplexed bioassays," Nature Materials, 9:745-749 (2010).
Lemaire, R. et al., "Tag-Mass: Specific Molecular Imaging of Transcriptome and Proteome by Mass Spectrometry Based on Photocleavable Tag," J Proteome Res., 6(6):2057-2067 (2007); doi:10.1021/pr0700044.
Dictionary Definition of "Abundance." Printed on Sep. 22, 2021, 1 page.
Large Molecules Cross Membranes via Vesicles, printed on Jan. 10, 2022, 1 page; https://www.macmillanhighered.com/BrainHoney/Resource/6716/digital_first_content/trunk/test/hillis2e/hillis2e_ch05_5.html#:~:text=Macromolecules%20such%20as%20proteins%2C%20polysaccharides,these%20macromolecules%20in%20specific%20locations.
"Strategies for Detecting mRNA Northern blotting, Nuclease Protection Assays, In Situ hybridization, and RT-PCR," ThermoFisher Scientific. Printed on Sep. 22, 2021, 2 pages.

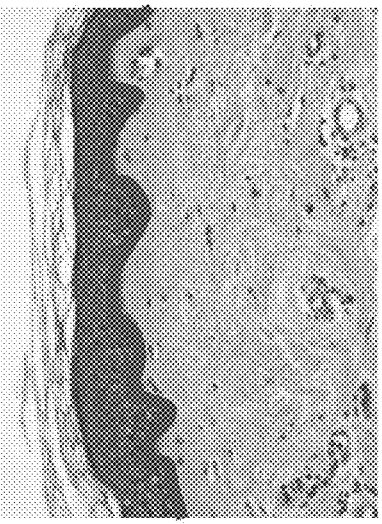
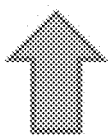
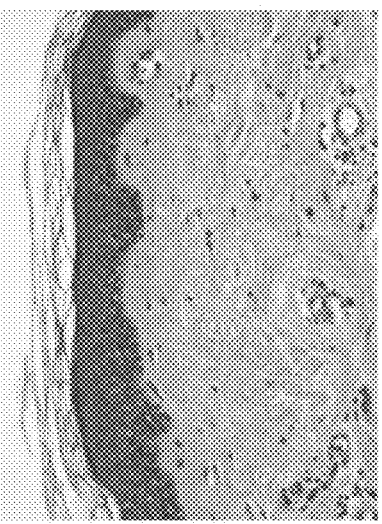
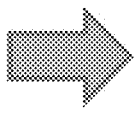
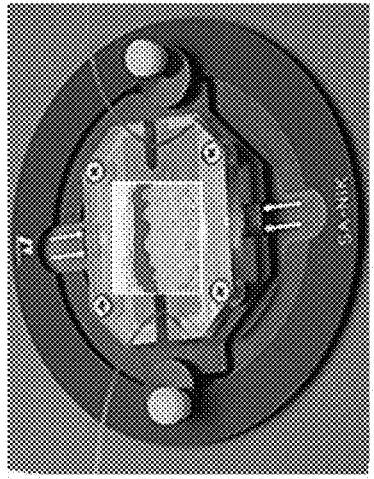
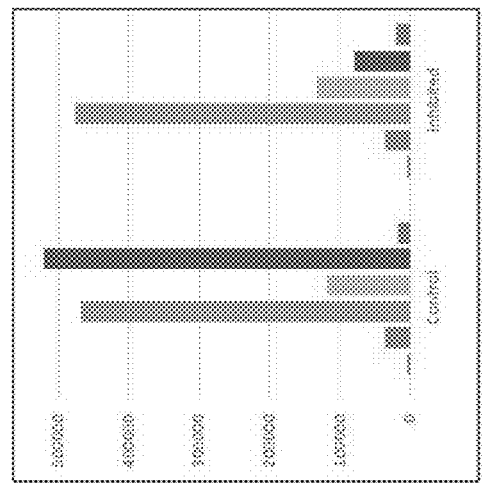
FIG. 10

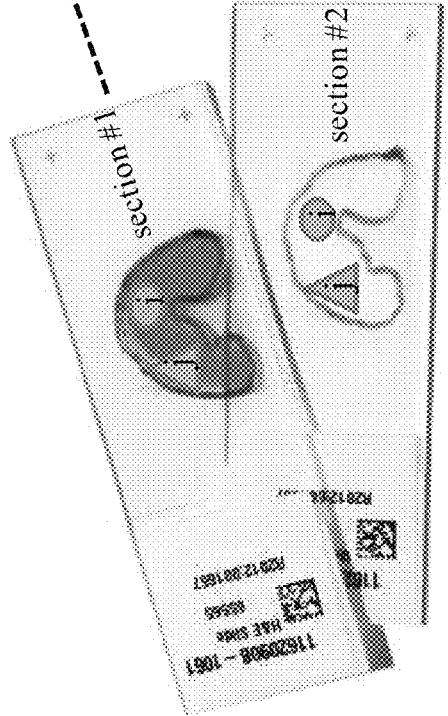

FIG. 11

Full "macroscopic feature" imaging of serial section #1 to establish region-of-interest ($ROI_i$): 

Contact section #2 with multiplexed probe composition containing probes having releasable signal oligonucleotides. Provide force to the $ROI_i$, thereby releasing only signal oligonucleotides from probes bound to nucleic acids and/or protein in $ROI_i$.

Collect signal oligonucleotides released from $ROI_i$ into small volume (~5 to 30 μL).

Repeat for $ROI_j$ up to $ROI_n$

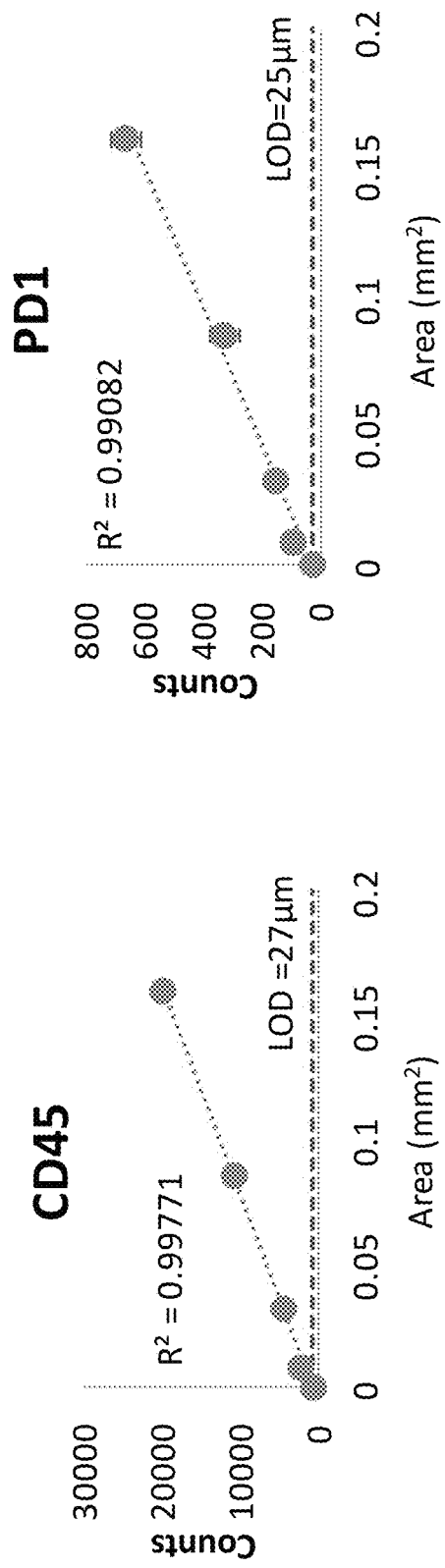

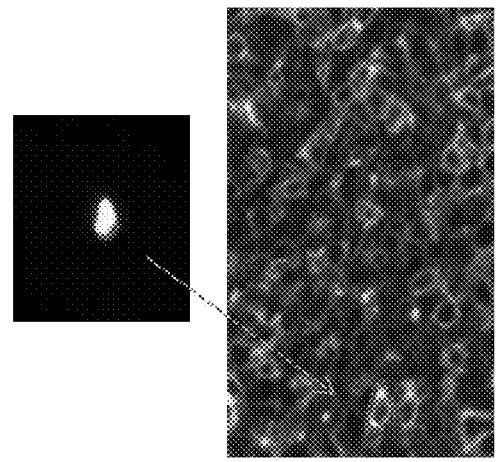
FIG. 31D
FIG. 31C
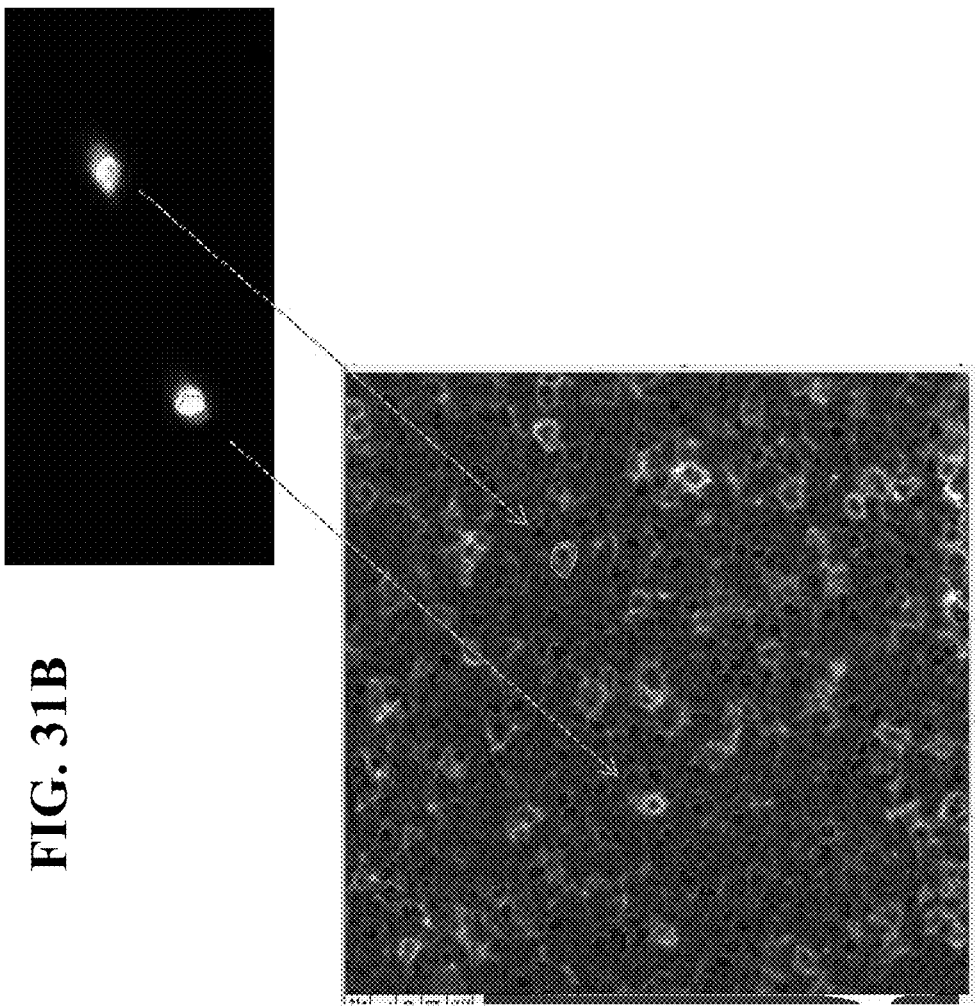
FIG. 31B
FIG. 31A

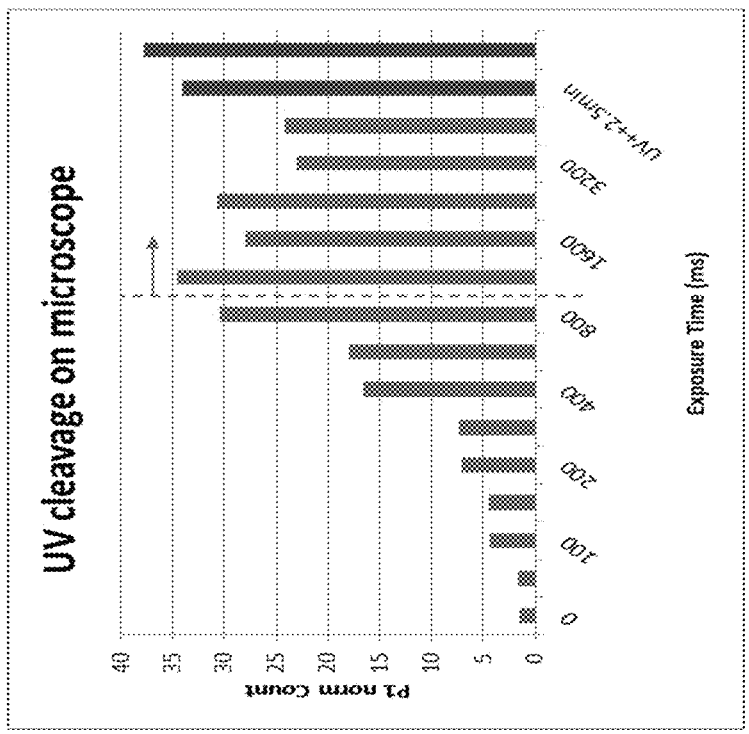
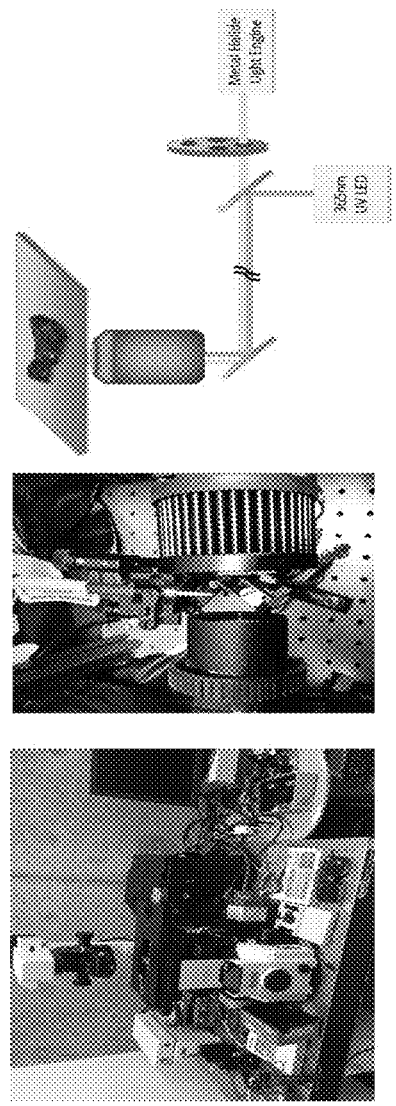
FIG. 35

FIG. 39
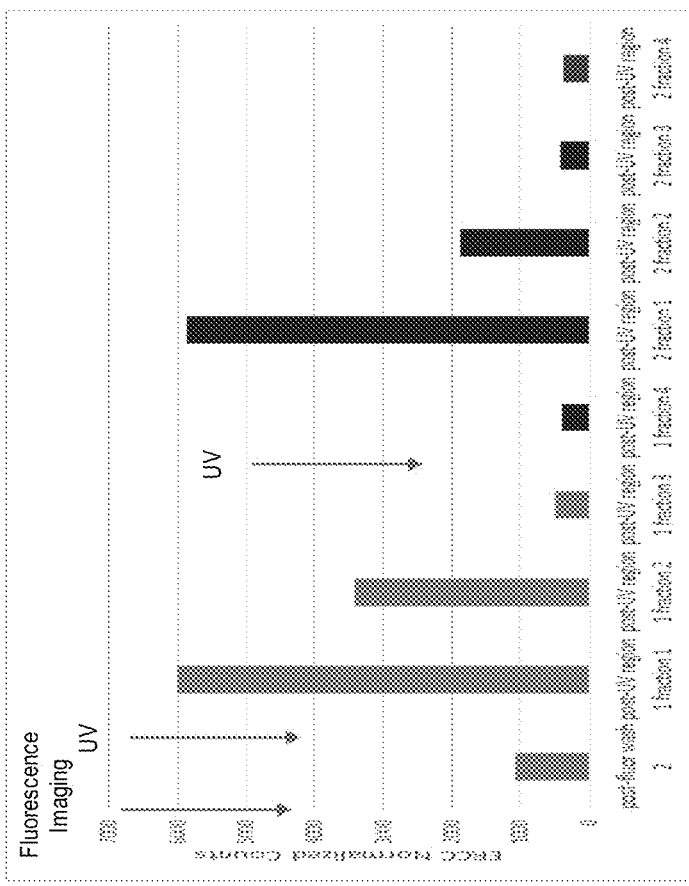
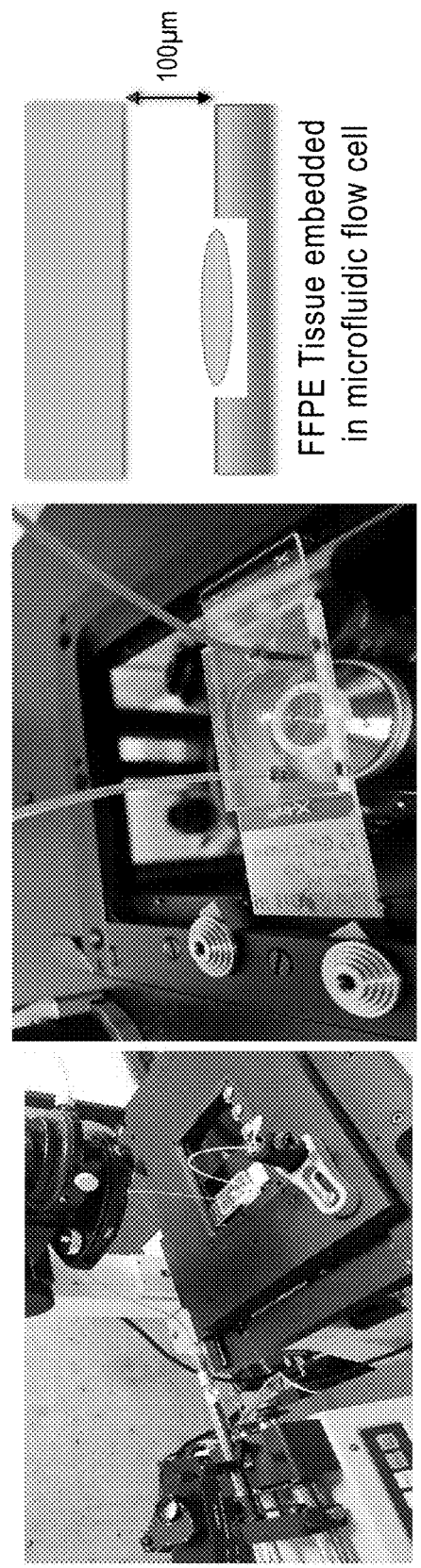

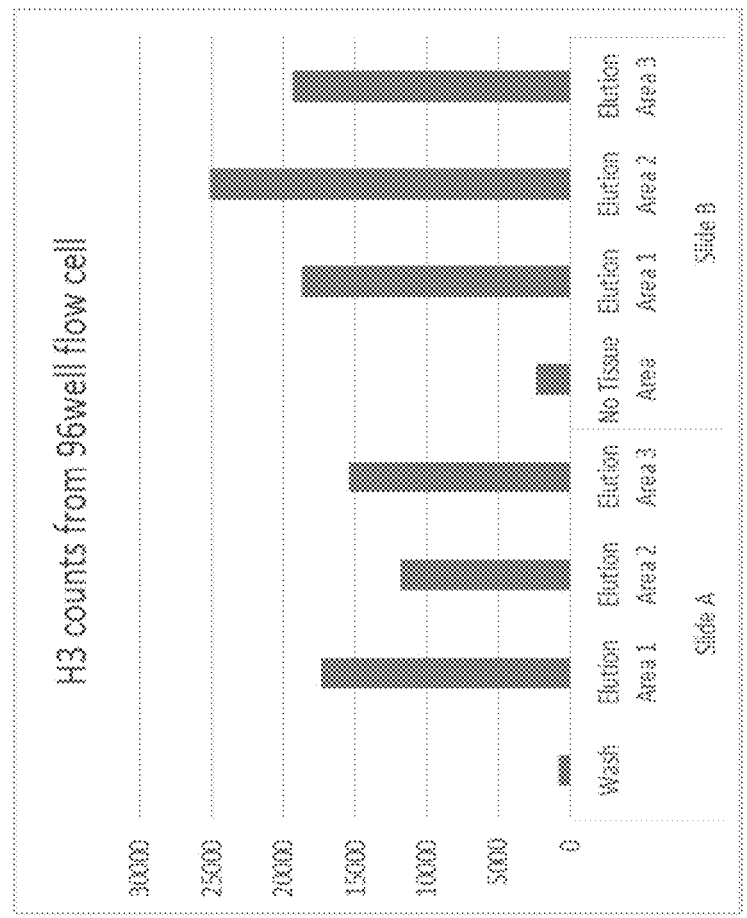
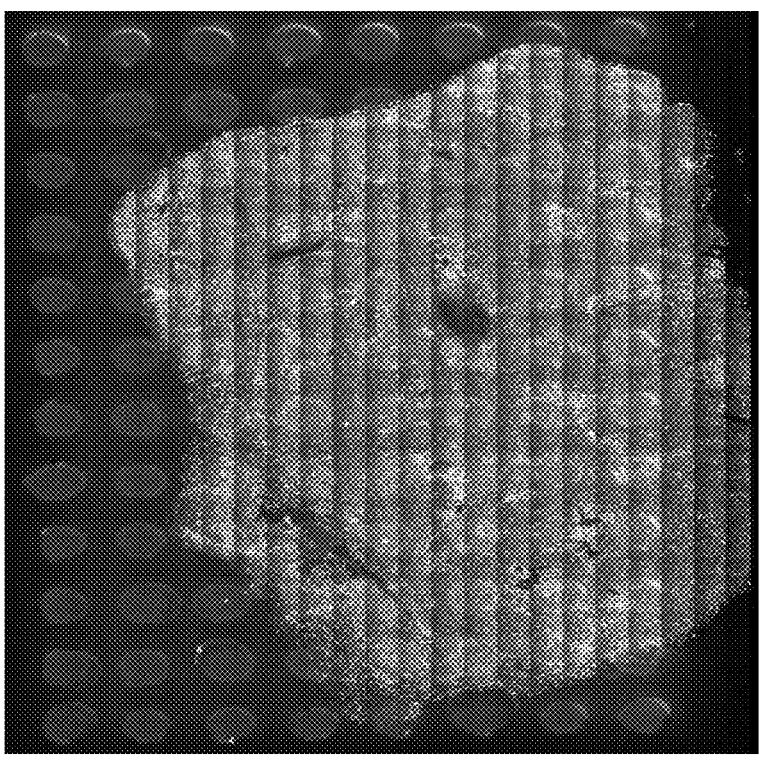
FIG. 42B
96-hole format

FIG. 47
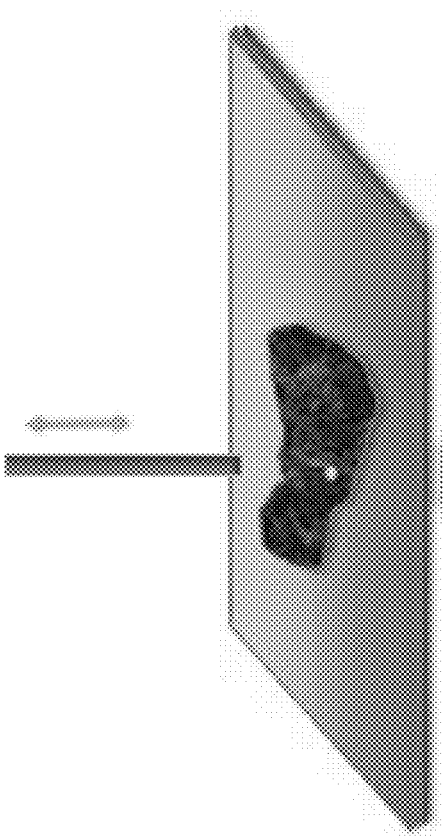
Single tube/pipet (fixed position)
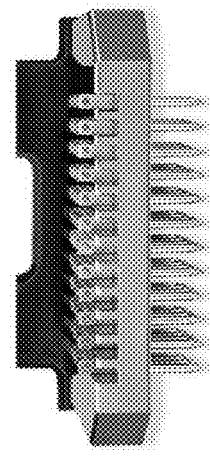
Microtube array
Products - Microarray Printing - 946 Technology

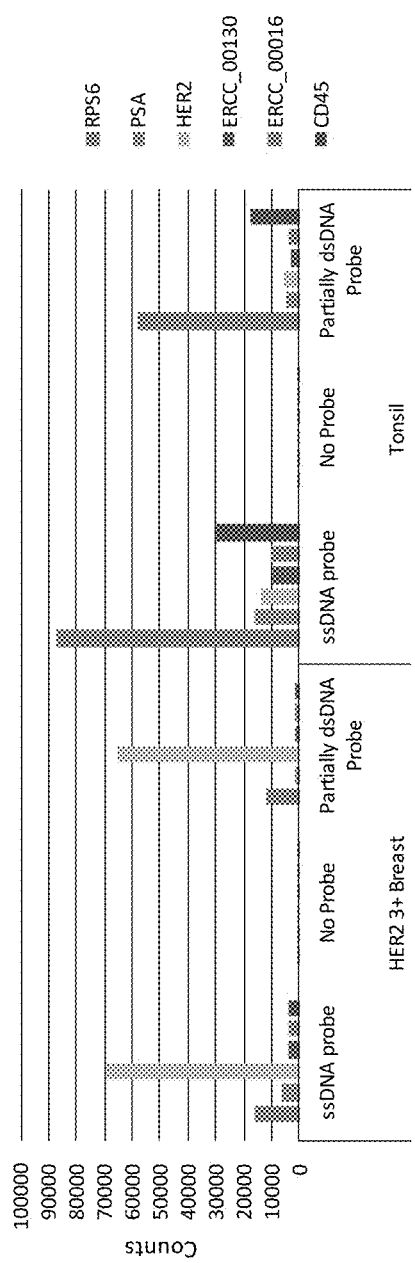
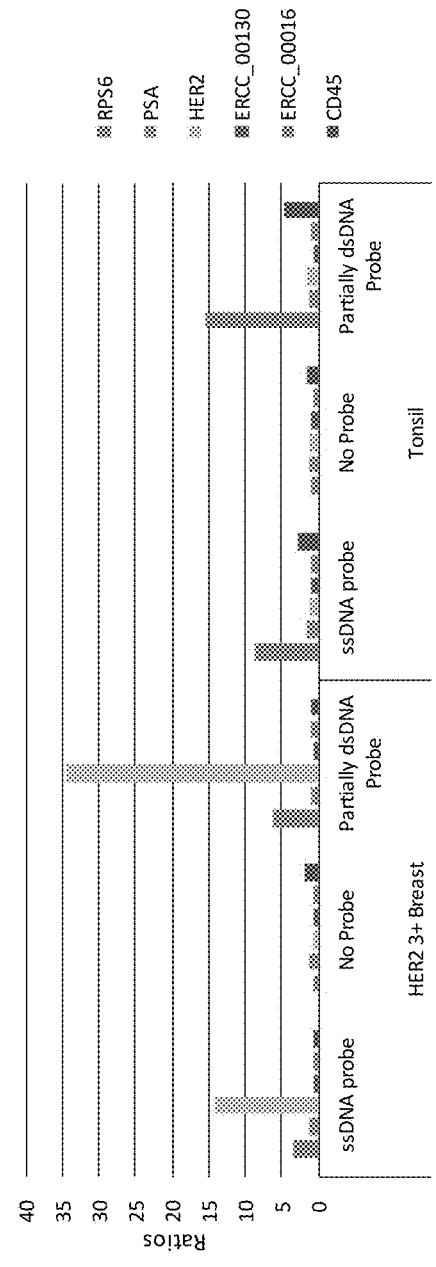
FIG. 55

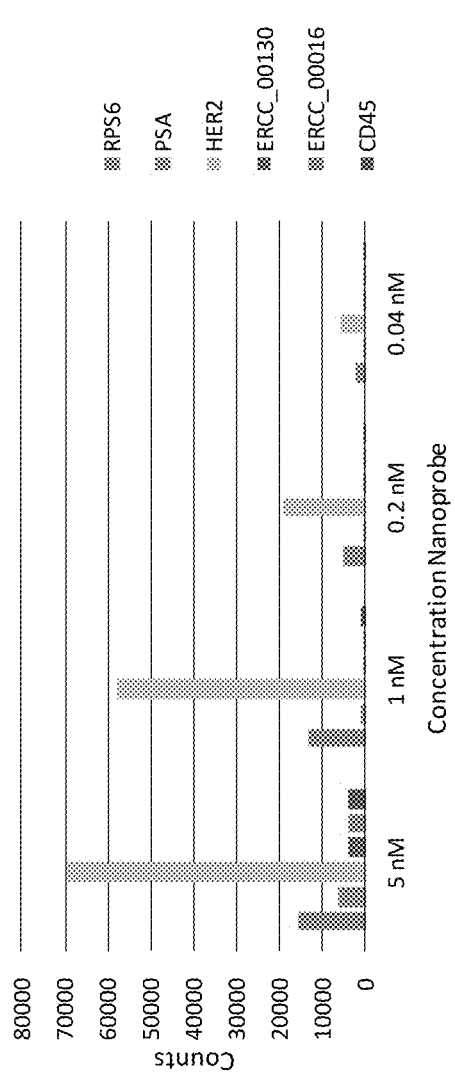
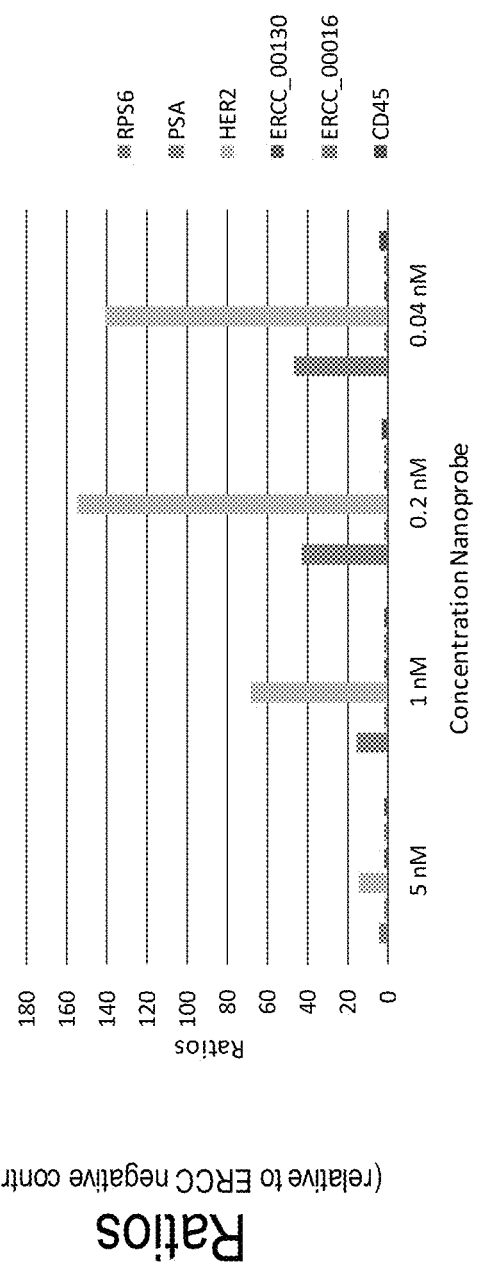
FIG. 58

SIMULTANEOUS QUANTIFICATION OF GENE EXPRESSION IN A USER-DEFINED REGION OF A CROSS-SECTIONED TISSUE

CROSS-REFERENCE TO RELATED APPLICATIONS

This application is a Continuation of U.S. patent application Ser. No. 15/211,230, filed Jul. 15, 2016 (issued as U.S. Pat. No. 10,640,816), which claims priority to and the benefit of U.S. Provisional Application No. 62/193,809, filed Jul. 17, 2015; U.S. Provisional Application No. 62/261,657, filed Dec. 1, 2015; U.S. Provisional Application No. 62/277,289, filed Jan. 11, 2016; and U.S. Provisional Application No. 62/323,023, filed Apr. 15, 2016. Each of the above-mentioned applications is incorporated herein by reference in its entirety.

BACKGROUND OF THE INVENTION

Standard immunohistochemical and in situ hybridization methods allow for simultaneous detection of, at most, six to ten protein or nucleic acid targets, with three to four targets being typical. There exists a need for probes, compositions, methods, and kits for simultaneous, multiplexed detection and quantification of protein and/or nucleic acid expression in a user-defined region of a tissue, user-defined cell, and/or user-defined subcellular structure within a cell.

SUMMARY OF THE INVENTION

The present invention relates to probes, compositions, methods, and kits for simultaneous, multiplexed detection and quantification of protein and/or nucleic acid expression in a user-defined region of a tissue, user-defined cell, and/or user-defined subcellular structure within a cell.

An aspect of the present invention relates to a method including steps of (1) contacting at least one target in or from at least one cell in a tissue sample with at least one probe comprising a target-binding domain and a signal oligonucleotide; (2) providing a force to a location of the tissue sample sufficient to release the signal oligonucleotide; and (3) collecting and identifying the released signal oligonucleotide, thereby detecting the at least one target in or from a specific location of the tissue sample that was provided the force. The specific location is a user-defined region of a tissue, user-defined cell, and/or user-defined subcellular structure within a cell. The target may be a nucleic acid, (e.g., mRNA and miRNA) and/or a protein. The target-binding domain may be a single-stranded nucleic acid, a partially double-stranded nucleic acid, or a protein-binding molecule, e.g., an antibody, a peptide, an aptamer, and a peptoid. In embodiments, two or more targets (i.e., proteins, nucleic acids, and a combination thereof) are detected. In embodiments, 3, 4, 5, 6, 7, 8, 9, 10, 11, 12, 13, 14, 15, 16, 17, 18, 19 20, 30, 40, 50, 60, 70, 80, 90, 100, 200, 300, 400, 500, 600, 700, 800, 900, 1000 or more targets, and any number therebetween, are detected; for example, 800 or more different targets can be detected. In embodiments, detecting includes quantifying the abundance of each target.

In embodiments, the method further includes repeating at least steps (2) and (3) on at least a second specific location of the tissue sample, the second specific location comprising at least a second cell. In embodiments, detecting includes comparing the abundance of the at least one target in or from the first specific location and in or from the at least second specific location. The at least one cell and at least second cell may be the same cell type or distinct cell types. In some embodiments, detecting includes quantifying the abundance of the at least one target in or from a first cell type and in or from the at least a second cell type. In embodiments, first and second cell types are independently selected from a normal cell and an abnormal cell, e.g., a diseased and cancerous cell.

In embodiments, the at least one cell is directly immobilized to a surface or is indirectly immobilized to the surface via at least one other cell. A tissue sample may be a 2 to 1000 µm thick tissue section, e.g., obtained from a formalin-fixed paraffin embedded (FFPE) sample or from an unfixed sample. The at least one cell may be fixed or unfixed. The at least one cell may be stained or labeled prior to step (2) allowing visualization of a subcellular or cellular structure in the stained or labeled cell. Alternately, for tissue sections, a section adjacent to the section that is contacted with the probes may be stained or labeled prior to step (2), thereby allowing estimation of a subcellular, cellular, or tissue-related structure in the corresponding cell or nearby cell in the section that is contacted with the probes. Such staining or labeling techniques are well known in the art.

In the above aspect, at least one probe further includes a linker (e.g., a cleavable linker) located between the target-binding domain and the signal oligonucleotide. The cleavable linker may be photo-cleavable, which is cleaved by light provided by a suitable coherent light source (e.g., a laser and a UV light source) or a suitable incoherent light source (e.g., an arc-lamp and a light-emitting diode (LED)). The light source may irradiate at least one subcellular structure of the at least one cell and the abundance of the at least one nucleic acid target in or from the at least one subcellular structure of the at least one cell can be detected. Also, the light source may first irradiate at least one subcellular structure in the at least one cell and later irradiate at least one subcellular structure in the at least second cell, allowing a comparison of the abundance of the at least one target in or from the at least one subcellular structure in the at least one cell and the at least one subcellular structure in the at least second cell.

In embodiments, the signal oligonucleotide is a single-stranded nucleic acid or a partially double-stranded nucleic acid.

In embodiments, the sample may be cultured cells or dissociated cells (fixed or unfixed) that have been immobilized onto a slide. The sample may comprise cells (including both primary cells and cultured cell lines) and/or tissues (including cultured or explanted). The sample may comprise a cultured cell, a primary cell, or a dissociated cell from an explant.

In embodiments, the illumination of a region of interest smaller that a field of view (for example a single cell or a subcellular structure within a cell) comprises use of a laser scanning device (e.g., confocal) or a digital mirror device (DMD) to direct the light.

In embodiments, a probe is prepared by a cysteine bioconjugation method that is stable, site-specific to, preferably, the antibody's hinge-region heavy-chain. In embodiments, a probe can comprise a plurality (i.e., more than one, e.g., 2, 3, 4, 5, or more) labeled oligonucleotides per antibody.

Detecting comprises a polymerase reaction, a reverse transcriptase reaction, hybridization to an oligonucleotide microarray, mass spectrometry, hybridization to a fluorescent molecular beacon, a sequencing reaction, or nCounter® Molecular Barcodes. In preferred embodiments, nCounter® systems and methods from NanoString Technologies® are used.

In embodiments, the signal oligonucleotide is collected from a tissue via liquid laminar, turbulent, or transitional flow. The flow may be via a channel, e.g., having 25 to 500 μm depth between the tissue and a fluidic device or impermeable barrier placed over the tissue.

In embodiments, the signal oligonucleotide is collected from a solution proximal to, e.g., at least immediately above, the at least one cell. The proximal solution may be collected by aspirating, e.g., via a pipette, a capillary tube, a microarray pin, a flow cell comprising holes, or another suitable aspirating system known in the art or any combination thereof. The capillary tube may comprise an optical device capable of transmitting a light force, e.g., UV light, to the at least one cell. The pipette or a microarray pin may be attached to an array comprising a plurality of pipettes or microarray pins. The proximal solution may comprise an anionic polymer, e.g., dextran sulfate, and/or salmon sperm DNA and/or the collected signal oligonucleotide may be added to a solution comprising an anionic polymer, e.g., dextran sulfate, and/or salmon sperm DNA. Other non-specific blocking agents known in the art in addition to or instead of salmon sperm DNA may be used.

In embodiments, the method provides simultaneous spatially-resolved DNA, RNA, and/or protein detection of a tissue sample.

In embodiments, digital readout comprises a linear dynamic range of greater than or equal to 5 logs.

In embodiments, probes are provided to a sample at concentrations typically less than that used for immunohistochemistry (IHC) or for in situ hybridization (ISH). Alternately, the concentration may be significantly less than that used for IHC or ISH. For example, the probe concentration may be 2 fold less, 5 fold less, 10 fold less, 20 fold less, 25 fold less, 30 fold less, 50 fold less, 60 fold less, 70 fold less, 80 fold less, 90 fold less, 100 fold less, 200 fold less, 300 fold less, 400 fold less, 500 fold less, 600 fold less, 700 fold less, 800 fold less, 900 fold less, 1000 fold less, 2000 fold less, or less and any number in between. In embodiments, probes are provided at a concentration of 100 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, 0.01 nM, and less and any concentration in between.

In embodiments, a tissue sample is attached to a slide and is first imaged using fluorescence (e.g., fluorescently-labeled antibodies and fluorescent stains (e.g., DAPI)) and then expression of proteins and/or nucleic acids is digitally counted from the sample.

In embodiments, a negative purification, e.g., comprising an affinity purification method comprising contacting intact probe molecules with an immobilized oligonucleotide that is complementary to a portion of the intact probe or an immobilized antibody or protein-binding motif that recognizes and binds to a portion of the intact probe, is used to remove intact probe molecules from the released signal oligonucleotides. In embodiments, the intact probe's target binding domain comprises a universal purification tag or sequence that is partially complementary to the immobilized oligonucleotide or is capable of being recognized or bound by the immobilized antibody or protein-binding motif. Any such tag or sequence well-known in the art may be used in these embodiments.

Any aspect or embodiment described herein can be combined with any other aspect or embodiment as disclosed herein. While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 10 shows steps in a method of the present invention in which signal oligonucleotides from one region-of-interest (ROI) are detected.

FIG. 11 shows steps in a method of the present invention in which regions-of-interest are located on a first serial section of a tissue sample and probes are applied to a second serial section of the tissue sample. Signal oligonucleotides are released and collected from probes bound to targets in a first region-of-interest of the second serial section. Then, signal oligonucleotides are released and collected from probes bound to targets in a second (up to the $n^{th}$) region-of-interest of the second serial section.

FIG. 23 shows nCounter® data for CD45 conjugate release from FFPE lymph node tissue sections (5 µm thickness) as a function of UV illumination area (100 µm to 1 mm in diameter) and from the same experiment as shown in FIGS. 21 and 22.

FIG. 24 shows nCounter® data for PD1 conjugate release from FFPE lymph node tissue sections (5 µm thickness) as a function of UV illumination area (100 µm to 1 mm in diameter) and from the same experiment as shown in FIGS. 21 to 23.

FIG. 31A and FIG. 31D are photomicrographs showing UV illumination using a digital mirror device (DMD) of single cells (in bright white) in a tonsil tissue sample. FIG. 31B highlights the single cells noted in FIG. 31A. FIG. 31D highlights the single cell noted in FIG. 31C.

FIG. 35 shows an embodiment in which a portion of a tissue or sample is illuminated, e.g., with a microscope, i.e., UV cleavage under Microscope (Time titration experiment).

FIG. 39 shows an embodiment in which a tissue is embedded in flow cell. Data for multiple fractions is shown. As with the data of FIG. 38, here a region of interest is pre-identified for expression of a fluorescently-labeled marker. Also shown are photographs and a schematic showing configuration of the apparatus.

FIG. 42B shows data in the embodiments using a flow cell with small holes (96 hole format).

FIG. 47 is a schematic showing eluent collection with an open surface for a multi-region of interest aspiration embodiment or for a single region of interest. Here is shown a multi-tube array using pipetting vs capillary action for aspiration/dispensing and a single tube/pipet with fixed position.

FIG. 55 shows RNA expression data obtained from single-stranded DNA probes and partially double-stranded DNA probes.

FIG. 58 shows specificity of probes increase at non-standard, sub-nM concentrations.

DETAILED DESCRIPTION OF THE INVENTION

Figure 1:
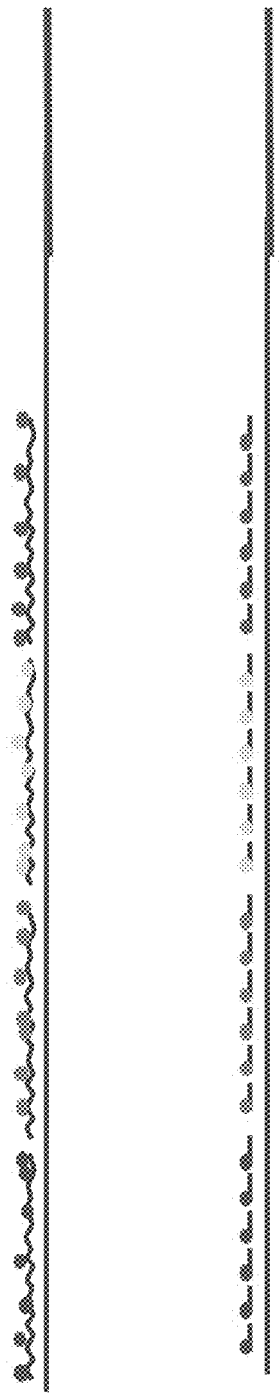
FIG. 1 shows two exemplary probes. Nucleic acid backbones (either single-stranded DNA or single-stranded RNA) are shown as a straight, black line. The probes each include a target-binding domain, shown in red. The top probe includes labeled RNA segments hybridized to the nucleic acid backbone whereas the bottom probe includes labeled DNA oligonucleotides hybridized to the nucleic acid backbone. A cleavable motif (e.g., a cleavable linker, not shown) may be located between the backbone and a target-binding domain or within the backbone. The cleavable motif allows release of a signal oligonucleotide from a bound target nucleic acid or protein; then, the signal oligonucleotide is collected and detected.

The present invention is based in part on probes, compositions, methods, and kits for simultaneous, multiplexed detection and quantification of protein and/or nucleic acid expression in a user-defined region of a tissue, user-defined cell, and/or user-defined subcellular structure within a cell.

The present invention provides a comparison of the identity and abundance of target proteins and/or target nucleic acids present in a first region of interest (e.g., tissue type, a cell (including normal and abnormal cells), and a subcellular structure within a cell) and the identity and abundance of target proteins and/or target nucleic acids present in a second region of interest. There is no pre-defined upper limit to the number of regions of interest and comparisons that can be made; the upper limit relates to the size of the region of interest relative the size of the sample. As examples, when a single cell represent a region of interest, then a section may have hundreds to thousands of regions of interest; however, if a tissue section includes only two cell types, then the section may have only two regions of interest (each including only one cell type).

The present invention provides a higher degree of multiplexing than is possible with standard immunohistochemical or in situ hybridization methods. Standard immunohistochemical methods allow for maximal simultaneous detection of six to ten protein targets, with three to four protein targets being more typical. Similarly, in situ hybridization methods are limited to simultaneous detection of fewer than ten nucleic acid targets. The present invention provides detection of large combinations of nucleic acid targets and/or protein targets from a defined region of a sample. The present invention provides an increase in objective measurements by digital quantification and increased reliability and consistency, thereby enabling comparison of results among multiple centers.

The probes of the present invention may have nucleic acid backbones (single-stranded DNA or RNA) having defined positions capable of being hybridized (non-covalently bound) with at least one labeled oligonucleotide. See, FIG. 1. Such probes (which have defined positions capable of being hybridized with at least one labeled oligonucleotide are also referred herein as reporter probes. The number of positions on a reporter probe's backbone ranges from 1 to 100 or more. In embodiments, the number of positions ranges from 1, 2, 3, 4, 5, 6, 7, 8, 9, 10 to 15, 20, 30, 40, or 50, or any range in between. Indeed, the number of positions (for detecting a target nucleic acid and/or for detecting a target protein) on a backbone is without limit since engineering such a backbone is well-within the ability of a skilled artisan. The number of target nucleic acids and/or proteins detectable by a set of probes depends on the number of positions included in the probes' backbones.

As used herein a labeled oligonucleotide relates to an RNA segment including a detectable label or a DNA oligonucleotide including a detectable label.

A position of a nucleic acid backbone may be hybridized (non-covalently bound) with at least one labeled oligonucleotide. Alternately, a position may be hybridized with at least one oligonucleotide lacking a detectable label. Each position can hybridize to 1, 2, 3, 4, 5, 6, 7, 8, 9, 10, 11, 12, 13, 14, 15, 16, 17, 18, 19, 20, or 21 to 100 labeled (or unlabeled) oligonucleotides or more. The number of labeled oligonucleotides hybridized to each position depends on the length of the position and the size of the oligonucleotides. A position may be between about 300 to about 1500 nucleotides in length. The lengths of the labeled (or unlabeled) oligonucleotides vary from about 20 to about 1500 nucleotides in length. In embodiments, the lengths of labeled (or unlabeled) oligonucleotides vary from about 800 to about 1300 ribonucleotides. In other embodiments, the lengths of labeled (or unlabeled) oligonucleotides vary from about 20 to about 55 deoxyribonucleotides; such oligonucleotides are designed to have melting/hybridization temperatures of between about 65 and about 85° C., e.g., about 80° C. For example, a position of about 1100 nucleotides in length may hybridize to between about 25 and about 45 oligonucleotides comprising, each oligonucleotide about 45 to about 25 deoxyribonucleotides in length. In embodiments, each position is hybridized to about 34 labeled oligonucleotides of about 33 deoxyribonucleotides in length. The labeled oligonucleotides are preferably single-stranded DNA.

Each labeled oligonucleotide may be labeled with one or more detectable label monomers. The label may be at a terminus of an oligonucleotide, at a point within an oligonucleotide, or a combination thereof. Oligonucleotides may comprise nucleotides with amine-modifications, which allow coupling of a detectable label to the nucleotide.

Labeled oligonucleotides of the present invention can be labeled with any of a variety of label monomers, such as a fluorochrome, quantum dot, dye, enzyme, nanoparticle, chemiluminescent marker, biotin, or other monomer known in the art that can be detected directly (e.g., by light emission) or indirectly (e.g., by binding of a fluorescently-labeled antibody). Preferred examples of a label that can be utilized by the invention are fluorophores. Several fluorophores can be used as label monomers for labeling nucleotides including, but not limited to, GFP-related proteins, cyanine dyes, fluorescein, rhodamine, ALEXA Flour™, Texas Red, FAM, JOE, TAN/IRA, and ROX. Several different fluorophores are known, and more continue to be produced, that span the entire spectrum.

Labels associated with each position (via hybridization of a position with a labeled oligonucleotide) are spatially-separable and spectrally-resolvable from the labels of a preceding position or a subsequent position. An ordered series of spatially-separable and spectrally-resolvable labels of a probe is herein referred to as barcode or as a label code. The barcode or label code allows identification of a target nucleic acid or target protein that has been bound by a particular probe.

The labeled oligonucleotides hybridize to their positions under a standard hybridization reaction, e.g., 65° C., 5×SSPE; this allows for self-assembling reporter probes or probes. Probes using longer RNA molecules as labeled oligonucleotide (e.g., as described in US2003/0013091) must be pre-assembled at a manufacturing site rather than by an end user and at higher temperatures to avoid cross-linking of multiple backbones via the longer RNA molecules; the pre-assembly steps are followed by purification to remove excess un-hybridized RNA molecules, which increase background. Use of the short single-stranded labeled oligonucleotide (e.g., comprising deoxyribonucleotides) greatly simplifies the manufacturing of the probes and reduces the costs associated with their manufacture.

In embodiments, probes are provided to a sample at concentrations typically less than that used for immunohistochemistry (IHC) or for in situ hybridization (ISH). Alternately, the concentration may be significantly less than that used for IHC or ISH. For example, the probe concentration may be 2 fold less, 5 fold less, 10 fold less, 20 fold less, 25 fold less, 30 fold less, 50 fold less, 60 fold less, 70 fold less, 80 fold less, 90 fold less, 100 fold less, 200 fold less, 300 fold less, 400 fold less, 500 fold less, 600 fold less, 700 fold less, 800 fold less, 900 fold less, 1000 fold less, 2000 fold less, or less and any number in between. In embodiments, probes are provided at a concentration of 100 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, 0.01 nM, and less and any concentration in between.

Probes can be detected and quantified using commercially-available cartridges, software, systems, e.g., the nCounter® System using the nCounter® Cartridge.

Background noise, during protein detection, can be reduced by performing a negative purification of the intact probe molecule. This can be done by conducting an affinity purification of the antibody or photo-cleavable linker after collection of eluate from a region of interest. Normally, released signal oligonucleotides will not be pulled out of solution. A protein-G or -O mechanism in a pipet tip, tube, or plate can be employed for this step. Such devices and reagents commercially available.

Background noise, during nucleic acid detection, can be reduced by performing a negative purification of the intact probe molecule. This can be done by conducting an affinity purification of the target binding domain or photo-cleavable linker after collection of eluate from a region of interest. Normally, released signal oligonucleotides will not be pulled out of solution. To assist in the negative purification, a universal purification sequence may included in a probe, e.g., in the target binding domain.

FIG. 1 shows two exemplary probes including a single-stranded nucleic acid backbone and a target-binding domain, shown in red. The top probe includes labeled RNA segments hybridized to positions in the backbone whereas the bottom probe includes labeled DNA oligonucleotides hybridized to positions in the nucleic acid backbone. The colors shown in FIG. 1, and elsewhere in this disclosure, are non-limiting; other colored labels and other detectable labels known in the art can be used in the probes of the present invention.

Figure 2:
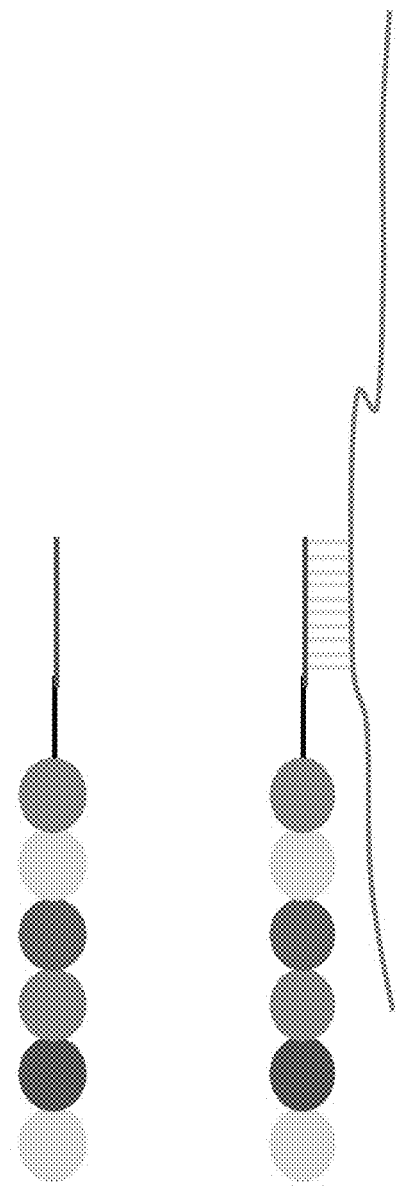
FIG. 2 shows a first type of a probe that can bind directly to a target nucleic acid (top). In the below image, the probe has bound to the target nucleic acid, shown as a blue curvilinear line. In this figure and in later figures, a reporter probe includes six positions hybridized to labeled oligonucleotides (identified by a colored circle). Since the probe comprises positions that can be hybridized to labeled oligonucleotides, the probe can also be referred to as a reporter probe.
Figure 4:
FIG. 4 shows a second type of a probe (or reporter probe) that can bind indirectly to a target nucleic acid in a sample (top). Here, the probe's target is an intermediary oligonucleotide, shown in green, which in turn binds to the target nucleic acid in a sample, shown as a blue curvilinear line in the bottom image. It could be said that the intermediary oligonucleotide is a probe, as defined herein, since it comprises a nucleic acid backbone and is capable of binding a target nucleic acid.

Probes of the present invention can be used for detecting a target nucleic acid. FIGS. 2 and 4 illustrate this aspect. Such a probe includes at least a backbone and a target nucleic acid-binding region. The target nucleic acid-binding region is preferably at least 15 nucleotides in length, and more preferably is at least 20 nucleotides in length. In specific embodiments, the target nucleic acid-binding region is approximately 10 to 500, 20 to 400, 25, 30 to 300, 35, 40 to 200, or 50 to 100 nucleotides in length. Probes and methods for binding and identifying a target nucleic acid have been described in, e.g., US2003/0013091, US2007/0166708, US2010/0015607, US2010/0261026, US2010/0262374, US2010/0112710, US2010/0047924, and US2014/0371088, each of which is incorporated herein by reference in its entirety. A target nucleic acid may be DNA or RNA and preferably cRNA, messenger RNA (mRNA) or miRNA; preferably the DNA is cDNA.

Figure 3:
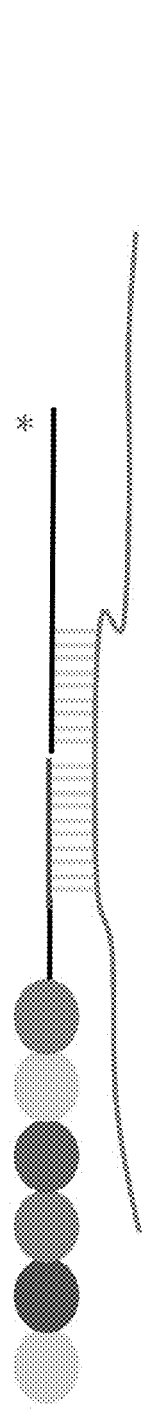
FIG. 3 shows a first type of dual-probe composition of the present invention. Here, the first type of probe binds directly to a target nucleic acid and a first type capture probe binds directly to the target nucleic acid. The capture probe may include at least one affinity reagent, which is shown as an asterisk. The target nucleic acid in a sample is shown as a blue curvilinear line.

The probes of the present invention can be used to directly hybridize to a target nucleic acid. FIG. 2 illustrates a probe (or composition) of this embodiment. The probes include a target nucleic-acid binding domain, shown in red. The target nucleic acid is shown as a blue curvilinear line. FIG. 3 illustrates a dual probe composition including the probe of FIG. 2 and a capture probe. The capture probe comprises at least one affinity reagent, shown as an asterisk. The at least one affinity moiety may be attached to the capture probe by covalent or non-covalent means. Various affinity moieties appropriate for purification and/or for immobilization are known in the art. Preferably, the affinity moiety is biotin, avidin, or streptavidin. Other affinity tags are recognized by specific binding partners and thus facilitate isolation and immobilization by affinity binding to the binding partner, which can be immobilized onto a solid support. In these figures, each probe includes six positions hybridized to labeled oligonucleotides, each positions is identified by a colored circle.

Any probe of the present invention may comprise an affinity moiety.

Figure 5:
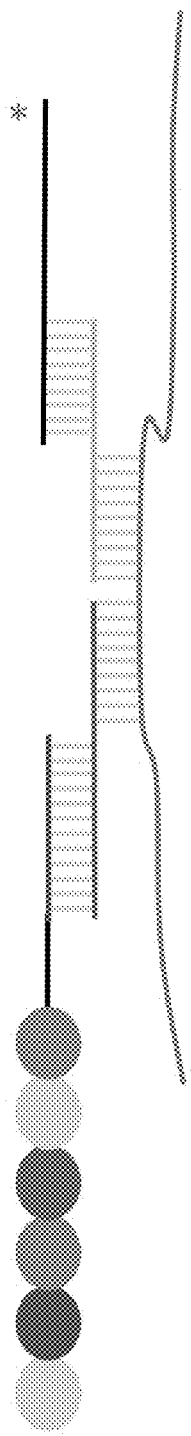
FIG. 5 shows a second type of dual-probe composition of the present invention. Here, the second type of probe binds indirectly to a target nucleic acid in a sample (via an intermediary oligonucleotide, shown in green) and a second type capture probe binds indirectly to the target nucleic acid in the sample (via another intermediary oligonucleotide, shown in orange). The capture probe may include at least one affinity reagent, which is shown as an asterisk.

The probes of the present invention can be used to indirectly hybridize to a target nucleic acid present in a sample (via an intermediary oligonucleotide). FIG. 4 illustrates a probe (or composition) of this embodiment. The probes include a target nucleic-acid binding domain, shown in red, which binds to a synthetic oligonucleotide (the intermediary oligonucleotide; shown in green) that in turn binds to a target nucleic acid in a biological sample. It could be said that the intermediary oligonucleotide is a probe, as defined herein, since it comprises a nucleic acid backbone and is capable of binding a target nucleic acid. The target nucleic acid present in a biological sample is shown as a blue curvilinear line. FIG. 5 illustrates a dual-probe composition including the probe of FIG. 4 and a capture probe. In these embodiments, a probe's target nucleic acid-binding region hybridizes to a region of an intermediary oligonucleotide (i.e., a synthetic oligonucleotide) which is different from the target nucleic acid present in a sample. Thus, the probe's target binding region is independent of the ultimate target nucleic acid in the sample. This allows economical and rapid flexibility in an assay design, as the target (present in a sample)-specific components of the assay are included in inexpensive and widely-available synthetic DNA oligonucleotides rather than the more expensive probes. Such synthetic oligonucleotides are simply designed by including a region that hybridizes to the target nucleic acid present in a sample and a region that hybridizes to a probe. Therefore, a single set of indirectly-binding probes can be used to detect an infinite variety of target nucleic acids (present in a sample) in different experiments simply by replacing the target-specific (synthetic) oligonucleotide portion of the assay.

A probe or probe of the present invention can include a region which permits the release of a signal oligonucleotide following the application of a suitable force. In one non-limited example, the region is a cleavable motif (e.g., a restriction enzyme site or cleavable linker). The cleavable motif allows release of a signal oligonucleotide from a bound target nucleic acid or protein and the signal oligonucleotide is then collected and detected. As used herein a signal oligonucleotide is a region of a probe that presently has positions hybridized with at least one labeled oligonucleotide or is a region of a probe (e.g., a nucleic acid molecule) that can be released from the target-binding domain of the probe. A signal oligonucleotide is said to be releasable when it can be separated (i.e., cleaved and released) from the remainder of the probe. Examples of cleavable motives include but are not limited to photo-cleavable linkers.

Figure 6:
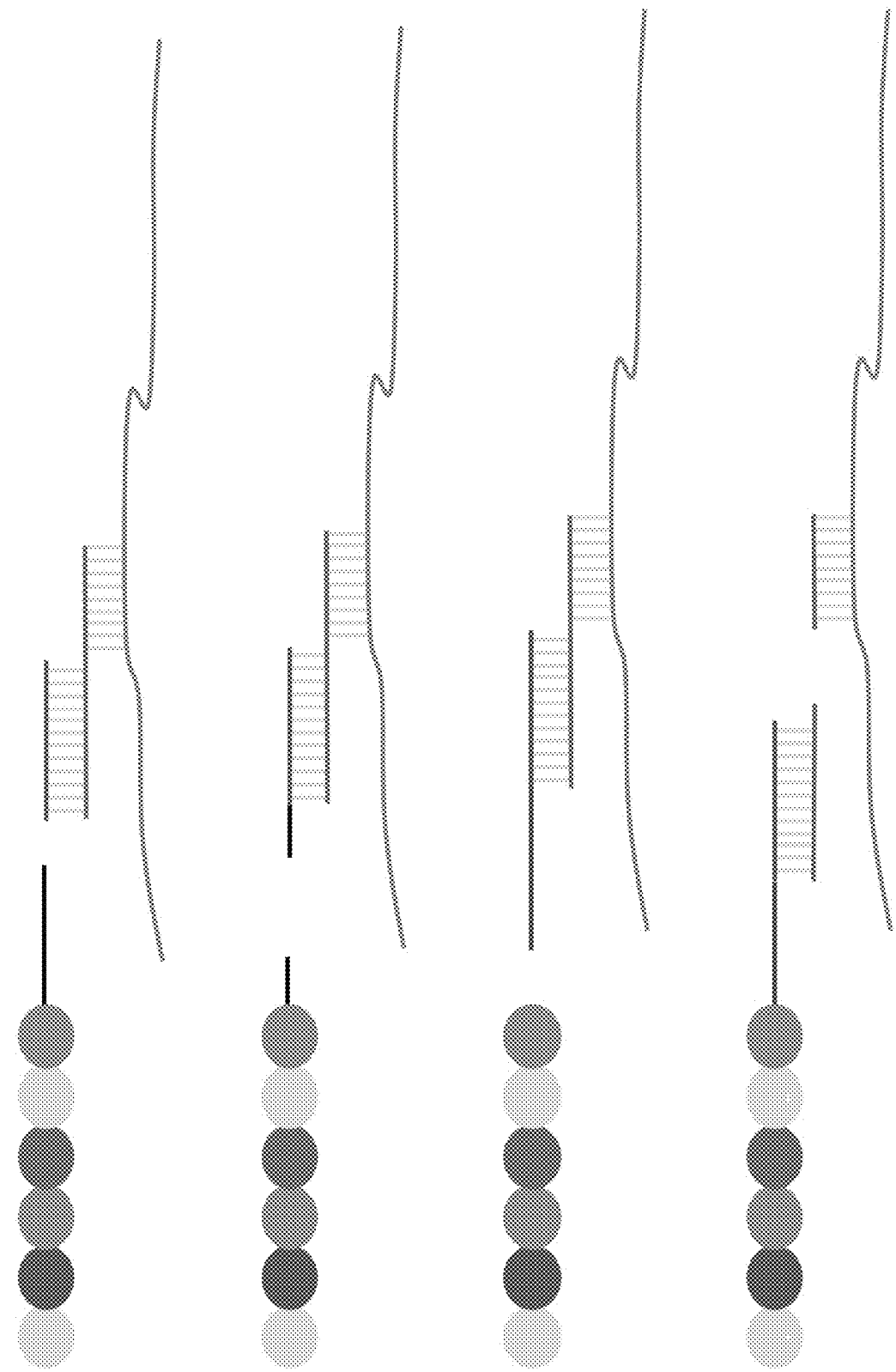
FIG. 6 shows release of signal oligonucleotides from second type probes (illustrated in FIG. 4) that are bound indirectly to a target nucleic acid in a sample. The location of a cleavable motif within a probe (or in a reporter probe) affects which material is included with a released signal oligonucleotide.

In a probe of the present invention (as described herein), the cleavable motif may be located between a nucleic acid and a target binding domain, the backbone and a target-binding domain, or within the backbone. In FIG. 6, non-limiting options for a cleavable motif's position can be inferred from gaps within a probe or a gap within an intermediary oligonucleotide.

Figure 7:
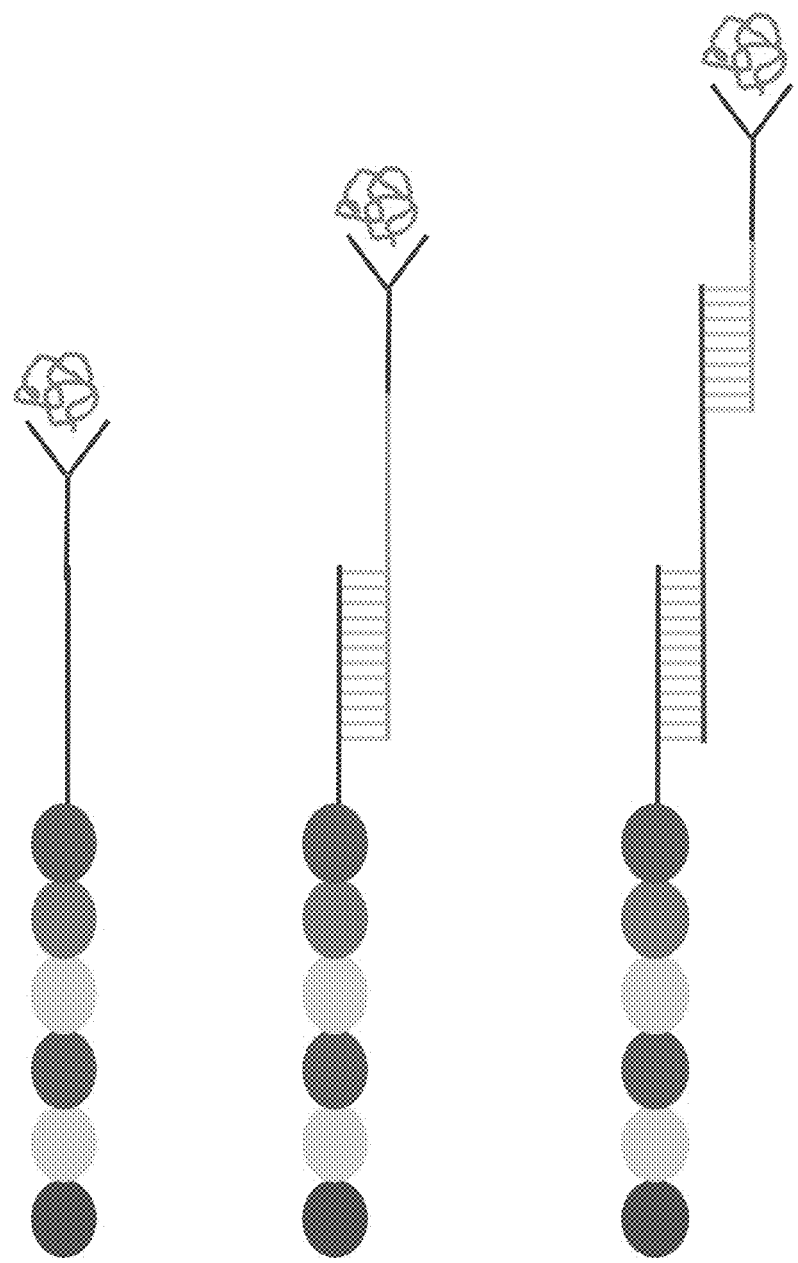
FIG. 7 shows three types of probes used for detecting proteins. In the top configuration, a probe comprises a nucleic acid attached to a protein-binding domain; in this configuration, a cleavable motif (e.g., a cleavable linker, not shown) may be included between the nucleic acid and protein-binding domain or within the nucleic acid itself. In the middle configuration, a protein-binding domain is attached to a nucleic acid and a probe hybridizes to the nucleic acid. The probe (comprising the target-binding domain and the nucleic acid attached to the protein-binding domain (shown in green)) can be bound by a probe before or after the target binding domain binds a protein target (As shown in FIG. 8). A cleavable motif may be included in either or both of the backbone or the nucleic acid attached to the protein-binding domain. The first or second type probe shown in FIGS. 2 and 4 may be used in this configuration for detecting a protein. In the bottom configuration, a protein-binding domain is attached to a nucleic acid and an intermediary oligonucleotide (shown in red) hybridizes to both a probe and to the nucleic acid attached to the protein-binding domain. The first or second type probe shown in FIGS. 2 and 4 may be used in this configuration for detecting a protein.
Figure 8:
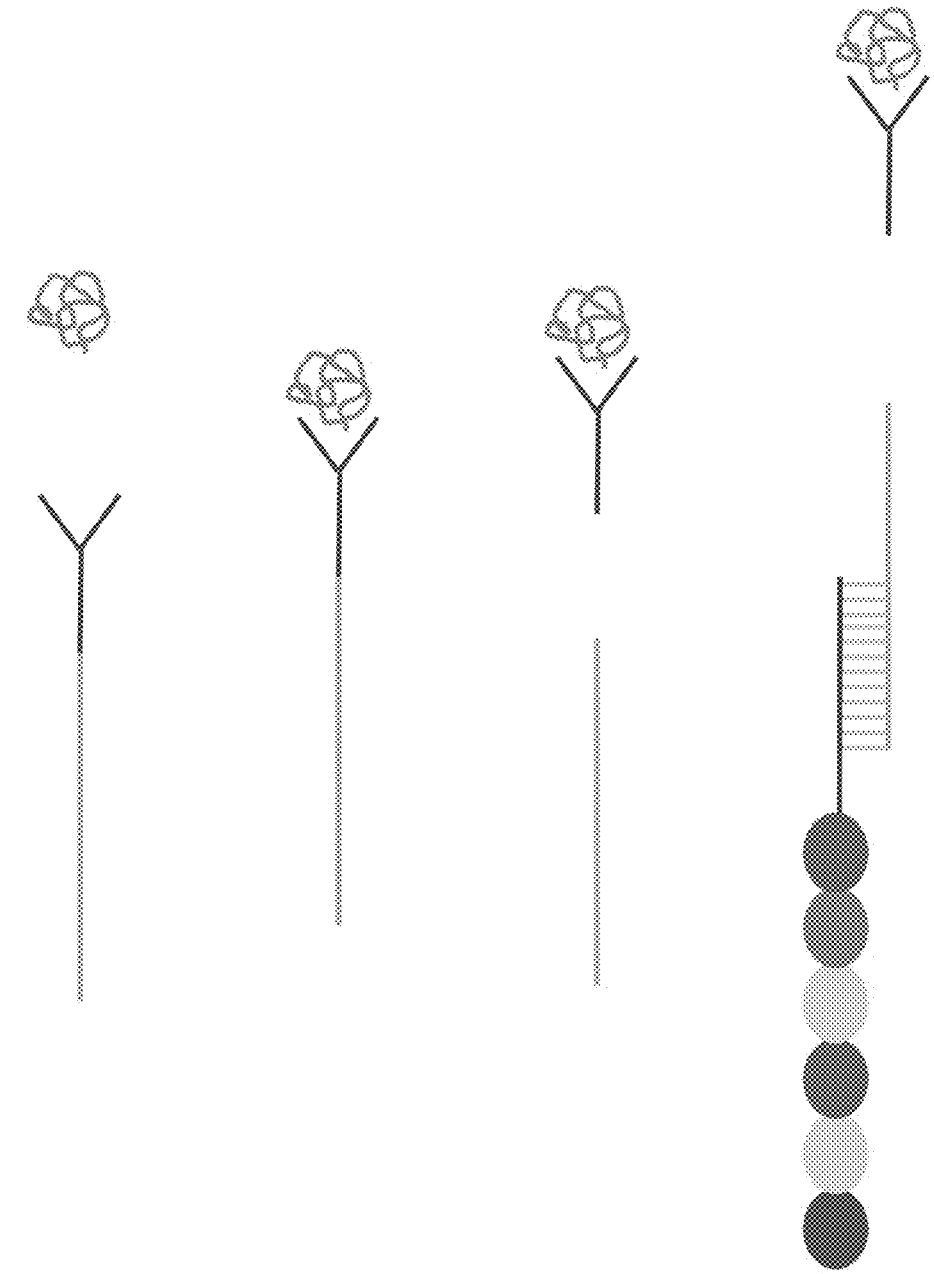
FIG. 8 shows the middle and bottom probes of FIG. 7. The top two images show the probe before and after it has bound a protein. The next image shows the probe after its cleavable motif has been cleaved; in this image the cleavable motif is between the nucleic acid and the target binding domain. Once the nucleic acid has been released, it can be considered a signal oligonucleotide. In the bottom image, the signal oligonucleotide (released nucleic acid of the probe) is bound by a reporter probe (e.g., as shown in FIGS. 2 and 4).

Probes of the present invention can be used for detecting a target protein. FIG. 7 illustrates probes (or compositions) of this embodiment. Such probes include at least a backbone and a target protein-binding region. In protein-targeting probes of the present invention, a signal oligonucleotide may the nucleic acid attached to the protein-binding domain. In these probes, the signal oligonucleotide is targeted and bound by a probe that comprises positions for hybridizing to labeled oligonucleotides. Such a probe is shown in FIG. 7, middle image. There, the signal oligonucleotide is seen as a green line. The probe may be bound by a probe before the probe (via its protein-binding domain) binds a protein or afterward it binds the protein. The signal oligonucleotide need not be bound by the probe until it has already been released from the target-binding domain (this embodiment is not shown).

A probe's region capable of binding to a target protein include molecules or assemblies that are designed to bind with at least one target protein, at least one target protein surrogate, or both and can, under appropriate conditions, form a molecular complex comprising the protein probe and the target protein. The region capable of binding to a target protein includes an antibody, a peptide, an aptamer, or a peptoid. The antibody can be obtained from a variety of sources, including but not limited to polyclonal antibody, monoclonal antibody, monospecific antibody, recombinantly expressed antibody, humanized antibody, plantibodies, and the like. The terms protein, polypeptide, peptide, and amino acid sequence are used interchangeably herein to refer to polymers of amino acids of any length. The polymer may be linear or branched, it may comprise modified amino acids, and it may be interrupted by non-amino acids or synthetic amino acids. The terms also encompass an amino acid polymer that has been modified, for example, by disulfide bond formation, glycosylation, lipidation, acetylation, phosphorylation, or any other manipulation, such as conjugation with a labeling component. As used herein the term amino acid refers to either natural and/or unnatural or synthetic amino acids, including but not limited to glycine and both the D or L optical isomers, and amino acid analogs and peptidomimetics. Probes and methods for binding and identifying a target protein have been described, e.g., in US2011/0086774, the contents of which is incorporated herein by reference in its entirety.

In embodiments, a probe is prepared by a cysteine bioconjugation method that is stable, site-specific to, preferably, the antibody's hinge-region heavy-chain. This preparation method provides relatively controllable labeled oligonucleotides to antibody stoichiometric ratios. A probe can comprise a plurality (i.e., more than one, e.g., 2, 3, 4, 5, or more) labeled oligonucleotides per antibody. Generally, "heavier" probes, which comprise 3 or 4 labeled oligonucleotides per antibody, are significantly less sensitive than antibodies lacking a labeled oligonucleotide or "lighter" probes, which comprise 1 or 2 labeled oligonucleotides per antibody.

Protein-targeting probes and nucleic acid-targeting probes may be applied simultaneously as long as conditions allow for binding of both a protein target and a nucleic acid target. Alternately, protein-targeting probes and nucleic acid-targeting probes may be applied sequentially when conditions allowing for binding of both a protein target and a nucleic acid target are not possible.

A set of probes is synonymous with a composition of probes. A set of probes includes at least one species of probes, i.e., directed to one target. A set of probes preferably includes at least two, e.g., 3, 4, 5, 6, 7, 8, 9, 10, 11, 12, 13, 14, 15, 16, 17, 18, 19 20, 30, 40, 50, 60, 70, 80, 90, 100, 200, 300, 400, 500, 600, 700, 800, 900, 1000 or more species of probes. A probe set may include one or multiple copies of each species of probe.

A first set of probes only may be applied to a sample. Alternately, a second set (or higher number) of probes may be later applied to the sample. The first set and second (or higher number) may target only nucleic acids, only proteins, or a combination thereof.

In the present invention, two or more targets (i.e., proteins, nucleic acids, or a combination thereof) are detected; 3, 4, 5, 6, 7, 8, 9, 10, 11, 12, 13, 14, 15, 16, 17, 18, 19 20, 30, 40, 50, 60, 70, 80, 90, 100, 200, 300, 400, 500, 600, 700, 800, 900, 1000 or more targets, and any number there between, are detected.

A set of probes may be pre-defined based upon the cell type or tissue type to be targeted. For example, if the tissue is a breast cancer, then the set of probes will include probes directed to proteins relevant to breast cancer cells (e.g., Her2, EGFR, and PR) and/or probes directed to proteins relevant to normal breast tissues. Additionally, the set of probes may be pre-defined based upon developmental status of a cell or tissue to be targeted. Alternately, the set of probes may be pre-defined based upon subcellular localizations of interest, e.g., nucleus, cytoplasm, and membrane. For example, antibodies directed to Foxp3, Histone H3, or P-S6 label the nucleus, antibodies directed to CD3, CD4, PD-1, or CD45RO label the cytoplasm, and antibodies directed to PD-L1 label membranes.

A probe may be chemically synthesized or may be produced biologically using a vector into which a nucleic acid encoding the probe has been cloned.

Any probe or set of probes described herein may be used in methods and kits of the present invention.

For the herein-described probes, association of label code to target nucleic acid or target protein is not fixed.

Probes of the present invention can be used to detect a target nucleic acid or protein present in any sample, e.g., a biological sample. As will be appreciated by those in the art, the sample may comprise any number of things, including, but not limited to: cells (including both primary cells and cultured cell lines) and tissues (including cultured or explanted). In embodiments, a tissue sample (fixed or unfixed) is embedded, serially sectioned, and immobilized onto a microscope slide. As is well known, a pair of serial sections will include at least one cell that is present in both serial sections. Structures and cell types, located on a first serial section will have a similar location on an adjacent serial section. The sample can be cultured cells or dissociated cells (fixed or unfixed) that have been immobilized onto a slide.

In embodiments, a tissue sample is a biopsied tumor or a portion thereof, i.e., a clinically-relevant tissue sample. For example, the tumor may be from a breast cancer. The sample may be an excised lymph node.

The sample can be obtained from virtually any organism including multicellular organisms, e.g., of the plant, fungus, and animal kingdoms; preferably, the sample is obtained from an animal, e.g., a mammal. Human samples are particularly preferred.

In some embodiments, the probes, compositions, methods, and kits described herein are used in the diagnosis of a condition. As used herein the term diagnose or diagnosis of a condition includes predicting or diagnosing the condition, determining predisposition to the condition, monitoring treatment of the condition, diagnosing a therapeutic response of the disease, and prognosis of the condition, condition progression, and response to particular treatment of the condition. For example, a tissue sample can be assayed according to any of the probes, methods, or kits described herein to determine the presence and/or quantity of markers of a disease or malignant cell type in the sample (relative to the non-diseased condition), thereby diagnosing or staging a disease or a cancer.

In general, samples attached to a slide can be first imaged using fluorescence (e.g., fluorescent antibodies or fluorescent stains (e.g., DAPI)) to identify morphology, regions of interest, cell types of interest, and single cells and then expression of proteins and/or nucleic acids can be digitally counted from the sample on the same slide.

Compositions and kits of the present invention can include probes and other reagents, for example, buffers and other reagents known in the art to facilitate binding of a protein and/or a nucleic acid in a sample, i.e., for performing hybridization reactions.

A kit also will include instructions for using the components of the kit, including, but not limited to, information necessary to hybridize labeled oligonucleotides to a probe, to hybridize a probe to a target-specific oligonucleotide, to hybridize a target-specific oligonucleotide to a target nucleic acid and/or to hybridize a probe to target protein.

An exemplary protocol for detecting target nucleic acids and/or target proteins is described as follows and as shown in FIGS. 10 to 14 (top).

Cells (live or fixed) or tissue sections (e.g., formalin-fixed paraffin embedded (FFPE)) that are prepared consistent with multiplexed immunohistochemistry methods and/or nucleic acid in situ hybridization methods are prepared and immobilize onto a glass slide or suitable solid support. Access to the surface of cells or tissue-section is preserved, allowing for fluidic exchange; this can be achieved by using a fluidic chamber reagent exchange system (e.g., Grace™ Bio-Labs, Bend Oreg.). Regions-of-interest (ROIs) are identified on the serial section to be provided probes or on an adjacent serial section. In the first instance, full "macroscopic-features" imaging methodology to cell/tissues of interest is performed, e.g., DAPI staining, membrane staining, mitochondrial staining, specific epitope staining, and specific transcript staining, to determine overall macroscopic features of cell/tissue of interest. Alternately, regions-of-interest (ROIs) are identified on a serial section adjacent to the serial section to be provided the probes; here, full "macroscopic-features" imaging (as described above) is performed on a first serial section (section #1 in FIGS. 11 and 12). This imaging will generally identify regions-of-interest on the adjacent serial section (red line in panel B in FIG. 10 and green oval and green triangle of section #2 in FIGS. 11 and 12) where signal oligonucleotides will be released from the probes upon application of a suitable and directed force. Serial sections may be approximately 5 µm to 15 µm from each other.

Figure 13:
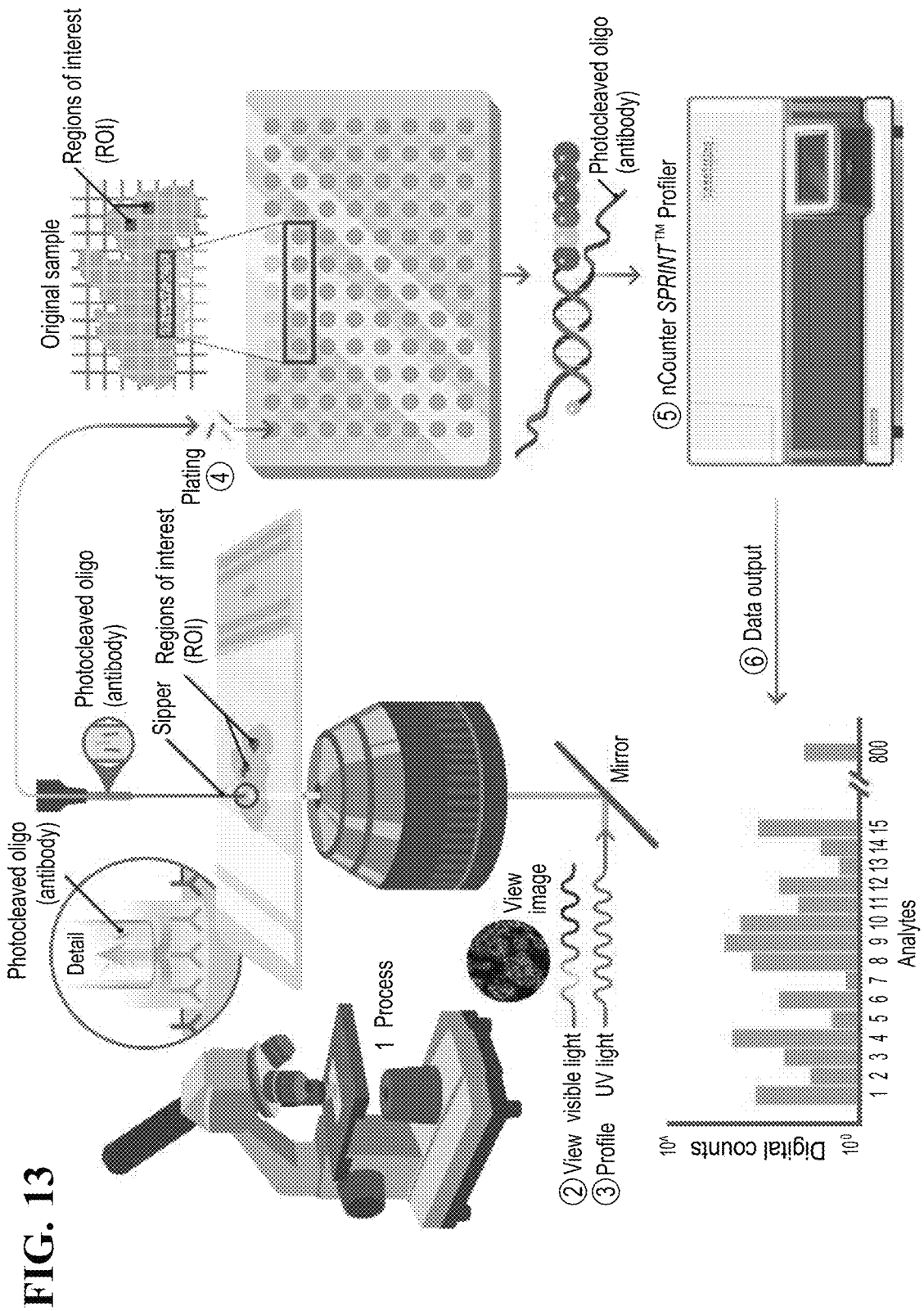
FIG. 13 illustrates steps in methods of the present invention. The method shown may be referred herein as "nCounter® Digital Multiplexed Immunohistochemistry (IHC)".
Figure 14:
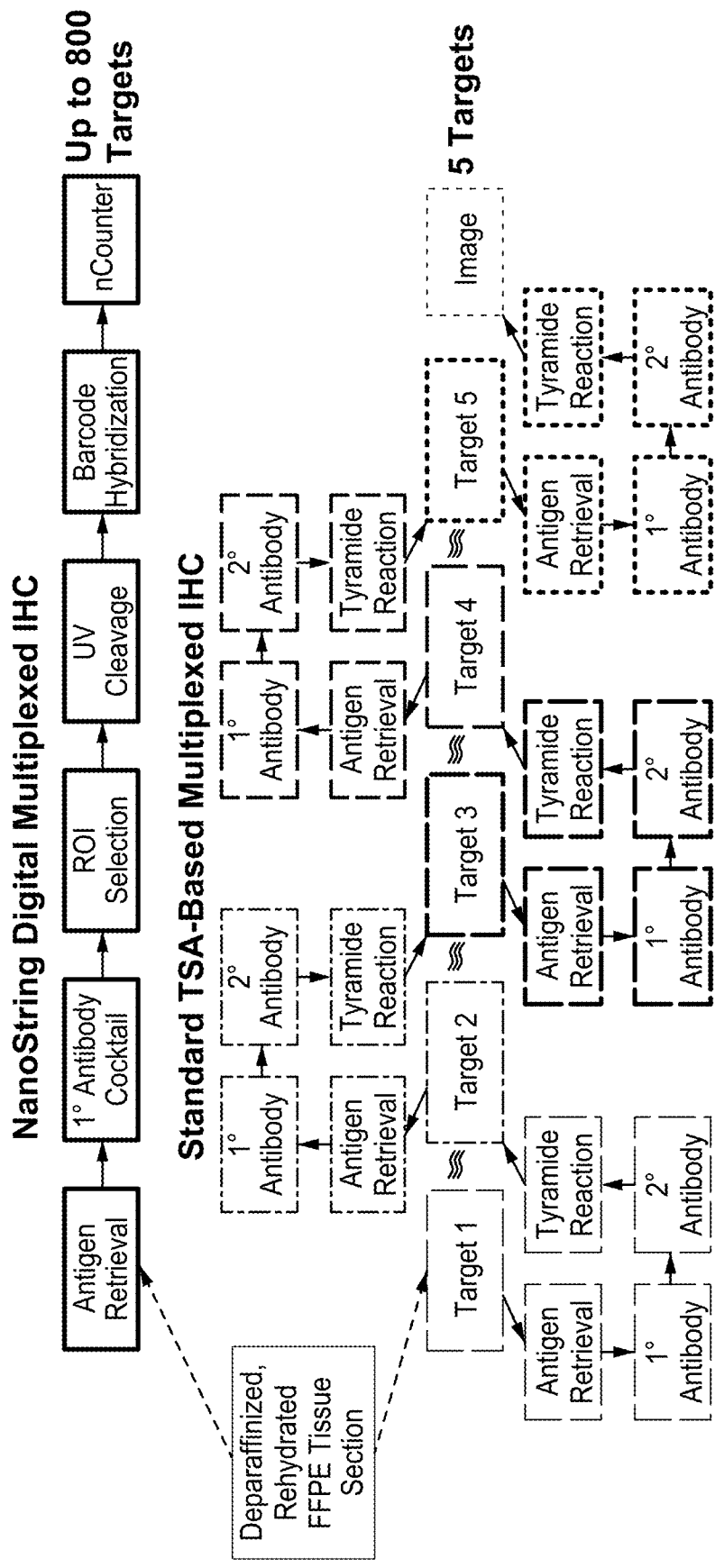
FIG. 14 is a flow chart demonstrating the simplified workflow and higher multiplexing capable with nCounter® Digital Multiplexed IHC (top) when compared to standard TSA-based multiplexed IHC (bottom).

FIG. 13 and FIG. 14 (top) further illustrate steps of the present invention. Steps shown in FIG. 13 include the following. (1) Process: FFPE slide mounted tissue is incubated with a cocktail of primary antibodies conjugated to DNA oligos via a photo-cleavable linker, together with a limited number of visible-wavelength imaging reagents. (2) View: Regions of interest (ROI) are identified with visible-light based imaging reagents at low-plex to establish overall "architecture" of tumor slice (e.g., image nuclei and/or using one or two key tumor biomarkers). (3) Profile: Select ROIs are chosen for high-resolution multiplex profiling and oligos from the selected region are released following exposure to UV light. (4) Plating: Free photocleaved oligos are then collected, e.g., via a microcapillary-based "sipper", and stored in a microplate well for subsequent quantitation. (5) Digitally Count: During the digital counting step, photo-cleaved oligos from the spatially resolved ROIs in the microplate are hybridized to 4-color, 6-spot optical barcodes, enabling up to ~1 million digital counts of the protein targets (distributed over up to 800-plex markers) in a single ROI using standard NanoString nCounter® read-out instrument (e.g., SPRINT, Flex, and MAX).

A region of interest may be a tissue type present in a sample, a cell type, a cell, or a subcellular structure within a cell.

A composition comprising a set of probes, each probe comprising a releasable signal oligonucleotide, is applied to the serial section. The set of probes or may include probes that target proteins, target nucleic acids, or both. The composition may include capture probes. When probes indirectly bind to a target (protein and/or nucleic acid), the applied composition includes intermediary oligonucleotides. The composition will include other reagents known in the art to facilitate binding of a protein and/or a nucleic acid in a sample.

Blocking steps are performed before and/or after the composition is applied.

Figure 9:
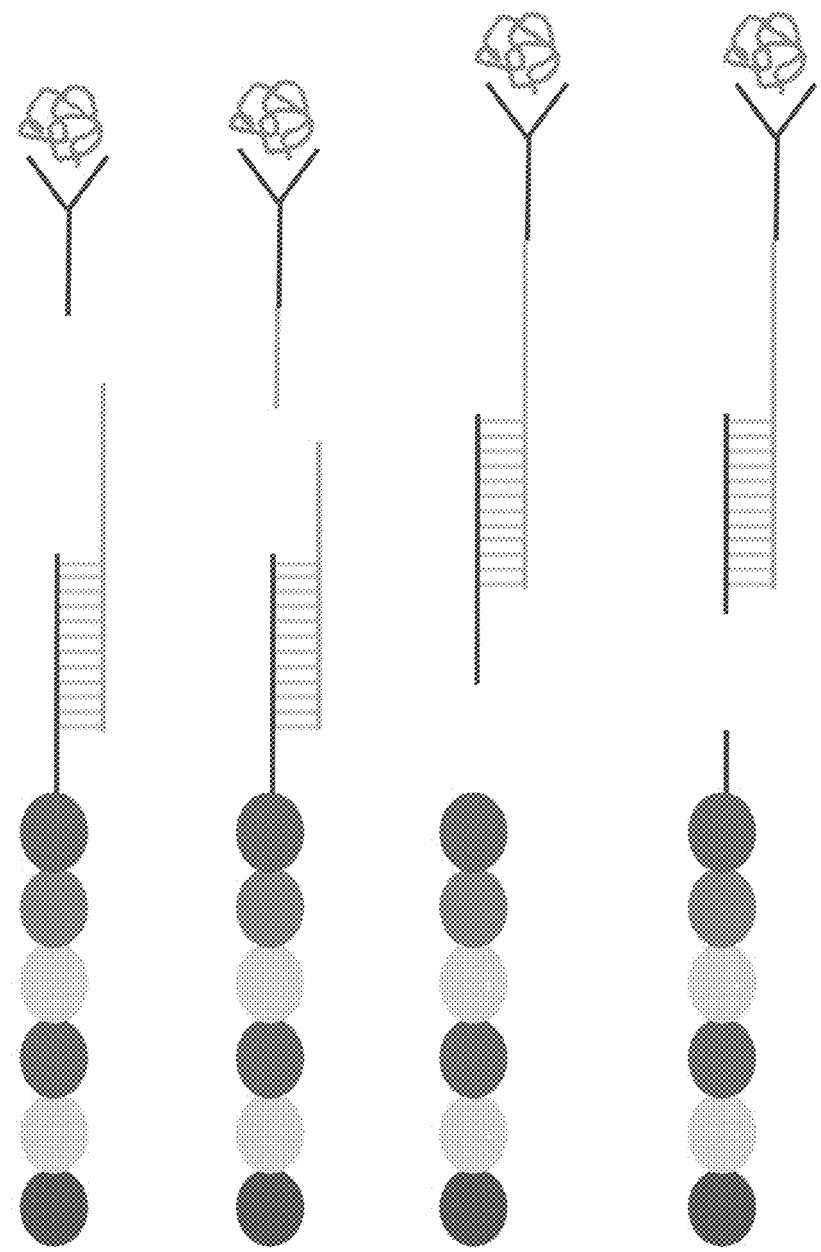
FIG. 9 shows release of signal oligonucleotides from a probe of the middle configuration shown in FIG. 7 and the probes of FIG. 8. The location of a cleavable motif within a probe (or in a reporter probe) affects which material is included with a released signal oligonucleotide.

For probes including photo-cleavable linkers, the solid support (e.g., microscope slide) is placed in a microscope that is capable of providing excitation light at a wavelength capable of cleaving the photo-cleavable linker. A first region-of-interest (red line in panel B in FIG. 10 and $ROI_i$ in FIGS. 11 and 12) is excited with the light, thereby cleaving the photo-cleavable linker and releasing the signal oligonucleotides. As illustrated in FIGS. 6 and 9, a signal oligonucleotide includes at least a region of a probe that presently has positions bound with at least one labeled oligonucleotide or the nucleic acid from a probe that is bound or can be bound by a reporter probe. By directing excitation light only to ROIi, signal oligonucleotides are only released from probes within ROIi and not from probes located outside of ROIi, which retain their signal oligonucleotides. Thus, signal oligonucleotides are collected only for probes that are bound to targets within ROIi, thereby permitting detection of the identities and quantities of the targets (proteins and/or nucleic acids) located within ROIi.

Figure 12:
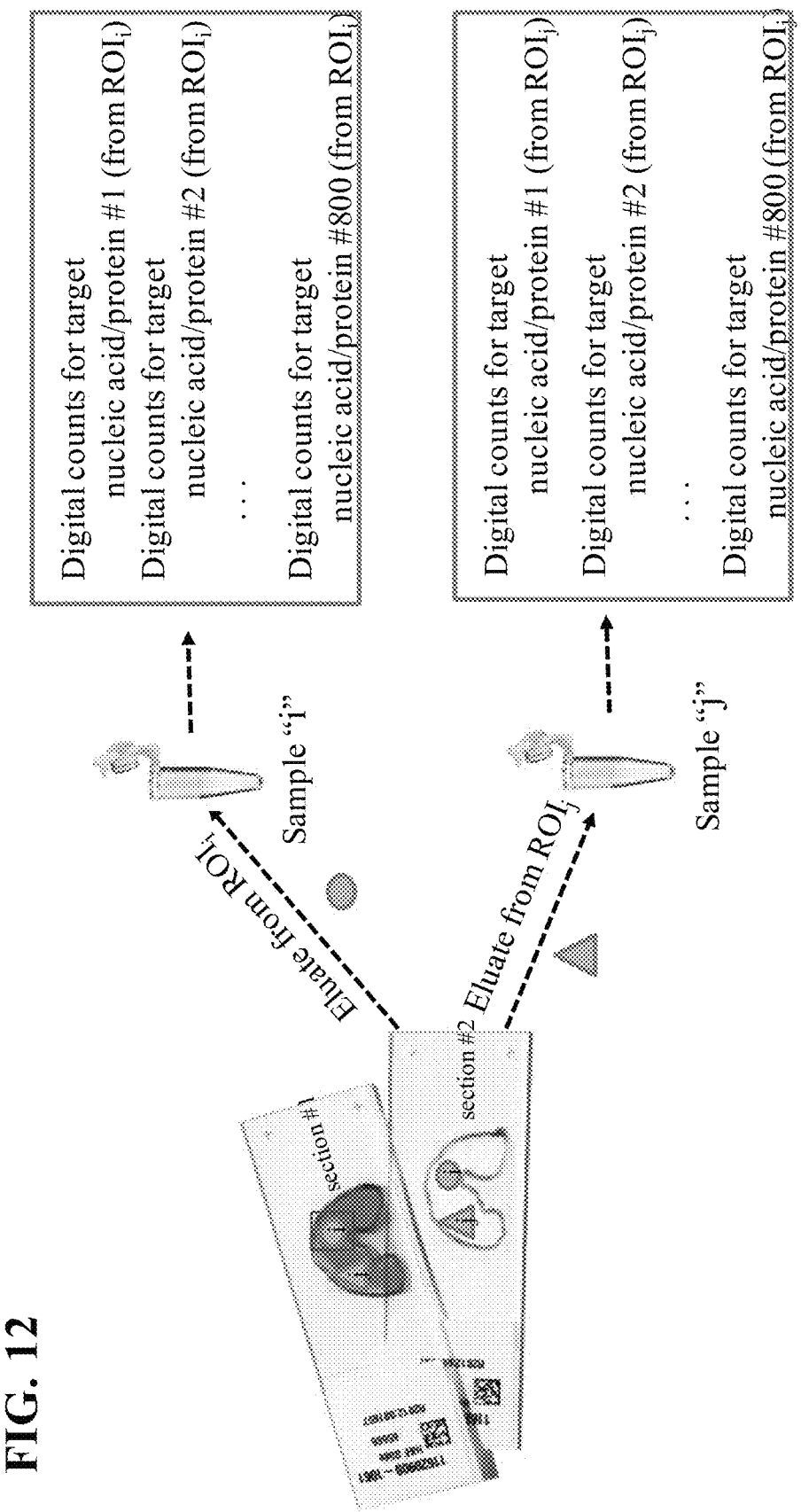
FIG. 12 shows multiplexed detection of a plurality of target nucleic acids and/or proteins from a first region-of-interest followed by multiplexed detection of the plurality of target nucleic acids and/or proteins from a second region-of-interest.

The surface of the section is washed with small amount of buffer (~5 to 30 µl) and the eluate (containing the released signal oligonucleotides) is collected into a first sample container (shown as Sample "i" in FIG. 12). The surface of the section is further rinsed to remove any released signal oligonucleotides that were omitted from the eluate.

A second region-of-interest ($ROI_j$ in FIGS. 11 and 12) is excited with light, thereby cleaving the photo-cleavable linker and releasing the signal oligonucleotides from the second region-of-interest. Again, by directing excitation light only to ROIj, signal oligonucleotides are only released from probes within ROIj and not from probes located outside of ROIj, which retain their signal oligonucleotides. Thus, signal oligonucleotides are collected only for probes that are bound to targets within ROIj, thereby permitting detection of the identities and quantities of the targets (proteins and/or nucleic acids) located within ROIj.

The surface of the section is washed with small amount of buffer (~5 to 30 µl) and the eluate (containing the released signal oligonucleotides) is collected into a first sample tube (shown as Sample "j" in FIG. 12). The surface of the section is further rinsed to remove any released signal oligonucleotides that were omitted from the eluate.

The excitation step, washing step, and rinsing step are repeated until signal oligonucleotides from all regions-of-interest (up to $ROI_n$) have been collected.

Additional advantages, features, and embodiments of the present invention are illustrated in the Appendix filed herewith. As examples, various methods and devices for collecting a signal oligonucleotide and various ways of providing a force are shown. Moreover, the Appendix provides unexpectedly improved results obtained from certain embodiments of the present invention over other embodiments.

Data demonstrating about 7-fold to about 200-fold signal-to-noise improvements are shown.

Figure 15:
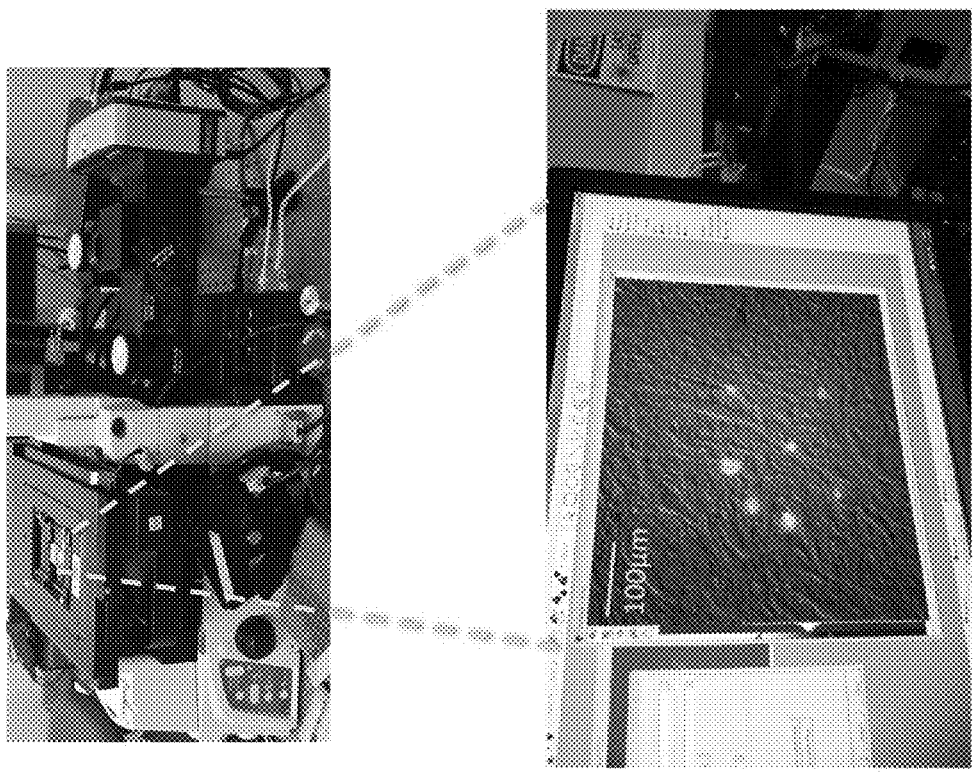
FIG. 15 are photographs showing a digital mirror device (DMD) attached to a Ti-E microscope (top) and a brightfield image of a FFPE tissue section (bottom). Light illumination (white spots) on the FFPE tissue (bright field image) shows multiple ROIs of about ~10-20 µm in size, i.e., the size of a single cell.
Figure 16:
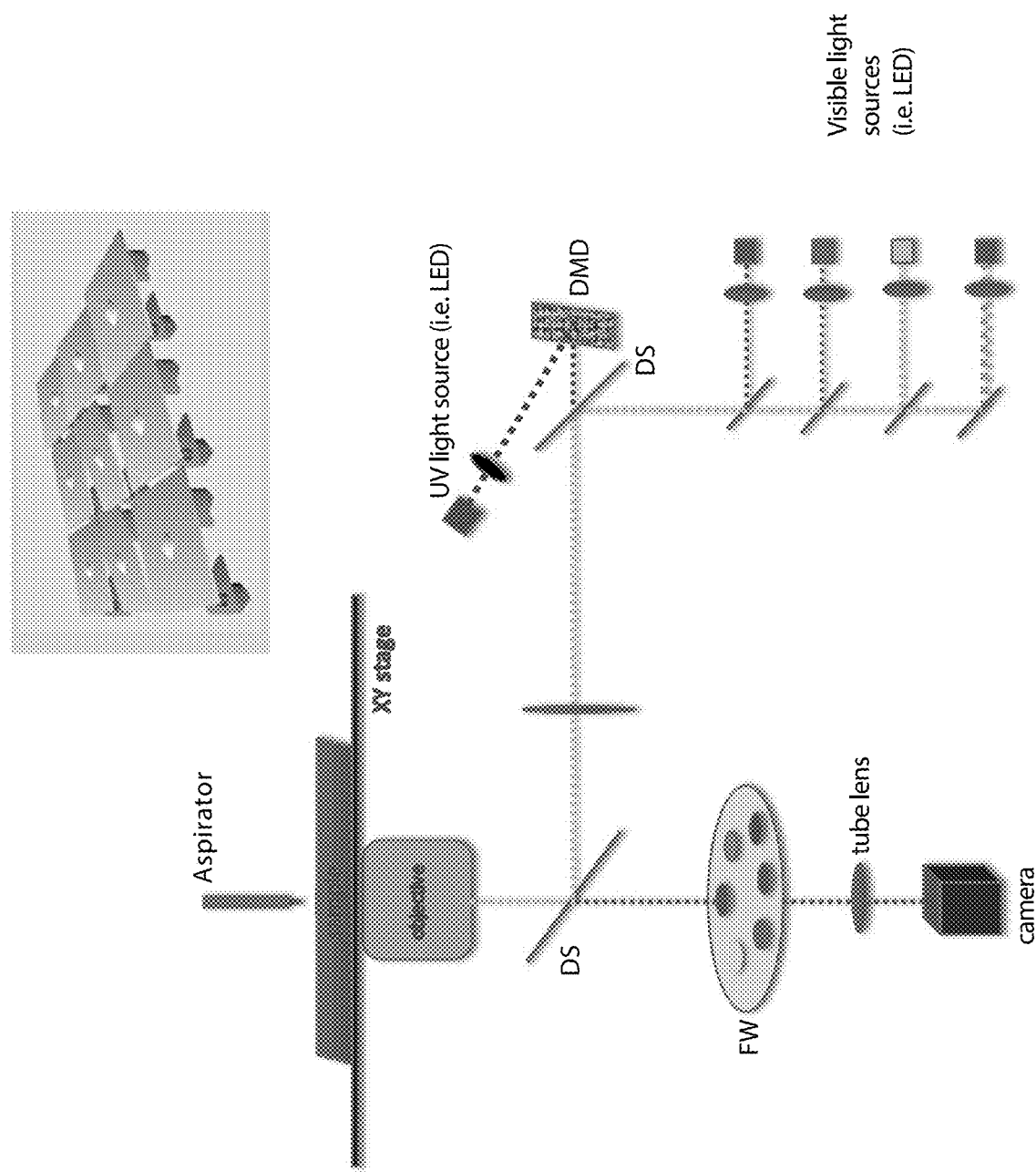
FIG. 16 illustrates components and light paths involved with the present invention when the method includes use of a digital mirror device (DMD). Wide-field illumination with the DMD focused onto sample. LED provides sufficient illumination to excite whole field of view at once and with single cell illumination such that ~80-600 DMD pixels illuminate a 10 µm diameter cell. A normal-grade DMD will provide sufficient single-cell resolution. DS: Dichroic mirror, FW: Filter wheel, and DMD: Digital mirror device.
Figure 17:
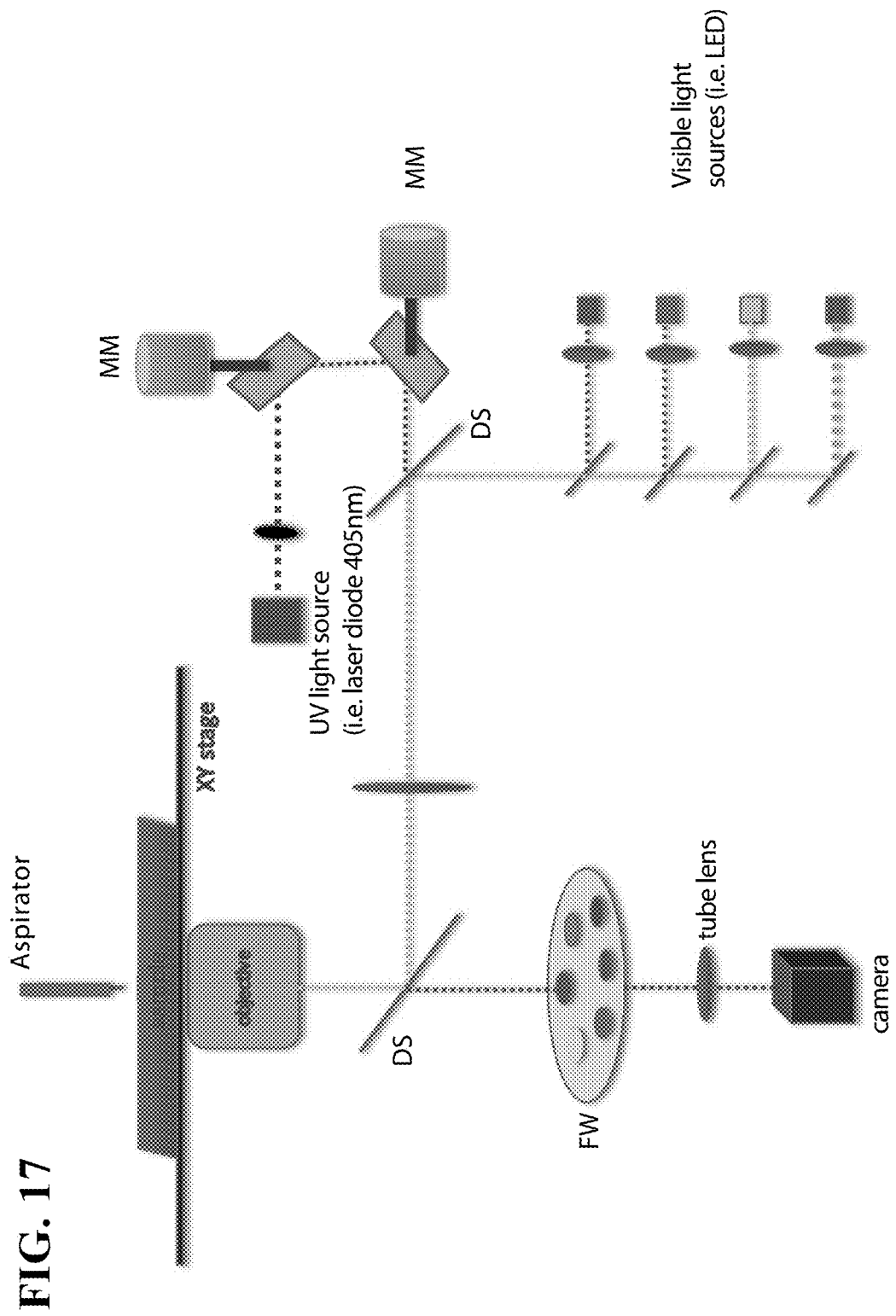
FIG. 17 illustrates components and light paths involved with the present invention when the method includes use of a laser scanning device (e.g., confocal scanning device). In a confocal scanning configuration, galvo-mirrors direct light. This method requires an inexpensive 405 nm laser. DS: Dichroic mirror, FW: Filter wheel, and MM: Motorized mirror.

Detection can use any microscope-type device or system known in the art. A device or system may include wide field illumination along with a digital mirror device (DMD; see FIGS. 15 and 16); advantages of this include reduced costs since the DMD and controller can also drive the LED (which photocleaves probes) and adds essentially no additional cost, provides ease of implementation, allows small feature size of ~1 mm which will include 10-40 mm cells, and leverages available consumer electronics (like projectors). A device or system may include a laser scanning device, e.g., confocal, see FIG. 16. An advantage of this is smaller morphological features can be illuminated and imaged; however, additional costs are involved with these devices.

The plurality of target proteins and/or target nucleic acids present in each region of interest in a sample are identified in each eluate sample using a polymerase reaction, a reverse transcriptase reaction, hybridization to an oligonucleotide microarray, mass spectrometry, hybridization to a fluorescent molecular beacon, a sequencing reaction, or nCounter® Molecular Barcodes. nCounter® systems and methods from NanoString Technologies®, as described in US2003/0013091, US2007/0166708, US2010/0015607, US2010/0261026, US2010/0262374, US2010/0112710, US2010/0047924, US2014/0371088, and US2011/0086774), are a preferred means for identifying target proteins and/or target nucleic acids. nCounter® systems and methods from NanoString Technologies® allow simultaneous multiplexed identification a plurality (800 or more) distinct target proteins and/or target nucleic acids.

Together, a comparison of the identity and abundance of the target proteins and/or target nucleic acids present in first region of interest (e.g., tissue type, a cell type (including normal and abnormal cells), and a subcellular structure within a cell) and the identity and abundance of the target proteins and/or target nucleic acids present in second region of interest or more regions of interest can be made.

The present invention provides multiplexed detection and comparison of up to 800 proteins of interest from discrete regions within a tumor (for example) and its adjacent normal tissue; thus, enabling systematic interrogation of the tumor and its microenvironment.

The present invention can be used in ongoing clinical studies to elucidate novel responses to immunotherapies and other targeted therapies.

The present invention also enables the discovery of immune biomarkers in tumors (for example) which can be used in the development of companion diagnostics.

Immunohistochemistry is a powerful technique for analyzing protein expression and localization in FFPE tissue sections. However, it suffers from a number of challenges, including a lack of dynamic range, difficult quantitation, and labor intensive workflow for very limited multiplexing. Here is disclosed a novel platform based on the nCounter® barcoding technology which enables spatially-resolved, digital characterization of proteins in a highly multiplexed (up to 800-plex) assay, i.e., the nCounter® Digital Multiplexed Immunohistochemistry (IHC) assay. The assay relies upon antibodies coupled to photo-cleavable oligonucleotide tags which are released from discrete regions of a tissue using focused through-objective UV (e.g., ~365 nm) exposure. Cleaved tags are quantitated in an nCounter® assay and counts mapped back to tissue location, yielding a spatially-resolved digital profile of protein abundance. The protein-detection may be performed along with or separate from a nucleic acid-detection assay which uses nucleic acid probes comprising photo-cleavable oligonucleotide tags. Thus, the present invention can provide spatially-resolved digital profile of protein abundance, spatially-resolved digital profile of protein and nucleic acid abundance, or spatially-resolved digital profile of nucleic acid abundance.

Advantages of the assay include, but are not limited to: high sensitivity (e.g., ~1 to 4 cells), all digital counting, with large dynamic range (>$10^5$), highly multiplexed (e.g., 30 targets and scalable, with no change in instrumentation, to 800 targets), simple workflow, compatibility with FFPE, no secondary antibodies (for protein detection) or amplification reagents, and potential for clinical assays.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless defined otherwise, all technical and scientific terms used herein have the same meaning as commonly understood by one of ordinary skill in the art to which the invention pertains. Although other probes, compositions, methods, and kits similar, or equivalent, to those described herein can be used in the practice of the present invention, the preferred materials and methods are described herein. It is to be understood that the terminology used herein is for the purpose of describing particular embodiments only, and is not intended to be limiting.

EXAMPLES

Example 1: The Present Invention Provides a "Barcoding-Potential" to Quantify Multiplexed Targets in a FFPE Tissue Section Intratumoral heterogeneity has emerged as a critical challenge to the implementation of targeted therapeutics. Historically, immunohistochemistry (IHC) has been used to assess spatial heterogeneity of proteins; however, it has been difficult to quantify protein abundance at high multiplex and wide dynamic range.

In this example, proteins in a formalin-fixed paraffin embedded (FFPE) tissue section were labeled with antibody-comprising probes that included photo-cleavable linkers and fluorescent barcodes. The probes—in a user-defined ROI of the FFPE tissue section—were subsequently exposed to focused UV light, thereby releasing the signal oligonucleotides (comprising the fluorescent barcodes) from the ROI. The released signal oligonucleotides were washed away from the FFPE sample and collected. The fluorescent barcodes from the released signal oligonucleotides were then recognized and digitally counted by an nCounter® system from NanoString Technologies®, thereby quantifying the abundance of each targeted protein in the user-defined spatial region of a tissue section. After the signal oligonucleotides from a first ROI were released and collected, the focused UV light was exposed to a second user-defined ROI of the FFPE tissue section, thereby releasing the signal oligonucleotides from the second ROI. In this non-limiting example, a high degree of linearity (0.97<$R^2$<0.99) for the number of observed counts versus area of UV illumination was observed and with a detection spatial resolution of about 100 µm×100 µm, or approximately 100 cells. Unexpectedly, the present invention provides a "barcoding-potential" to quantify up to 800 targets with 5.5 logarithms (base 10) of dynamic range in a single FFPE tissue section.

Example 2: The Present Invention Provides a Practical and Feasible Approach for Quantifying Protein Expression without Signal Amplification and for Achieving Higher-Order Target Antigen Multiplexing in a FFPE Tissue Section Quantitative, multiplexed immunohistochemistry has emerged as an area of great interest within oncology since it has the unique capability of identifying spatiotemporal organization and interdependencies that further define how checkpoint blockade impacts tumor microenvironment. This example describes a one-step, amplification-free staining method using a photo-cleavable oligo-tagged primary antibody which interacts with the target antigen within an FFPE tissue section. Illumination with ultraviolet (UV) light is applied which releases the oligo from the antibody and is followed by eluent collection, quantification, and digital counting that corresponds to antigen abundance.

First was investigated a variety of conjugation methods; this established a cysteine bioconjugation method that is stable, site-specific to predominantly the hinge-region heavy-chain, and relatively controllable in terms of oligonucleotide to antibody stoichiometric ratios.

Next was performed a linear regression analysis to determine the relationship between UV-induced cleavage area and measured digital protein counts; from this was observed a high degree of linearity (0.97<$R^2$<0.99), confirming the basic mechanism/premise associated with this multiplexed protein counting method on FFPE tissue.

To determine the impact of the presence of a conjugated oligonucleotide on antibody-antigen interaction, the performance of a labeled oligonucleotides-conjugated antibody to the unmodified antibody under identical conditions in FFPE tissue sections was compared in terms of sensitivity, specificity and signal intensity. Antibodies were selected that targeted antigens localized to the nucleus, cytoplasm, or membrane to determine the relationship between antibody performance and subcellular location of target antigens. Selected antibodies targeted Foxp3, Histone H3, P-S6 (nuclear antigens), CD3, CD4, PD-1, CD45RO (cytoplasmic antigens), and PD-L1 (membranous antigen). In terms of sensitivity, generally, "heavier" oligonucleotide-conjugated antibodies (having 3 or 4 labeled oligonucleotide per antibody) were found to be significantly less sensitive when compared to unconjugated antibodies or "lighter" oligonucleotide-conjugated antibodies (having 1 or 2 labeled oligonucleotide per antibody). No significant difference was observed between unconjugated or "lighter" oligonucleotide-conjugated antibodies in terms of sensitivity, specificity, or intensity across nuclear, cytoplasmic and membranous target antigens.

The present invention provides highly multiplexed protein profiling that measures absolute protein expression levels using practical and feasible methods to comprehensively define the immune landscape in tumors before and during immunotherapeutic intervention.

Example 3: The Present Invention Provides Spatially-Resolved, Multiplexed Protein Detection from FFPE Tissue Methods Antibodies—Antibodies used in this Example and Examples 4 to 6 may include: "target (clone ID, vendor))": H3 (D1H2, CST), CD8 (OTI3H6, Origene), CD4 (SP35, Spring Bio), FOXP3 (D2W8E, CST), B7-H3 (D9M2L, CST), S6 (54D2, CST), B7-H4 (D1M8I, CST), Granzyme B (OTI4E4, Origene), Ki67 (8D5, CST), PD-1 (Nat105, Cell Marque), CD3 (MRQ-39, Cell Marque), Vista (D1L2G, CST), Her2 (29D8, CST), PR (D8Q2J, CST), ER (SP1, Spring Bio), EGFR (D38B1, CST), CD56 (MRQ-42, Cell Marque), PD-L1 (E1L3N, CST), CD45 (2B11&PD7/26, Cell Marque), TIM-3 (D5D5R, CST), and Pan Keratin (C11, CST), CD45RO (UCHL1, Cell Marque).

Tonsil Microscopy—5 µm sections of a tonsil FFPE block (Amsbio) were mounted on slides. IHC was performed using standard protocols. Antigen retrieval was performed with a pressure cooker. Staining of the tonsil section was performed with CD3 primary antibody MRQ-39 (Rabbit mAb, Cell Marque) and Ki-67 primary antibody 8D5 (Mouse mAb, CST). Secondary incubations were performed with Alexa594 labeled Goat α Rabbit (Life Tech.) and Alexa488 labeled Goat α Mouse (Life Tech.)

Here, samples attached to a slide were first imaged using fluorescent antibodies and then expression of proteins was digitally counted from the sample.

Steps similar to those illustrated in FIG. 10 to FIG. 14 (top) were used. UV-cleavage of selected ROIs allowed full 30-plex digital profiling (nCounter® counts).

Results

Figure 18:
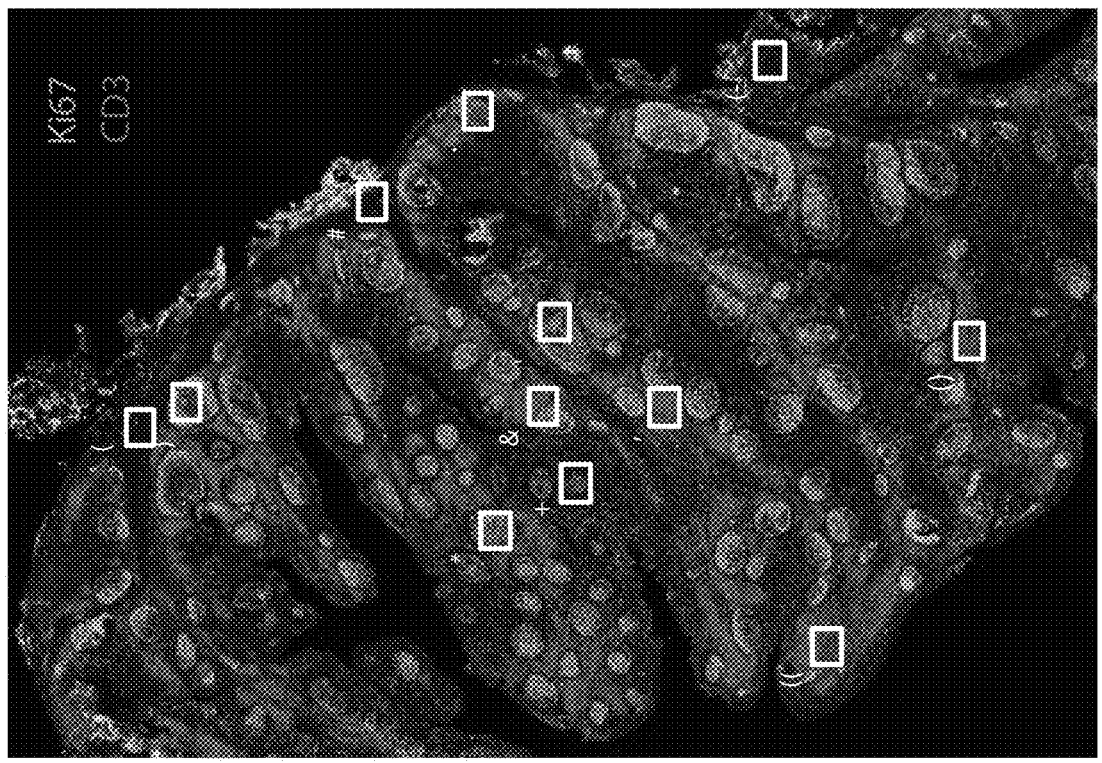
FIG. 18 shows a photomicrograph establishing overall tissue morphology of a tonsil sample that was initially imaged using two-color fluorescence of Ki-67 (cell proliferation marker; in green) and CD3 (immune cell marker; in red). Twelve regions (including the four regions magnified in FIG. 19) are identified with white boxes.
Figure 19:
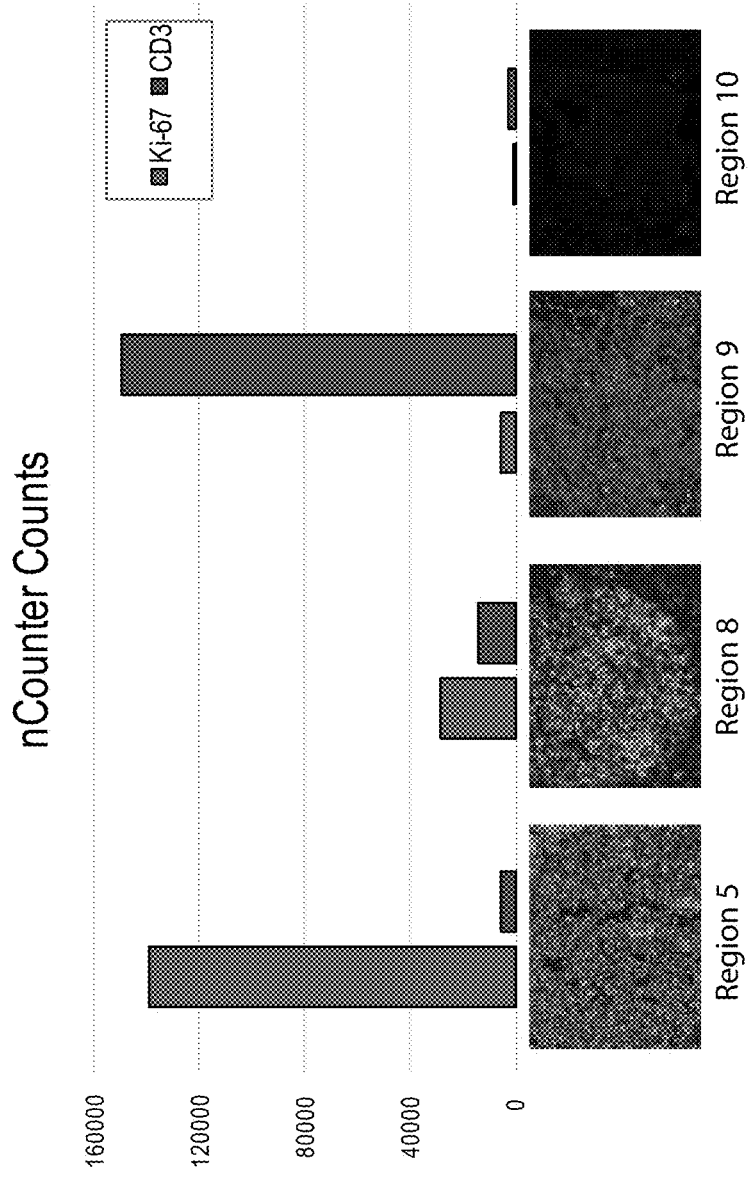
FIG. 19 is a graph showing nCounter® data counts of Ki-67 and CD3 for four regions shown in FIG. 18. Images were obtained from serial sections (to allow various additional controls to be examined). In general, samples can be imaged with fluorescent antibodies and then digitally counted (via uv-exposure) using the same slide. Multiple targets analyzed across twelve regions (including the four regions shown here) show distinct profiles of localization of Ki-67 and CD3. Below the graph are magnifications of the four regions.
Figure 20:
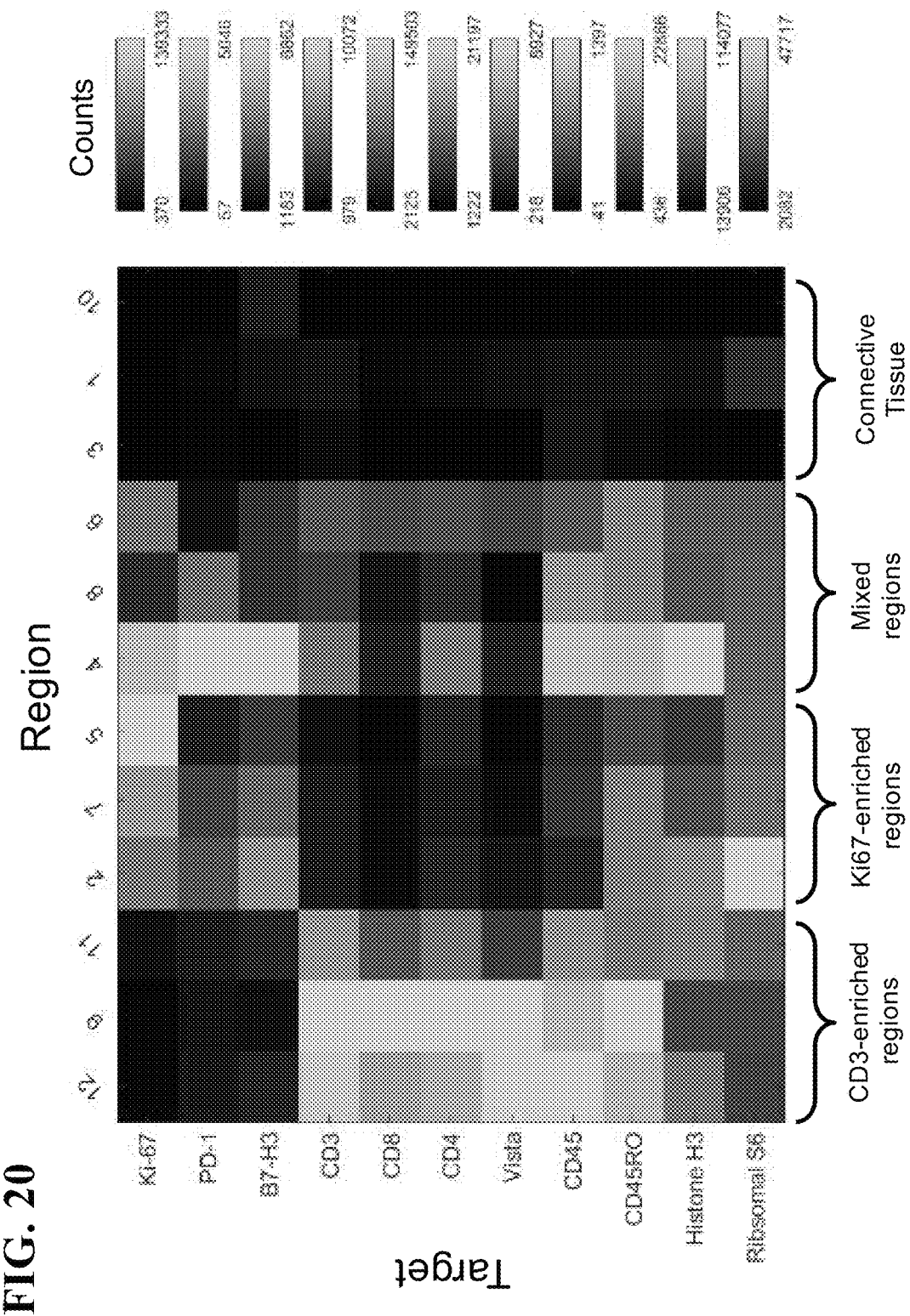
FIG. 20 shows exemplary counts from a 30-plex oligoantibody cocktail on the twelve regions of interest (ROI) from the tonsil sample shown in FIG. 18. Data was obtained from serial sections (to allow various additional controls to be examined).

FIG. 18 shows a photomicrograph establishing overall tissue morphology of a tonsil sample that was initially imaged using 2-color fluorescence of Ki-67 (cell proliferation marker; in green) and CD3 (immune cell marker; in red). Multiple targets analyzed across twelve regions (including the four regions magnified in FIG. 19) show three distinct profiles of Ki-67 and CD3 localization. FIG. 19 shows nCounter® counts for Ki-67 and CD3 for four regions shown in FIG. 18. FIG. 20 shows exemplary counts from a 30-plex oligo-antibody cocktail on the twelve regions of interest (ROI) from the tonsil sample shown in FIG. 18. Data was obtained from serial sections (to allow various additional controls to be examined). As shown, regions of the tissue sample can be classified based on the intensity and identity of the markers expressed. Exemplary classifications shown: "CD3-enriched", "Ki67-enriched", "Mixed", and "Connective tissue".

These data show that the present invention provides spatially-resolved detection of a plurality (here, at least 30) of protein markers. By scaling up the number of protein probes (antibodies) used, up to 800 different protein markers can be detected and with similar resolution.

Example 4: The Present Invention Provides Multiplexed Protein Detection from FFPE Tissue and Approaching Single-Cell Resolution Methods Melanoma Microscopy—5 µm sections of a melanoma (lymph node derived) FFPE block (Asterand) were mounted on slides. IHC was performed using standard protocols. Antigen retrieval was performed with a pressure cooker.

Here, samples were first imaged using fluorescence and then expression of proteins was digitally counted from the sample.

Steps similar to those illustrated in FIG. 10 to FIG. 14 (top) were used.

Results

Figure 21:
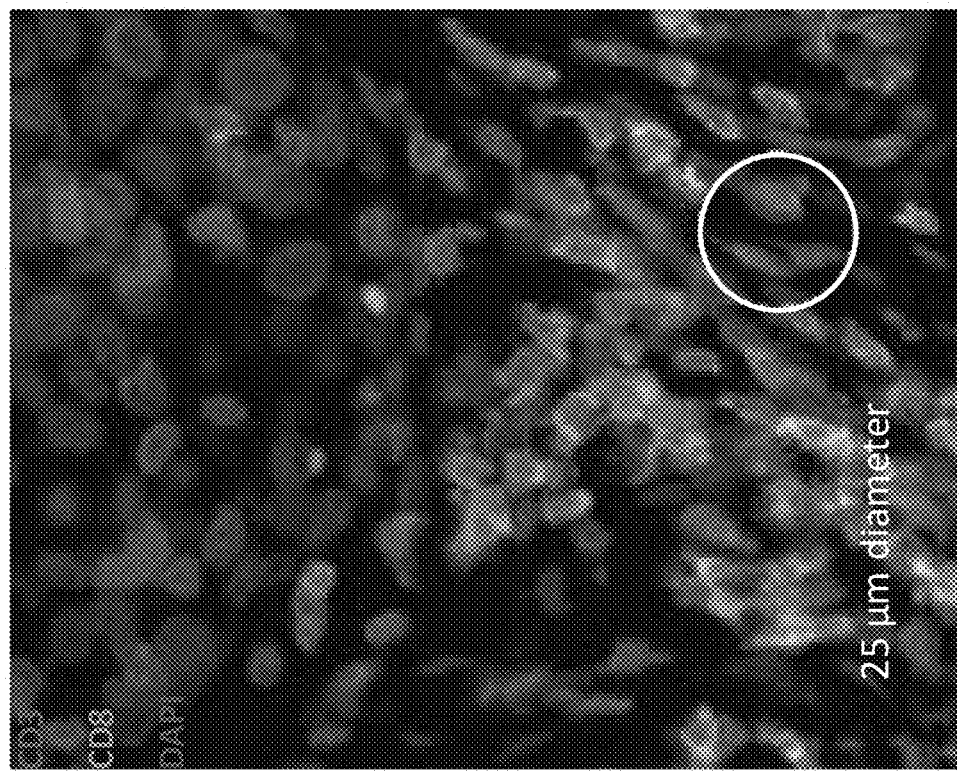
FIG. 21 shows a photomicrograph establishing overall tissue morphology of T cells in a melanoma sample from a lymph node that was initially imaged using three-color fluorescence of CD3 (in red), CD8 (in green), and DAPI (in blue). The white circle is 25 µm in diameter and surrounds three cells.

FIG. 21 shows a photomicrograph establishing overall tissue morphology of T cells in a melanoma sample of lymph node that was initially imaged using three-color fluorescence of CD3 (in red), CD8 (in green), and DAPI (in blue). The white circle is 25 μm in diameter and surrounds three cells.

Figure 22:
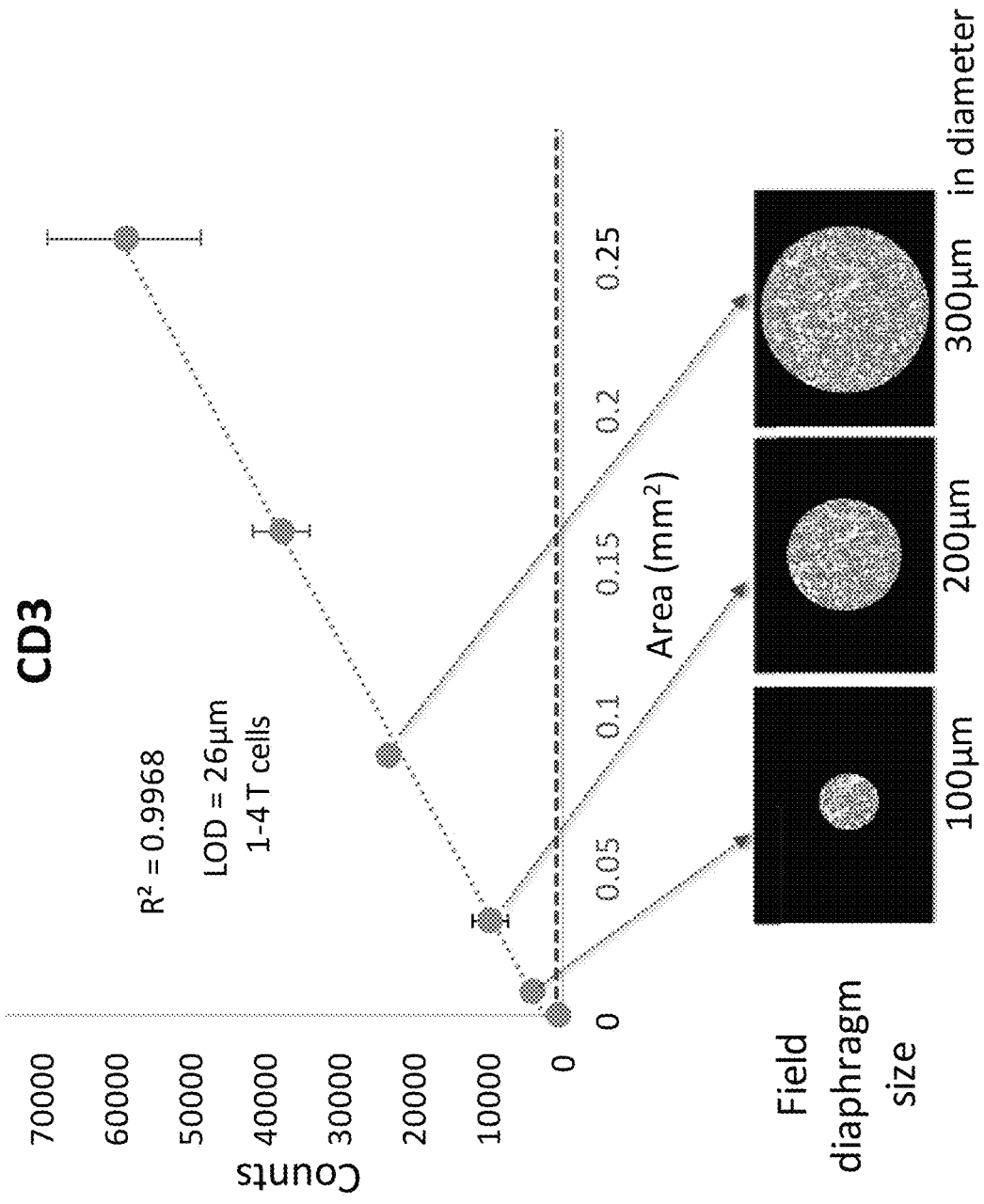
FIG. 22 shows nCounter® data of CD3 conjugate release from FFPE lymph node tissue sections (5 µm thickness) as a function of UV illumination area (100 µm to 1 mm in diameter). The field diaphragm size is shown below the figure.

FIG. 22 shows nCounter® data of CD3 conjugate release from FFPE lymph node tissue section (5 μm thickness) as a function of UV illumination area (100 μm to 1 mm in diameter). The limit of detection counts (LOD=background counts+2x standard deviation) corresponds to spatial resolution of 26 μm in diameter. The field diaphragm size is shown below the figure. FIG. 23 and FIG. 24 show data for CD45 and PD1 (respectively, from the same experiment).

The data shows a spatial detection ability of the present invention corresponding to about one to four cells.

Example 5: The Present Invention Provides Quantitative Performance in a Clinically-Relevant Assay Method Steps similar to those illustrated in FIG. 10 to FIG. 14 (top) were used.

Breast Cancer tissue microarray (TMA): TMA BR1504a obtained from US Biomax, Inc., H&E staining image obtained from US Biomax website (World Wide Web (www) biomax.ushissue-arrays/Breast/BR1504a). Section from the same block as the section shown on in the left panel of FIG. 25 were stained with Her2 primary antibody 29D8 (Rabbit mAb, CST), and Alexa594 labeled Goat α Rabbit (Life Tech.). Counts were also obtained for Histone H3, Ribsomal Protein S6, Estrogen Receptor, Progesterone Receptor, Mouse IgG isotype control, and Rabbit IgG isotype control (data not shown). Her2 pathologist scores for TMA BR1504a were provided by US Biomax, Inc. (World Wide Web (www) biomax.ushissue-arrays/Breast/BR1504a). Staining was performed with Her2 primary antibody 29D8 (Rabbit mAb, CST), and Alexa594 labeled Goat α Rabbit (Life Tech.). Although other Rabbit primary antibodies were used in the primary cocktail, fluorescence from these antibodies was negligible compared to Her2 fluorescence. Sum Pixel Intensities (at λ=594) were obtained using ImageJ software. For this, the background value was set to intensity=0 and the highest intensity was set to intensity=255. The summation of all pixel intensities per ROI is shown.

Here, samples were first imaged using fluorescence and then expression of proteins was digitally counted from the sample.

Results

Figure 25:
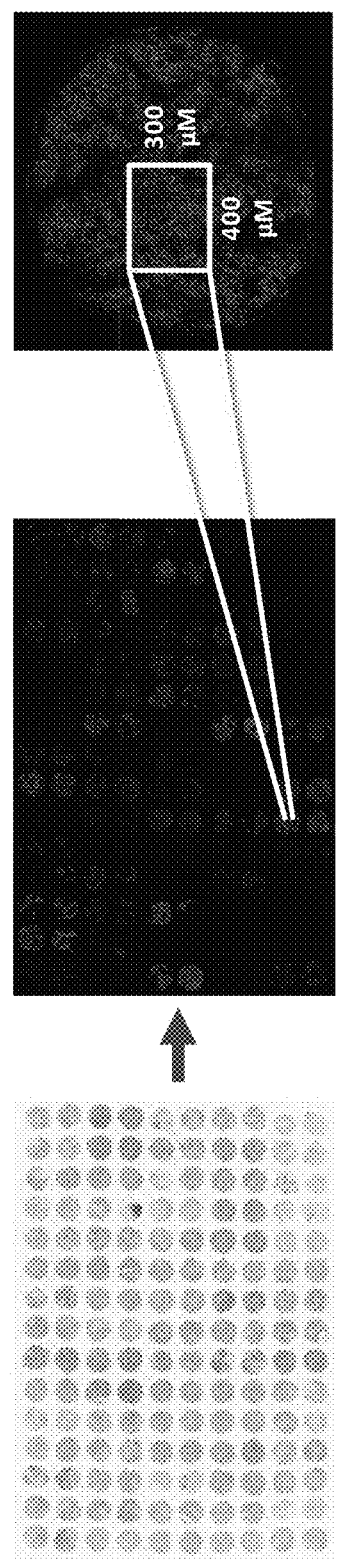
FIG. 25 shows a tissue microarray (TMA; left panel) of breast tumor tissue containing variable levels of Her2 protein as shown in the photomicrograph (center panel) which identifies Her2 fluorescence by IHC staining. The right panel shows a magnification of a single region of the central panel.

FIG. 25 (left panel) shows a tissue microarray (TMA) of breast tumor tissue containing variable levels of Her2 protein as shown in the photomicrograph (center panel) which identifies Her2 fluorescence by IHC staining. The right panel shows a magnification of a single region of the central panel; such regions were stained with a multiplexed antibody cocktail.

Figure 26:
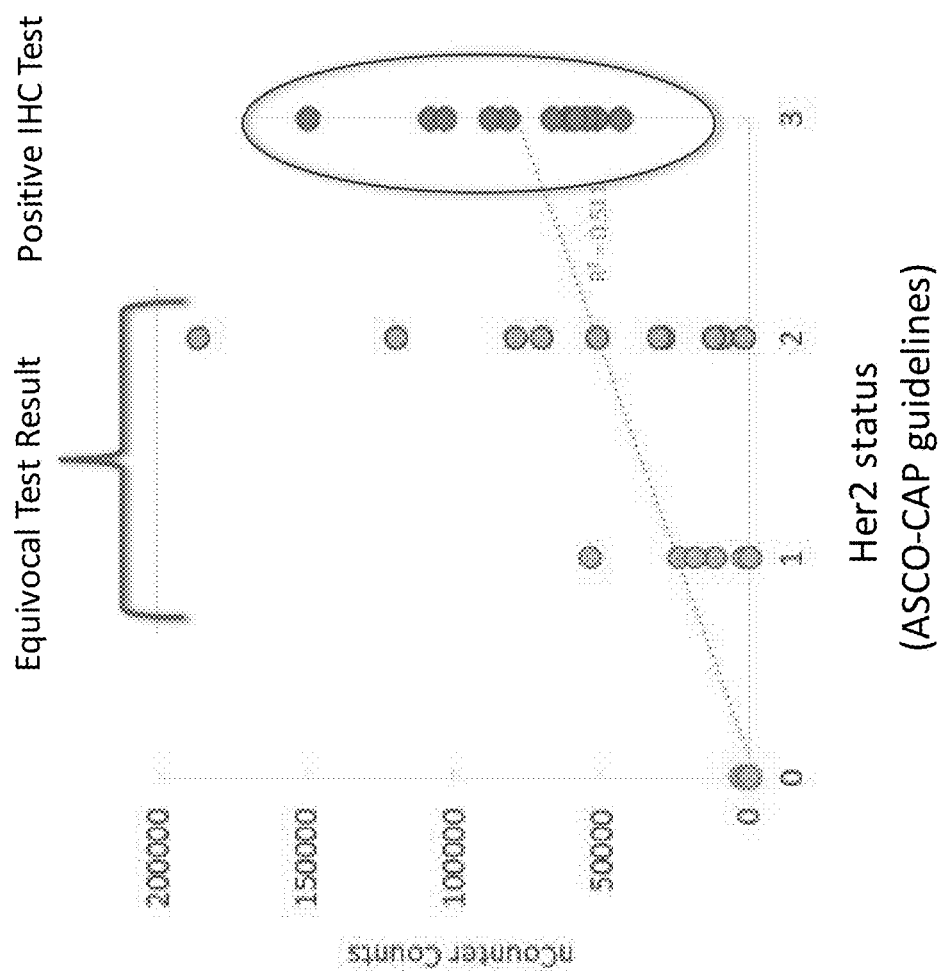
FIG. 26 shows nCounter® count data for forty-eight representative regions versus Her2 status (ASCO-CAP guidelines).
Figure 27:
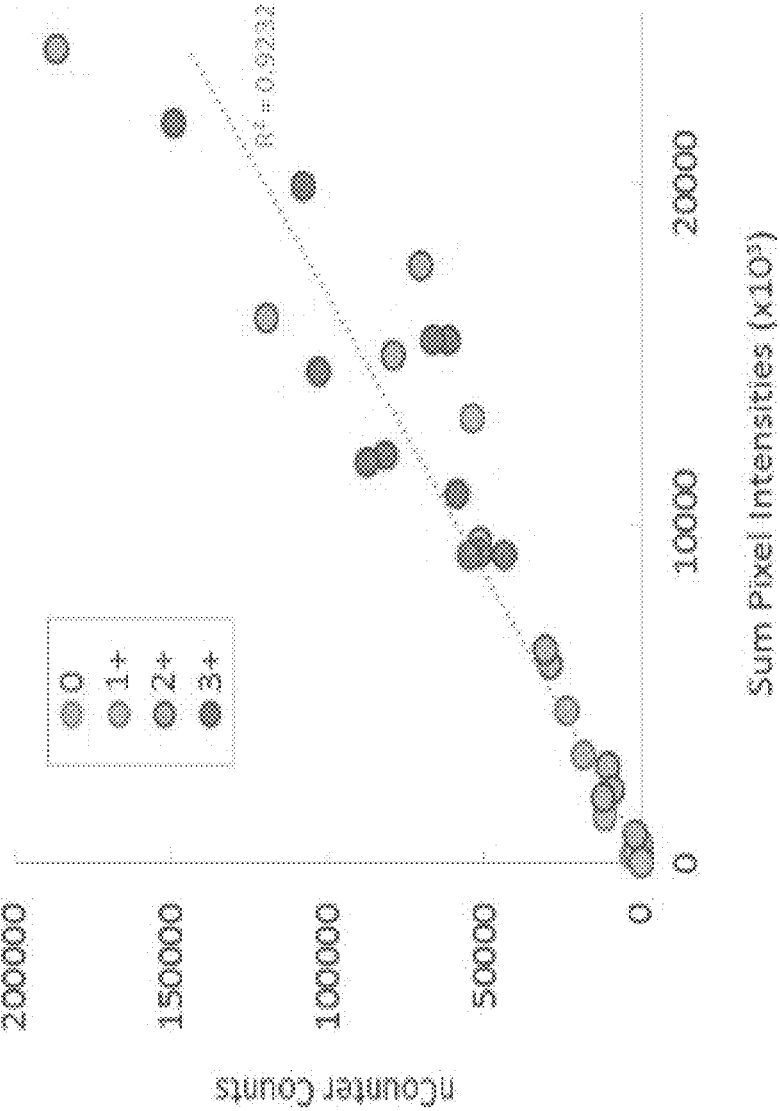
FIG. 27 shows Plots of nCounter® Counts versus Sum Pixel Intensities ($\times 10^3$) for the forty-eight regions mentioned with respect to FIG. 26.

FIG. 26 shows nCounter® count data for forty-eight representative regions versus Her2 status (ASCO-CAP guidelines). FIG. 27 plots nCounter® Counts versus Sum Pixel Intensities (×10³) for the forty-eight regions mentioned above.

These digital count data show a high correlation with fluorescence intensities (R2=0.92, FIG. 27) compared to visual Her2 status scoring via ASCO-CAP guidelines (R2=0.51, FIG. 26).

Example 6: The Present Invention Reveals Abundances of Specific Cell Types in a Tissue Sample Steps similar to those illustrated in FIG. 10 to FIG. 14 (top) were used; a melanoma sample attached to a slide was first imaged using fluorescence and then expression of proteins was digitally counted from the sample.

Figure 28:
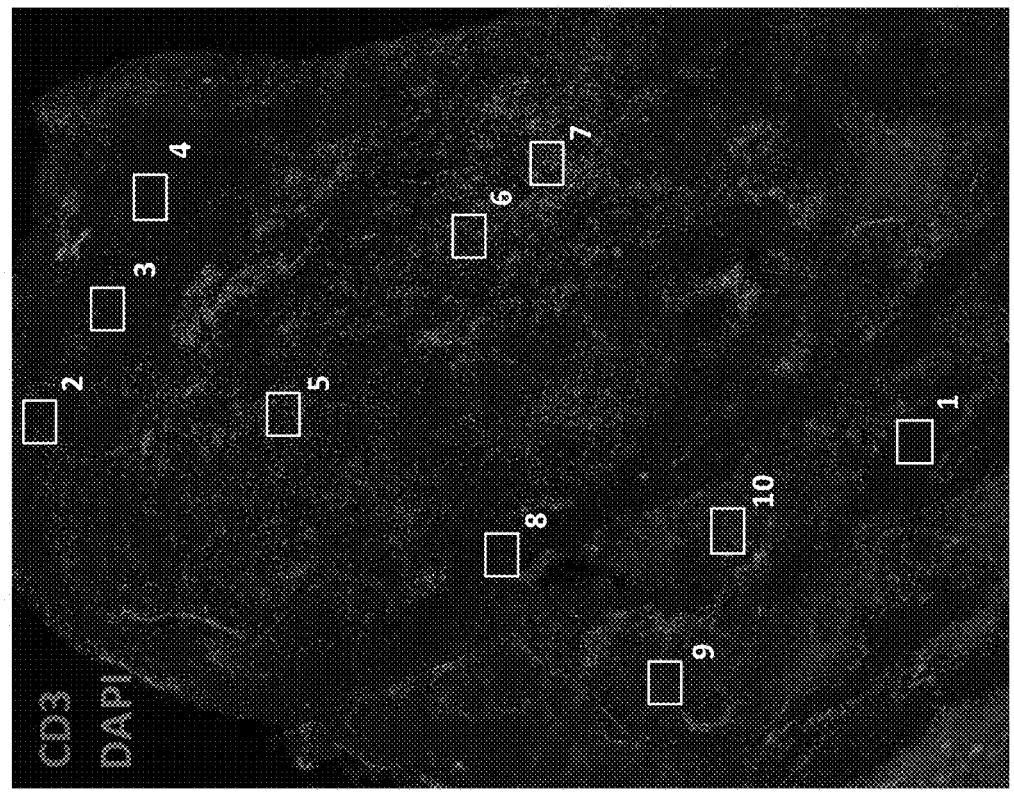
FIG. 28 is a photomicrograph establishing overall tissue morphology of a melanoma sample that was initially imaged using two-color fluorescence of CD3 (in red) and DAPI (in blue). Ten exemplary regions are identified with white boxes.
Figure 29:
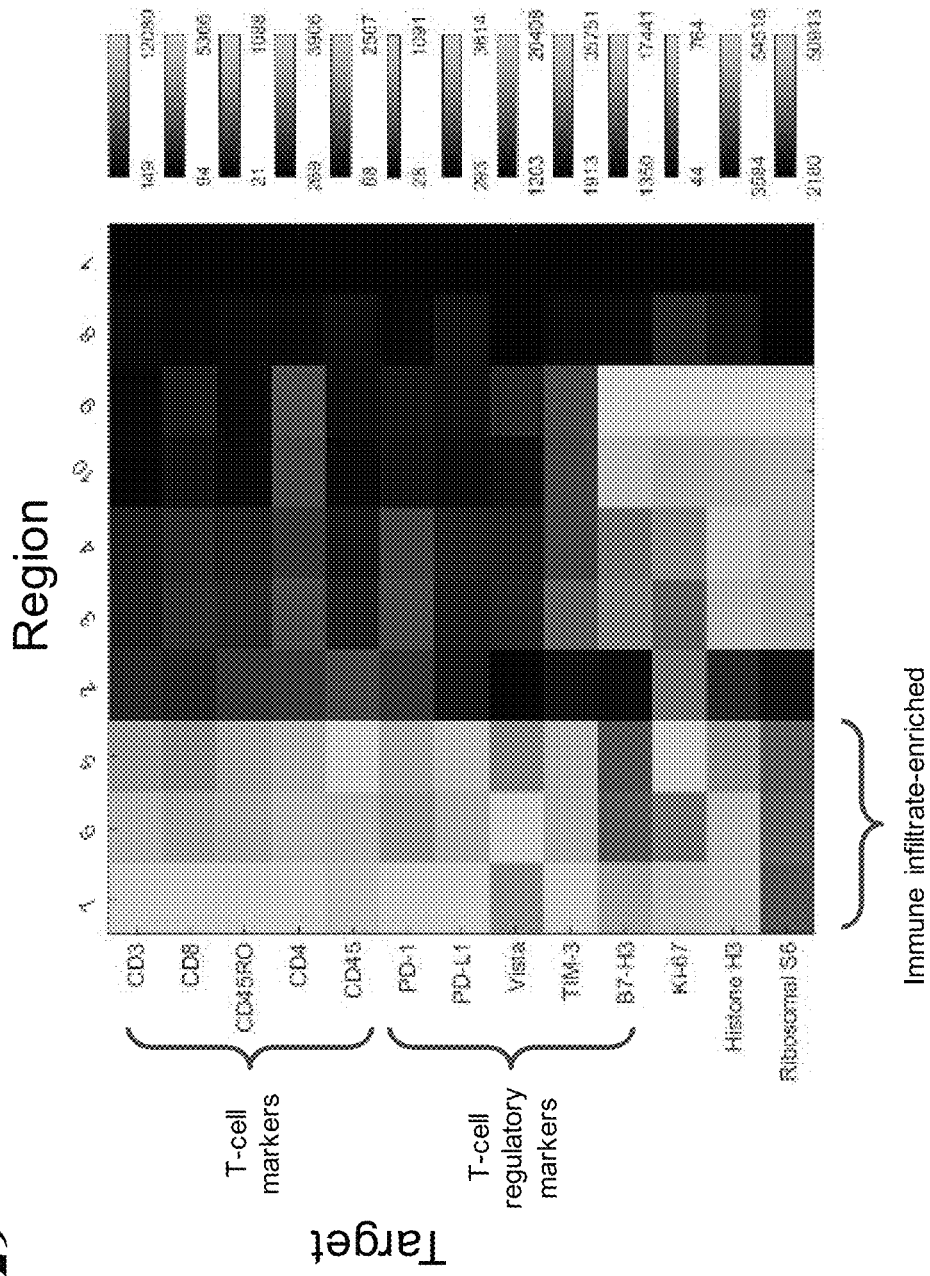
FIG. 29 shows exemplary counts from a 30-plex oligo-antibody cocktail on the ten regions of interest (ROI) from the sample shown in FIG. 28.

FIG. 28 shows a photomicrograph establishing overall tissue morphology of a melanoma sample using two-color fluorescence of CD3 (immune cell marker; in red) and DAPI (cell nuclei, in blue). Expression data using a 30 antibody cocktail was obtained from the ten regions identified with white boxes. FIG. 29 shows exemplary nCounter® counts from a 30-plex oligo-antibody cocktail on the ten regions of interest (ROI) from the melanoma sample shown in FIG. 28. Counts for thirteen markers, each having expression counts above background, are shown. Regions 5, 6, 7, identified as "Immune infiltrate-enriched" have the highest expression of T-cell markers and T-cell regulatory markers.

These data show that the present invention provides spatially-resolved detection of a plurality (here, at least 30) of protein markers. By scaling up the number of protein probes (antibodies) used, up to 800 different protein markers can be detected and with similar resolution.

Figure 30B:
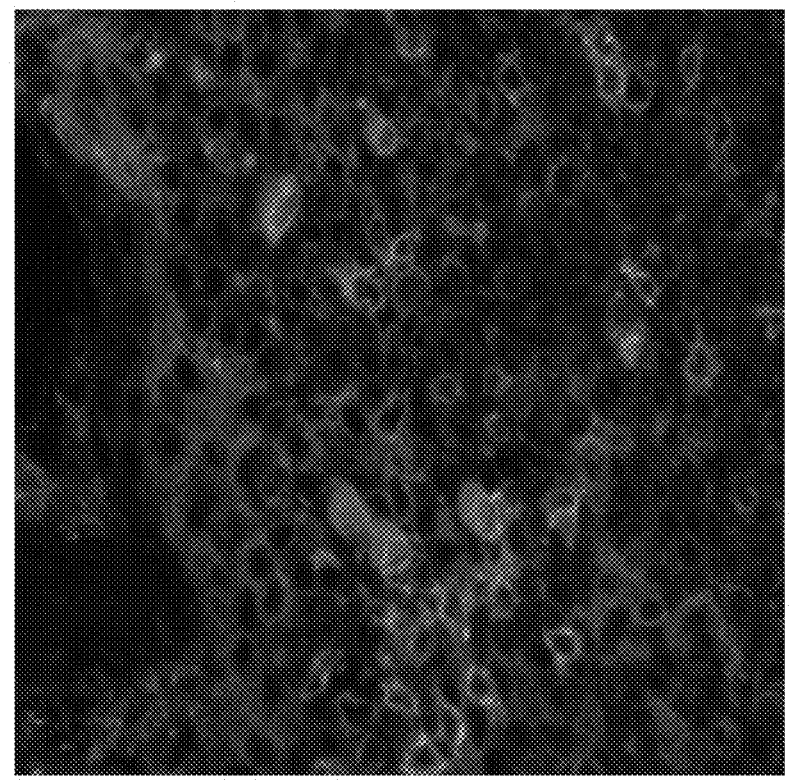
FIG. 30A and FIG. 30B are photomicrographs showing UV illumination using a digital mirror device (DMD) of single cells (in blue) in a tonsil tissue sample (in green).
Figure 30A:
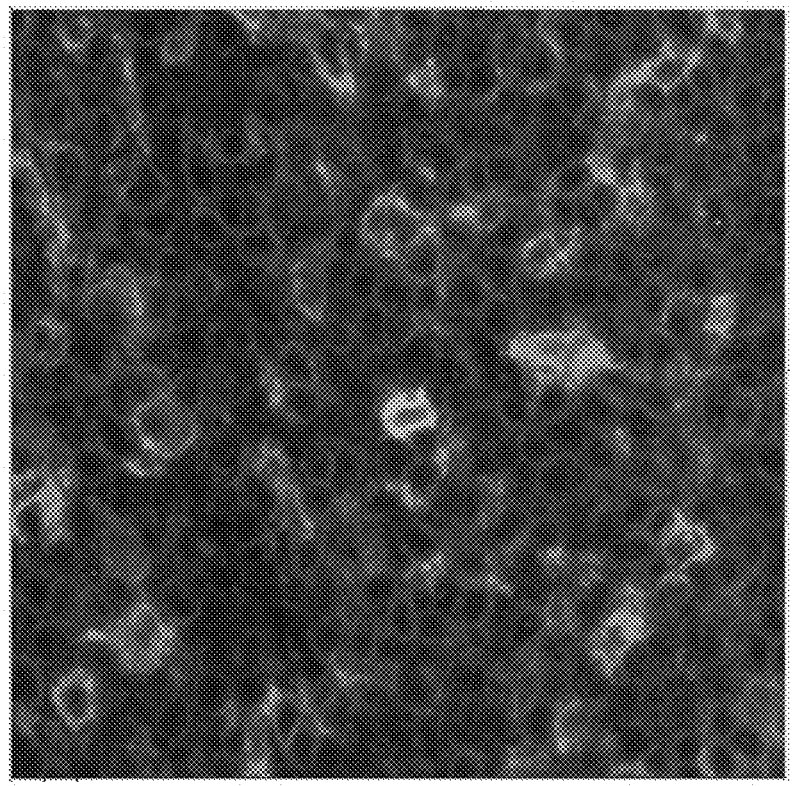
Figure 32:
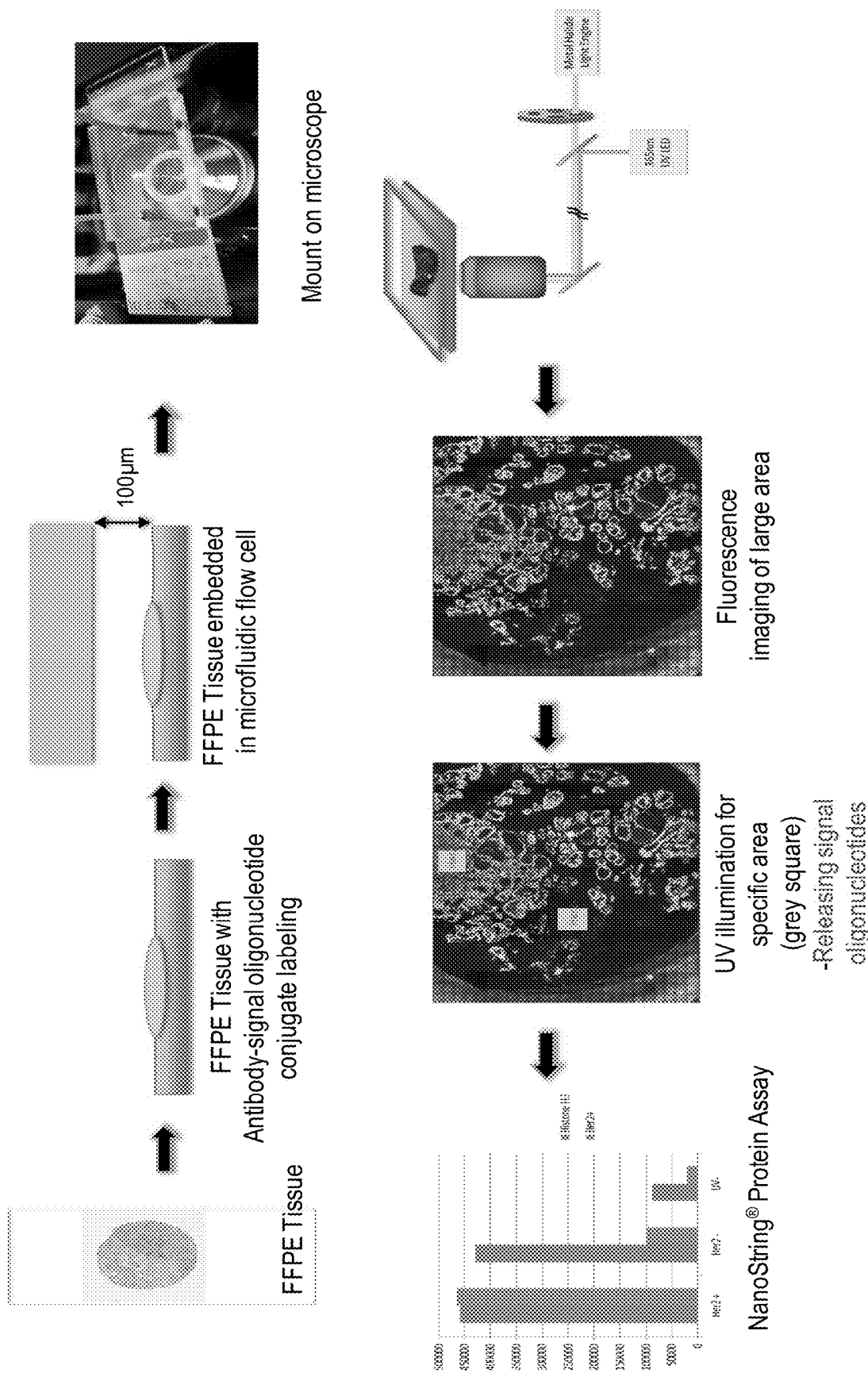
FIG. 32 shows steps in a spatially-resolved FFPE Tissue Protein Assay. The steps are similar to those of a nucleic acid-detecting assay except, in the nucleic acid-detecting assay, the sample is bound with a probe comprising a nucleic acid target-binding domain rather than an antibody.
Figure 33:
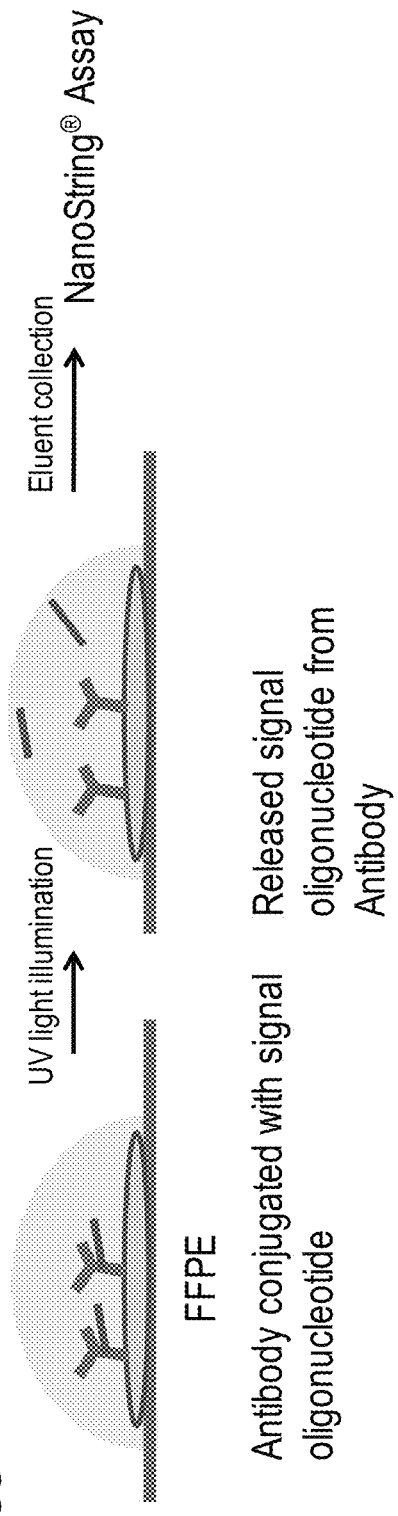
FIG. 33 shows steps in a spatially-resolved FFPE Tissue Protein Assay.

Example 7: A Digital Mirror Device (DMD) is Capable of Illuminating Single Cells FIGS. 30 and 31 are photomicrographs showing that UV illumination using a digital mirror device (DMD) is capable if illuminating single cells in a tonsil tissue sample.

These data show that the present invention is capable of single cell resolution when using a DMD.

Figure 34:
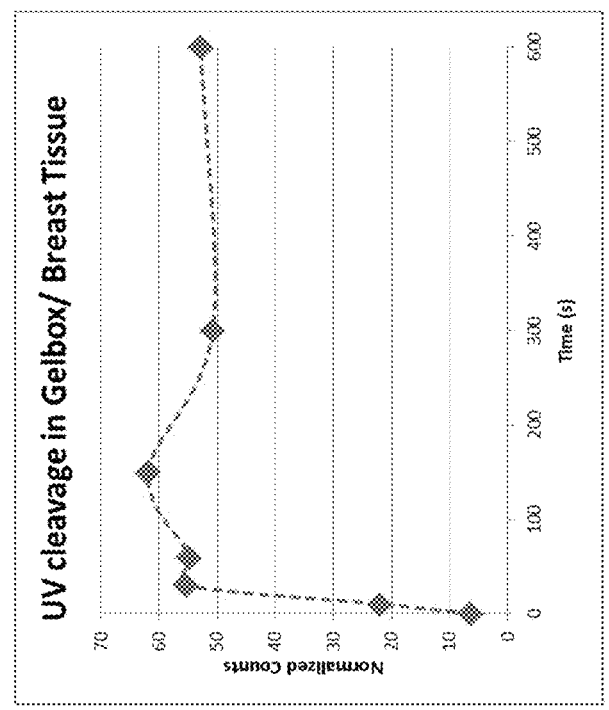
FIG. 34 shows data from an embodiment in which a whole tissue or whole sample is illuminated, e.g., with a standard UV gel box, to release signal oligonucleotides previously attached to a probe.

Example 8: A Gel Box is Capable of Illuminating an Entire Sample and Releasing Signal Oligonucleotides from Probes Bound to the Entire Sample FIG. 34: Shows an embodiment in which a whole tissue or sample is illuminated, e.g., with a standard laboratory UV gel box. Here, a FFPE tissue slide was placed on the light panel, a wax pen was used to hold buffer solution (TBS) covering the FFPE tissue, and UV light exposure (276-362 nm, e.g., 302 nm; ~5 mW/cm²) was applied to the tissue through the glass slide (1 mm thickness). The data shows that within about one minute of UV exposure, most of signal oligonucleotides are released from FFPE bound antibodies. Counts are normalized to a positive control.

Example 9: Illumination from a Microscope is Capable of Illuminating a Region of Interest in a Sample and Releasing Signal Oligonucleotides from Probes Bound to the Region of Interest FIG. 35 shows an embodiment in which a portion of a tissue or sample is illuminated, e.g., with a microscope, i.e., UV cleavage under Microscope (Time titration experiment).

This is in contrast to the experiment of Example 8, in which a whole sample is illuminated. Here, UV LED (at 365 nm) is applied at about ~150 mW/cm$^2$ with a 20× objective. UV illumination scans the whole tissue area identified by previous fluorescence (~590 nm excitation) bright field imaging. Within about one second of UV exposure per field of view (FOV), most signal oligonucleotides are released from FFPE bound probes. The gel box experiment of Example 8 was utilized as a non-spatially resolved 100% release control. Counts are normalized ratio to positive control. Blue: microscope data with variable lengths of exposure time; Red: Gel box 2.5 minutes exposure data. Also shown are photographs and a schematic showing configuration of the microscope apparatus.

Figure 36:
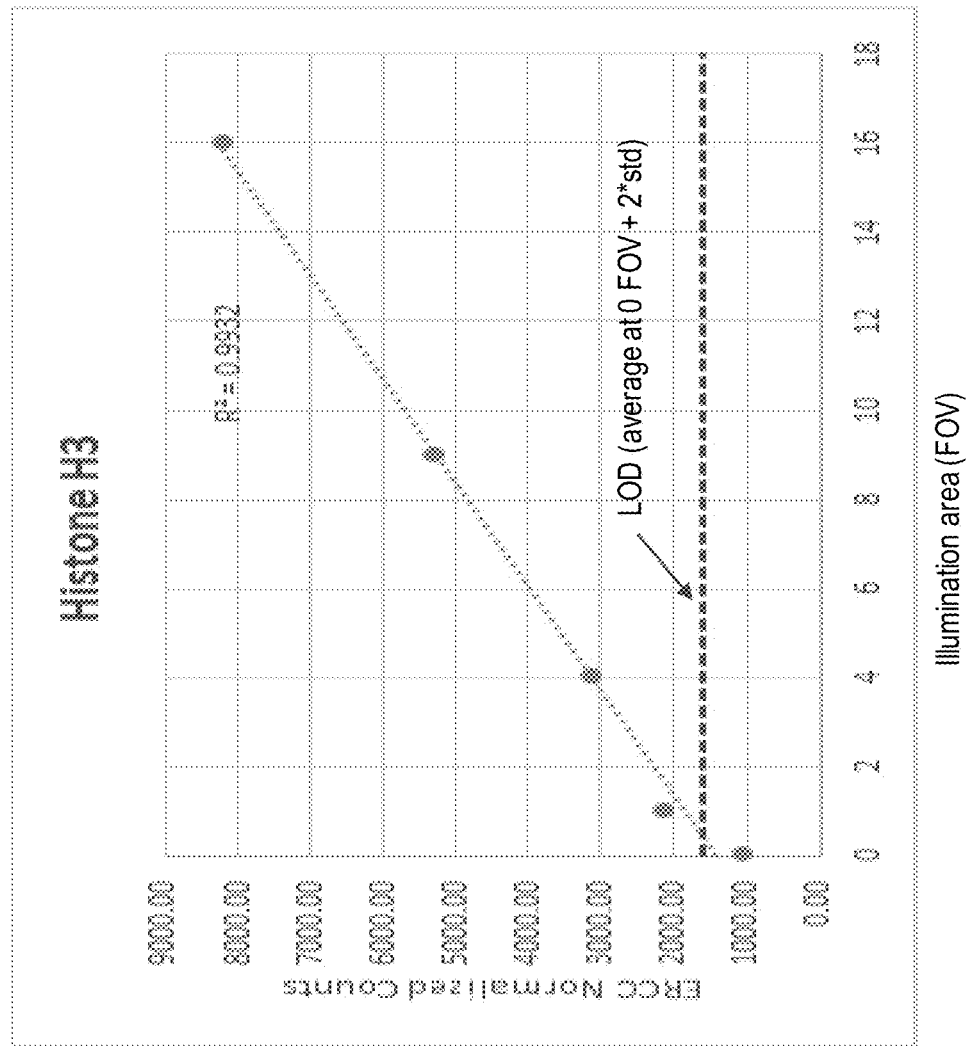
FIG. 36 shows an embodiment in which a portion of a tissue or sample is illuminated, e.g., with a microscope, i.e., UV cleavage under Microscope (Illumination area titration experiment).

FIG. 36 shows signal oligonucleotides are released from a uniformly distributed anti-Histone (H3) antibody bound to lung tissue sample. Tissue was exposed to one second of UV (365 nm, ~150 mW/cm$^2$ with 20× objective) per field-of-view (FOV) of about 450 μm×330 μm=0.15 mm$^2$. "Macro-Volume" used to collect effluent was about 70 μl. This decreases the limit of detection to (FOV/5) ~99 μm×99 μm. with collection effluent of about 5 μl. Hence, in this example, the limit of detection is approximately 10 cells×10 cells niche. These data show that antibody signal is proportional to spatially resolved illumination area FOV and estimate "macro-fluidics" limit-of-detection (LOD).

Figure 37:
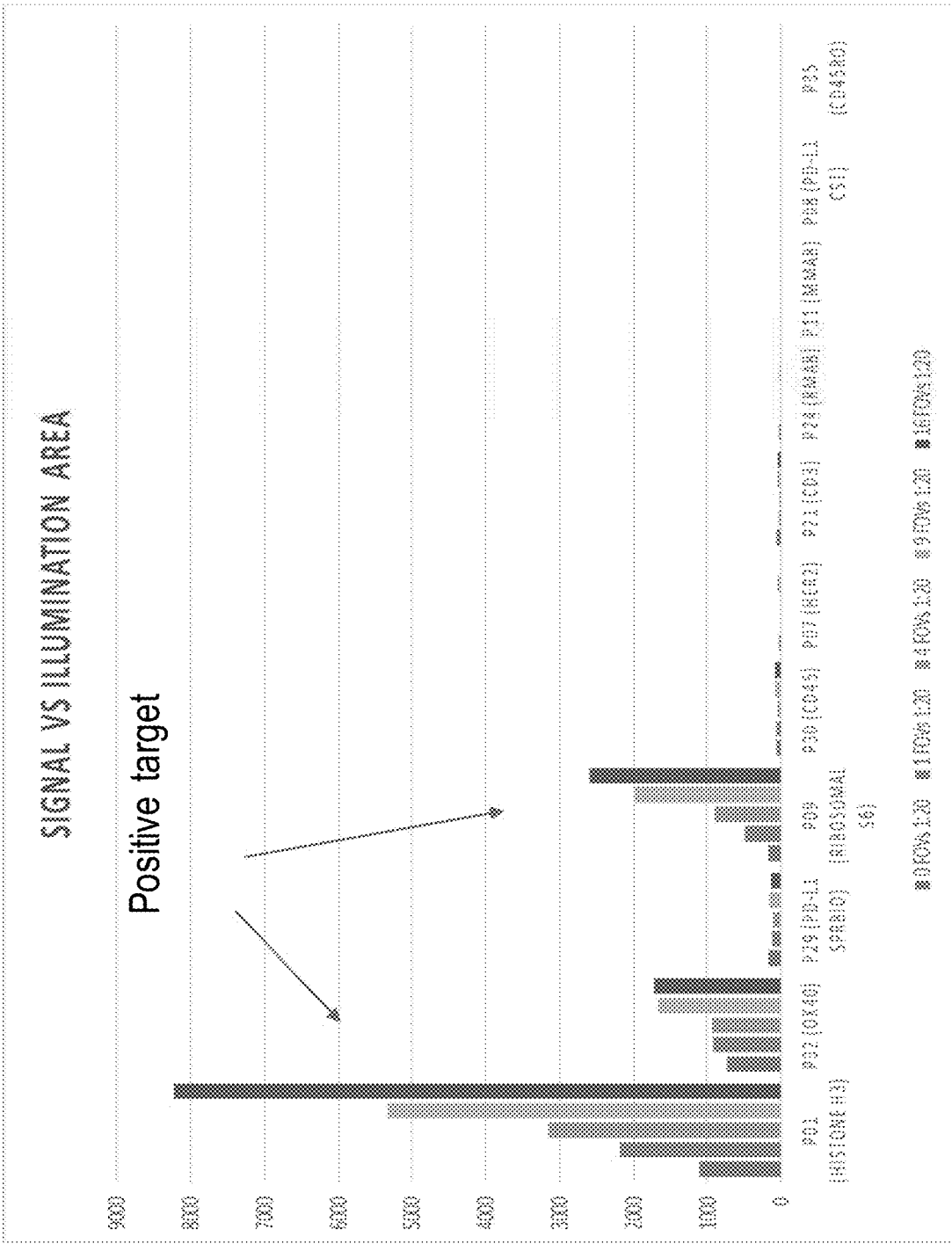
FIG. 37 shows an embodiment in which a portion of a tissue or sample is illuminated, e.g., with a microscope, i.e., UV cleavage under microscope (Illumination area titration experiment—multiple targets).

FIG. 37 shows an embodiment in which a portion of a tissue or sample is illuminated, e.g., with a microscope, i.e., UV cleavage under microscope (Illumination area titration experiment) and for multiple targets. Shown is UV cleavage of multiple targets in a tissue: two positive targets (Histone H3 and Ribosomal S6) and eight 8-negative targets. Only one negative target (Ox40), showed high background. Data from zero, one, four, nine and sixteen fields of view are shown.

Figure 38:
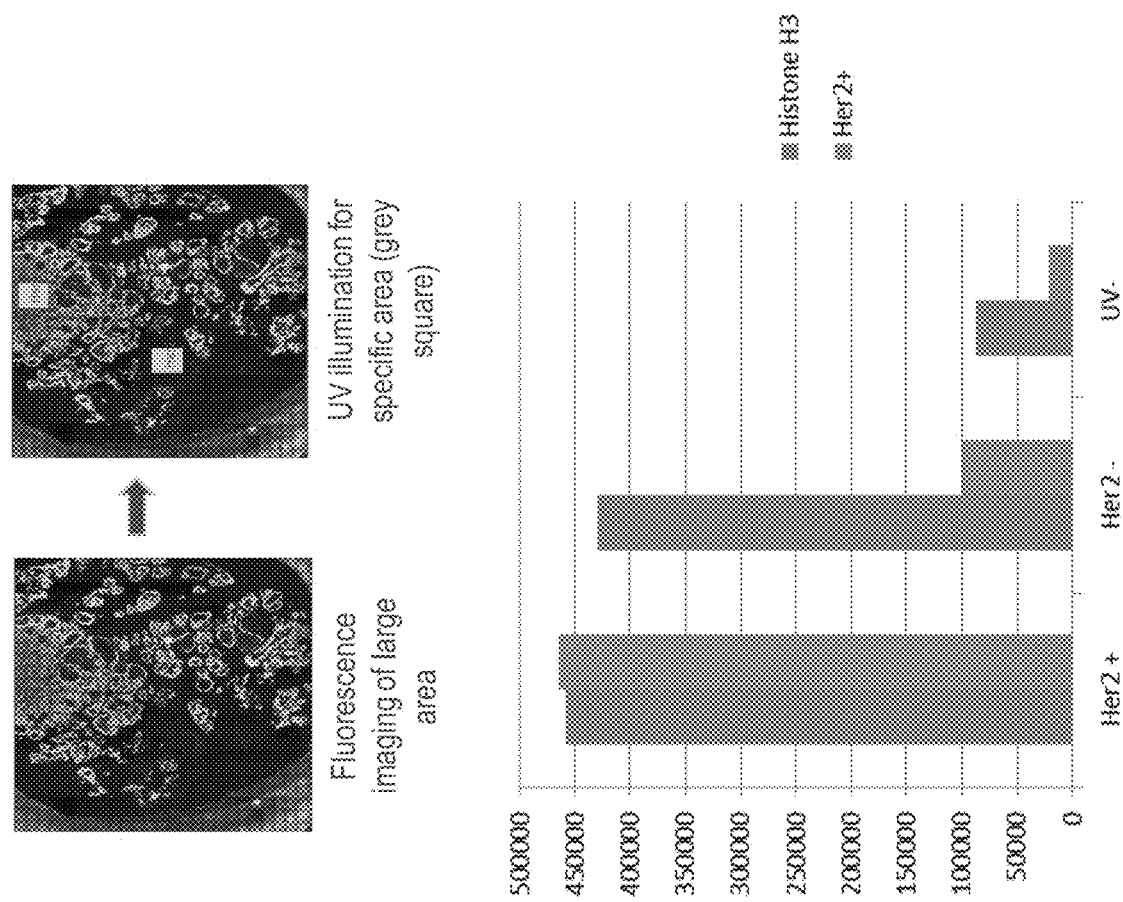
FIG. 38 shows an embodiment in which a region of interest in a tissue (e.g., a breast cancer sample) is first identified for expression of a marker and this region of interest is then illuminated (e.g., with UV) to release signal oligonucleotides from a probe.

Example 10: A Region of Interest May be Pre-Identified by a Labeling Technique and then the Region of Interest is Illuminated Signal Oligonucleotides are Released from Probes Bound to the Pre-Identified Region of Interest FIG. 38 shows an embodiment in which a region of interest in a tissue (e.g., a breast cancer sample) is first identified for expression of a marker (here Her2) and this region of interest is then illuminated (e.g., with UV) to release signal oligonucleotides from a bound probe. Data shown compares the amount of signal oligonucleotides, for two targets (here, Her2 and Histone H3), released from two locations: one region of interest that was pre-identified as Her2+ and one that was pre-identified as Her2−.

Example 11: A Sample Embedded in a Flow Cell Provides Collection of Elution from the Entire Sample and not Only from a Region of Interest that is Illuminated and from which Signal Oligonucleotides are Released FIG. 39 shows an embodiment in which a tissue is embedded in flow cell. Here, FFPE Tissue embedded in microfluidic flow cell (a 9 mm circular chamber with volume of 100 μm height with an approximate 25 μl volume [when the flow cell has a 300 μm height the approximate volume is 75 μl]) controlled by a syringe pump. UV cleavage inside flow cell, showing elution profile illumination one area (9 FOVs) and elution, then illumination another area (9 FOVs) and elution. Data for multiple fractions is shown. As with the data of Example 10, here a region of interest was pre-identified for expression of a fluorescently-labeled marker.

Figure 40:
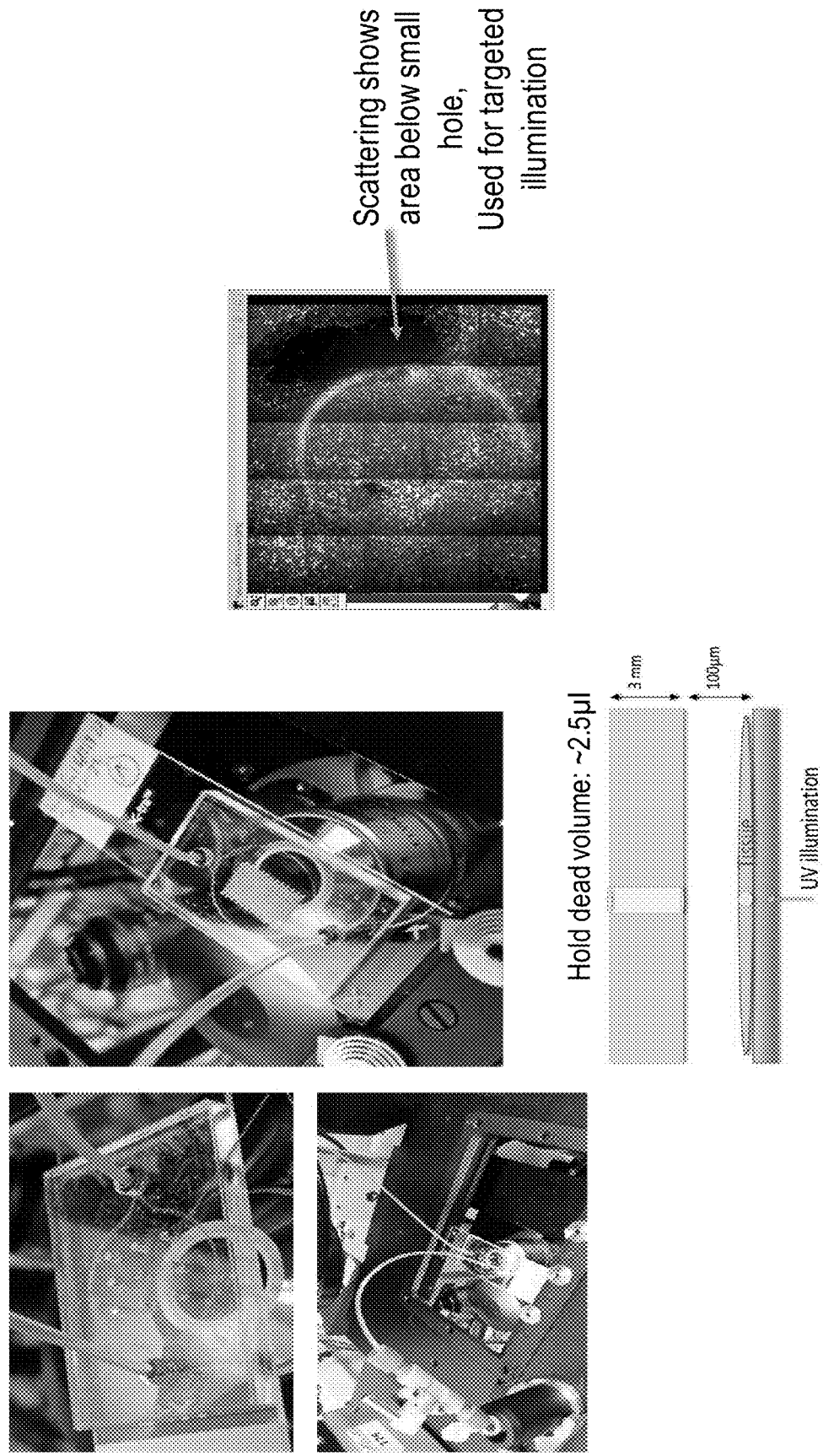
FIG. 40 shows an embodiment in which a tissue is embedded in flow cell with small holes. Also shown are photographs and a schematic showing configuration of the apparatus.

Example 12: A Sample Embedded in a Flow Cell Comprising Small Holes Over a Region of Interest Provides Efficient Collection of Elution from the Region of Interest that is Illuminated and where Signal Oligonucleotides are Released and not from the Entire Sample FIG. 40 shows an embodiment in which a tissue is embedded in flow cell with small holes. Here, elution occurs directly above the region of interest. 0.4-1 mm diameter holes above fluidic chamber allow collection of eluent (e.g., 5 μl collection volume). Tested were 9-hole, 96-hole format, and 12-hole format (for tissue microarray (TMA)). The fluorescence image was created by combining multiple fields of view. Also shown are photographs and a schematic showing configuration of the apparatus.

Figure 41A:
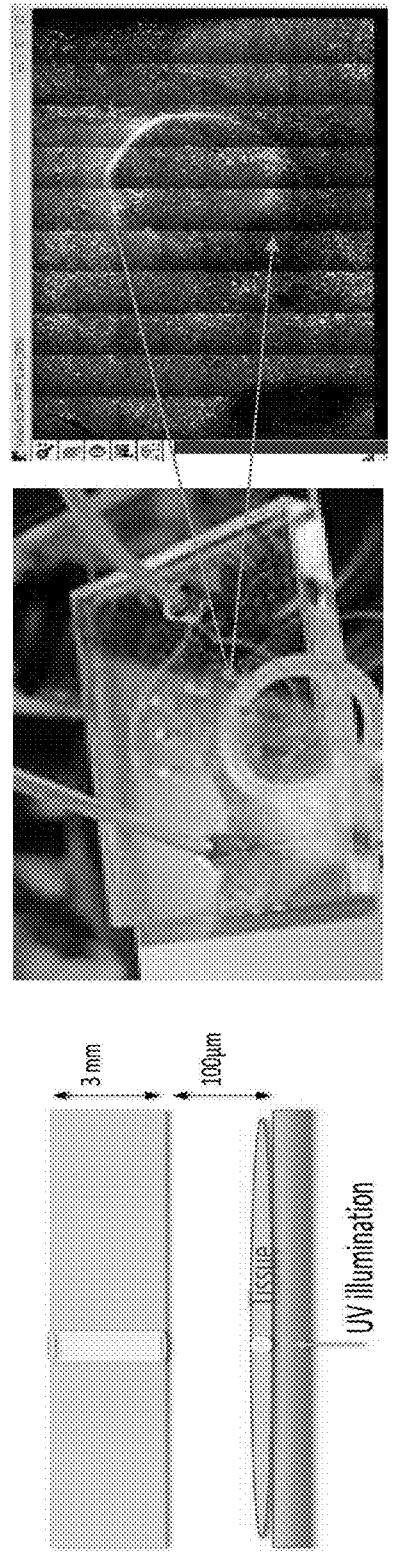
FIG. 41A shows photographs and a schematic showing the configuration of the apparatus in embodiments using a flow cell with small holes.
Figure 41B:
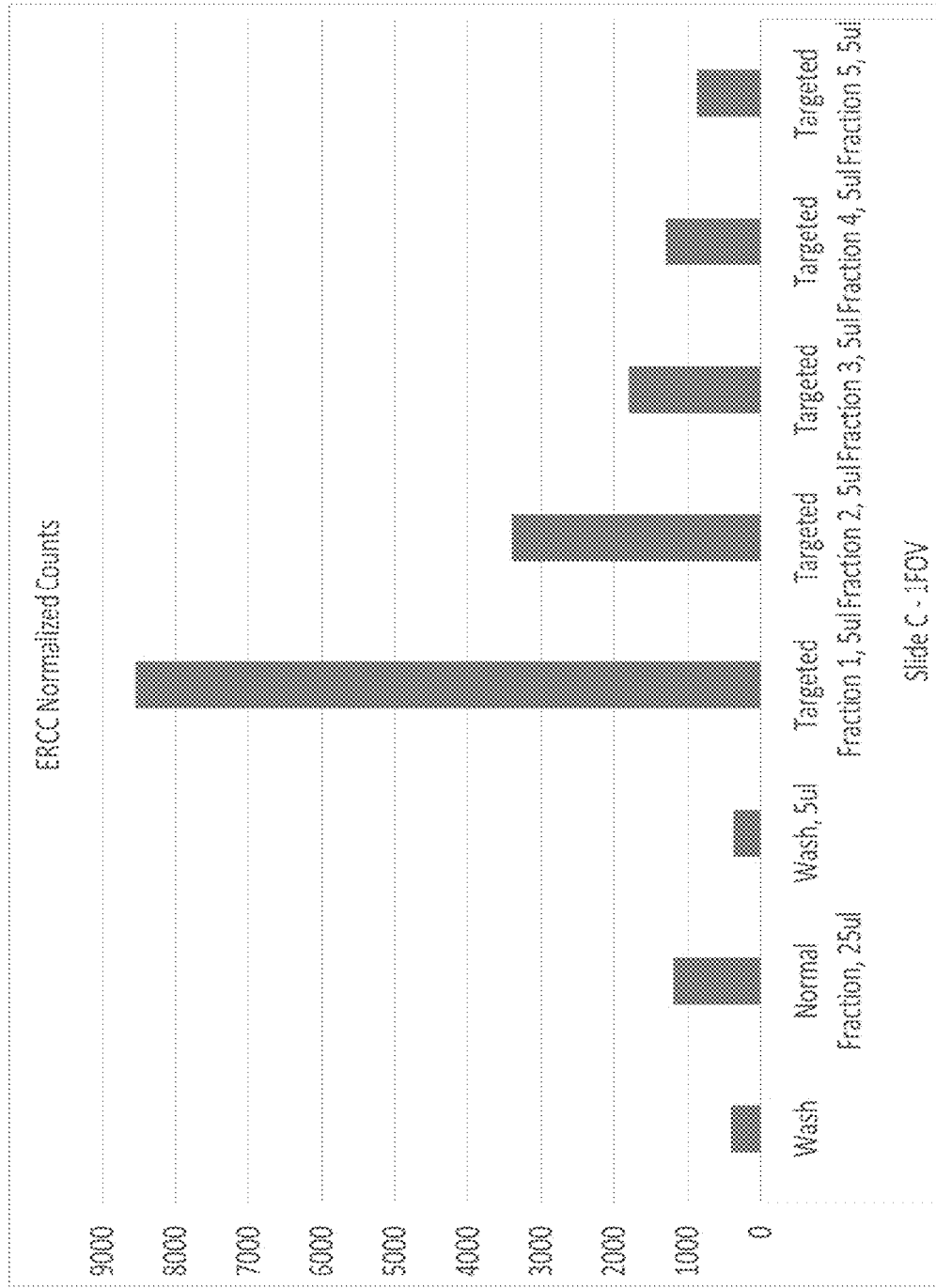
FIG. 41B and FIG. 41C are plots of data collected using embodiments using a flow cell with small holes showing significant signal to noise improvement compared to collection of eluate from entire surface of tissue.
Figure 41C:
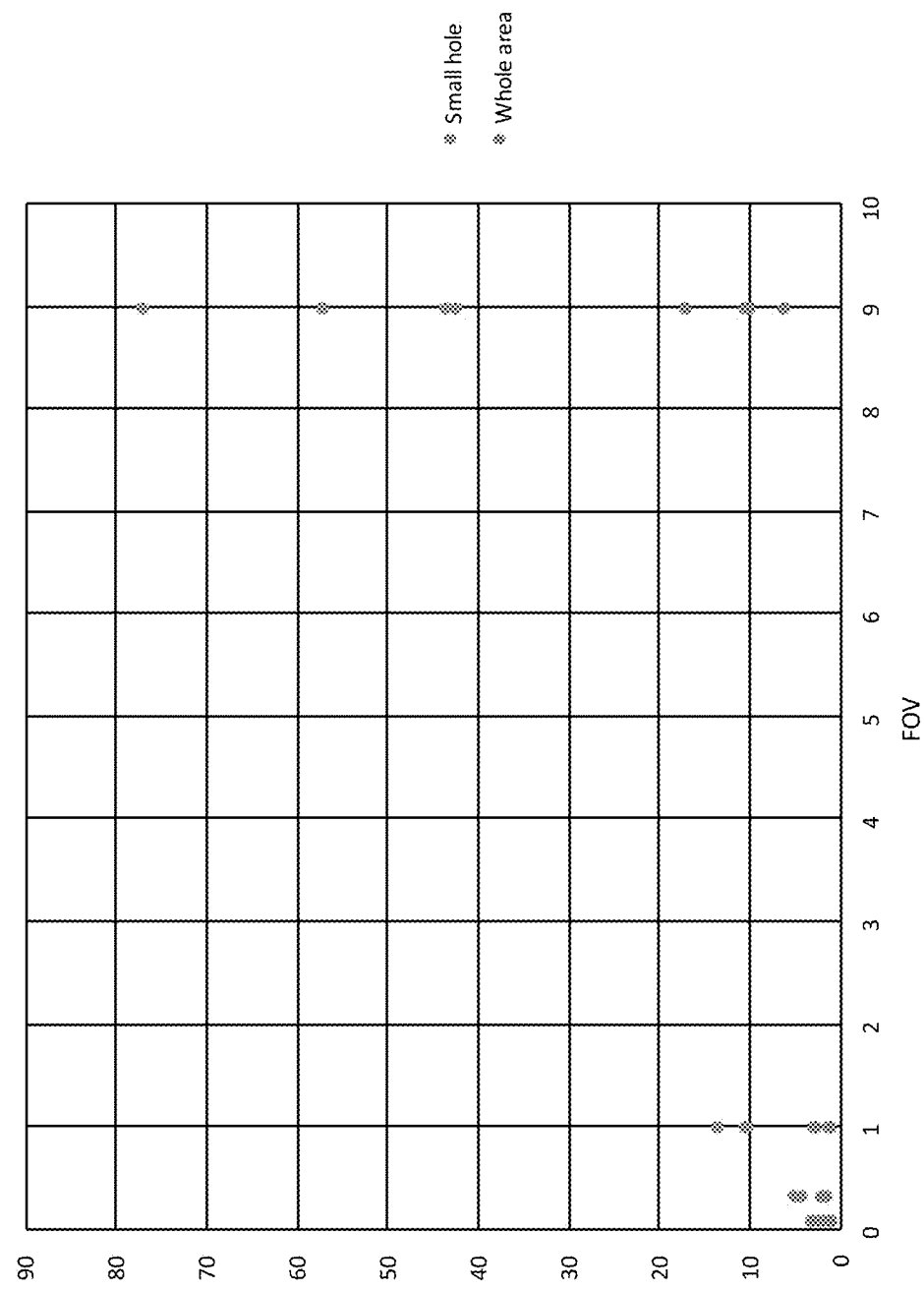

FIGS. 41A to 41C shows that embodiments using a flow cell with small holes have significant signal to noise improvement rather than collection of eluate from entire surface of tissue. The data shows that collecting eluent through a hole above a region of interest increases signal-to-noise by about 7 fold. In this embodiment, 1 mm diameter holes above fluidic flow cell (25 μl chamber) were used to collect eluent (5 μl fractions). Data for multiple fractions is shown.

Figure 42A:
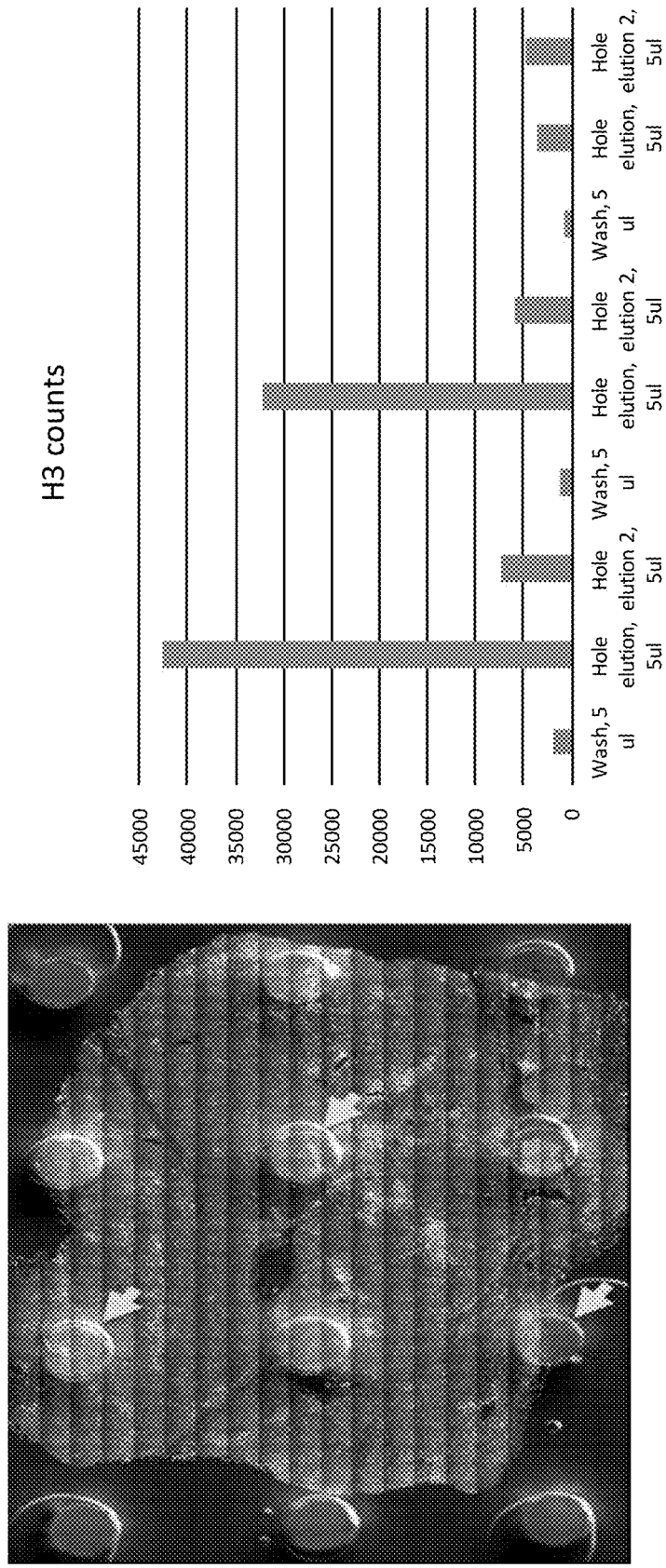
FIG. 42A shows data in the embodiments using a flow cell with small holes (12 hole format)
Figure 42C:
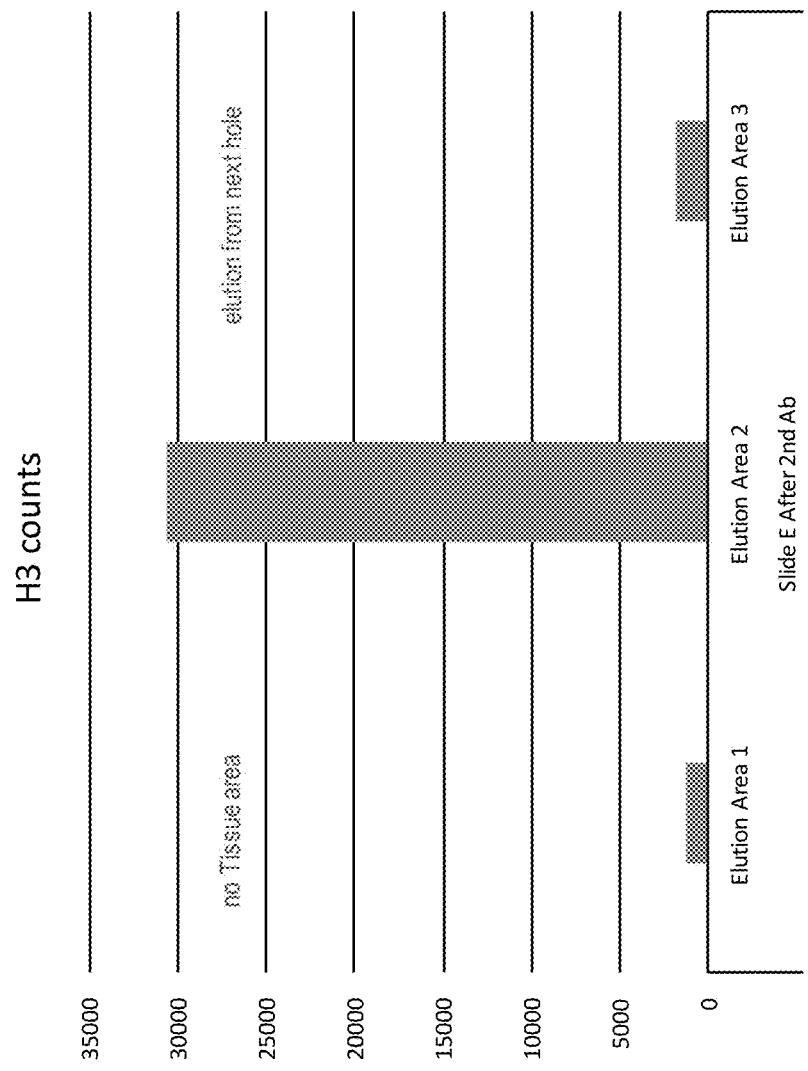
FIG. 42C shows data in the embodiments using a flow cell with small holes.

FIGS. 42A to 42C shows data in the using a flow cell with small holes (12 or 96 hole formats). The data shows that collecting eluent through a hole above a region of interest increases signal-to-noise by about 7 fold. In this embodiment, field of view illumination was focused at the center of a hole; 5 μl volume of elution per hole.

Figure 43A:
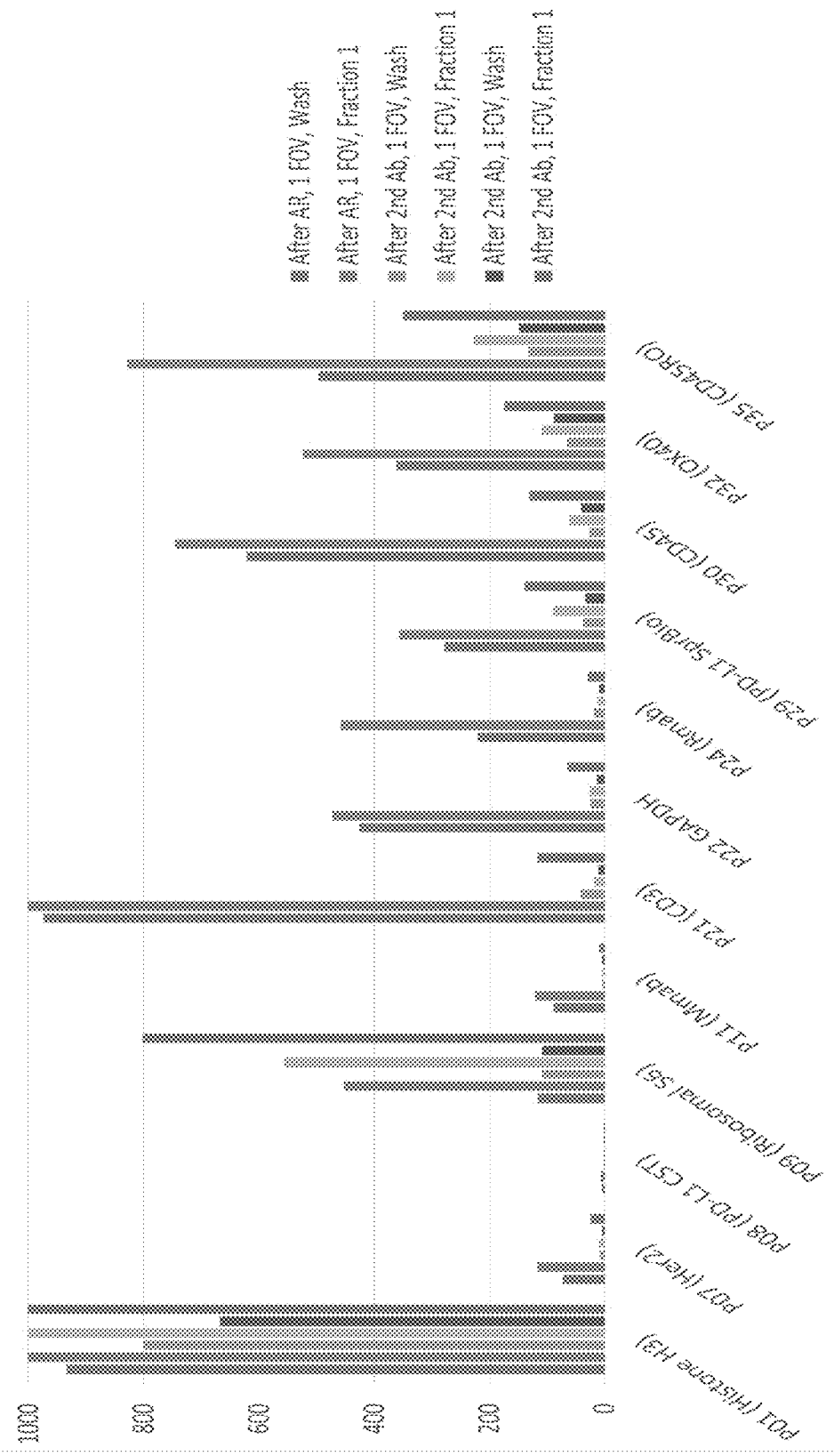
FIG. 43A shows data in comparing background signal from flow cells in which whole tissue elution was performed.
Figure 43B:
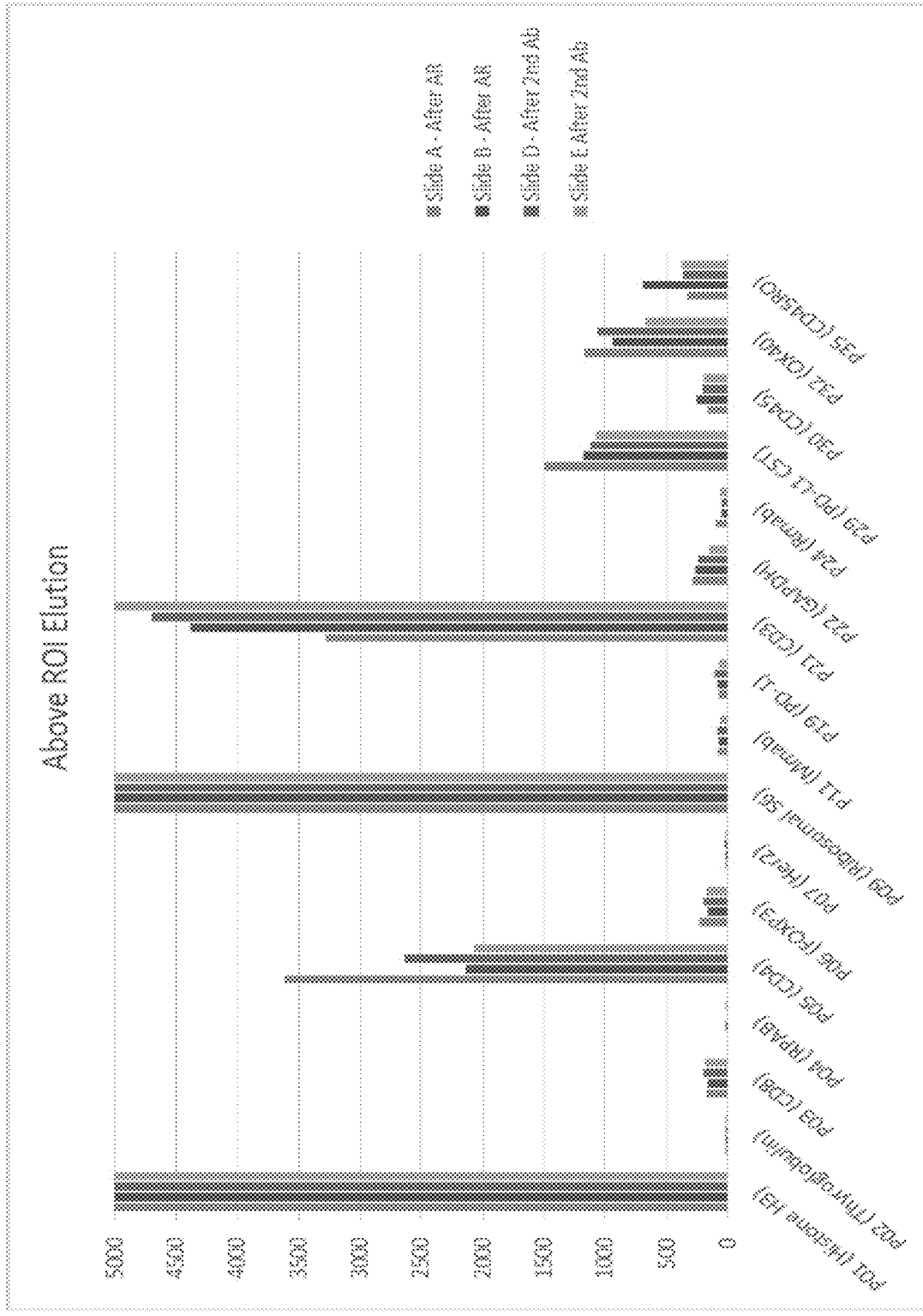
FIG. 43B shows data comparing background signal from flow cells in which elution occurred directly above a region of interest.

FIGS. 43A and B shows data in comparing background signal from flow cells in which whole tissue elution was performed (FIG. 43A; as in Example 11) and background signal from flow cells in which elution occurred directly above a region of interest (FIG. 43B). As seen in FIG. 43A, there is higher background for the whole tissue elution relative to the background seen in the FIG. 43B. Additionally, FIG. 43B shows no difference between in-flow cell and non-flow cell incubation.

Figure 44:
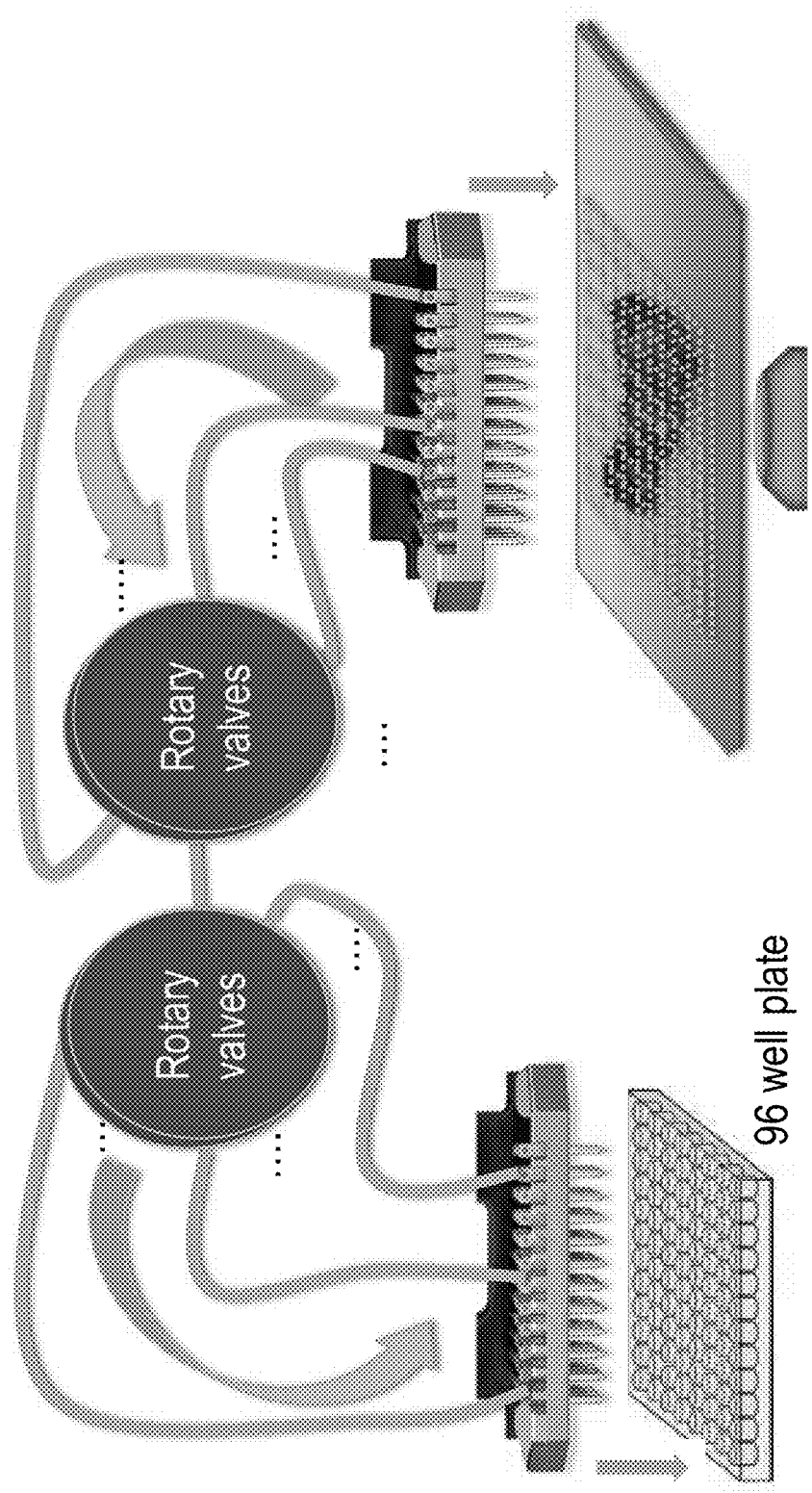
FIG. 44 is a schematic showing eluent collection with an open surface for a multi-region of interest aspiration embodiment. Here is shown a multi-tube array for aspiration/dispensing eluents with rotary valve selection.

Example 13: Released Signal Oligonucleotides can be Elected Via a Single Tube/Pipet, a Plurality of Tubes/Pipets, or a Multi-Tube/Pipet Array FIG. 44 is a schematic showing eluent collection with an open surface for a multi-region of interest aspiration embodiment. Here is shown a multi-tube array for aspiration/dispensing eluents with rotary valve selection. See also, FIG. 47.

Figure 45:
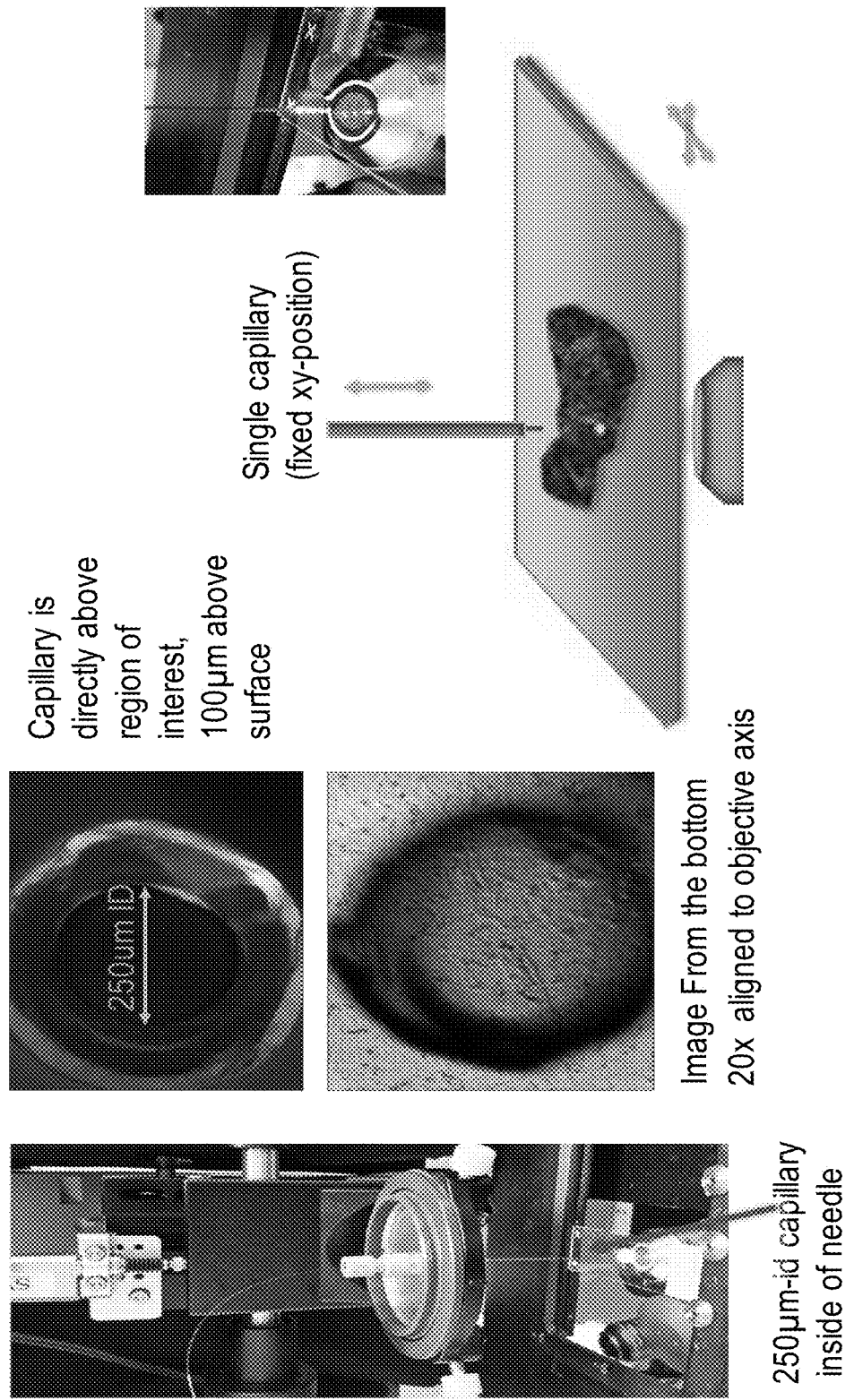
FIG. 45 includes photographs and a schematic showing an embodiment in which eluent collection is through a capillary (micro-aspirator).
Figure 46A:
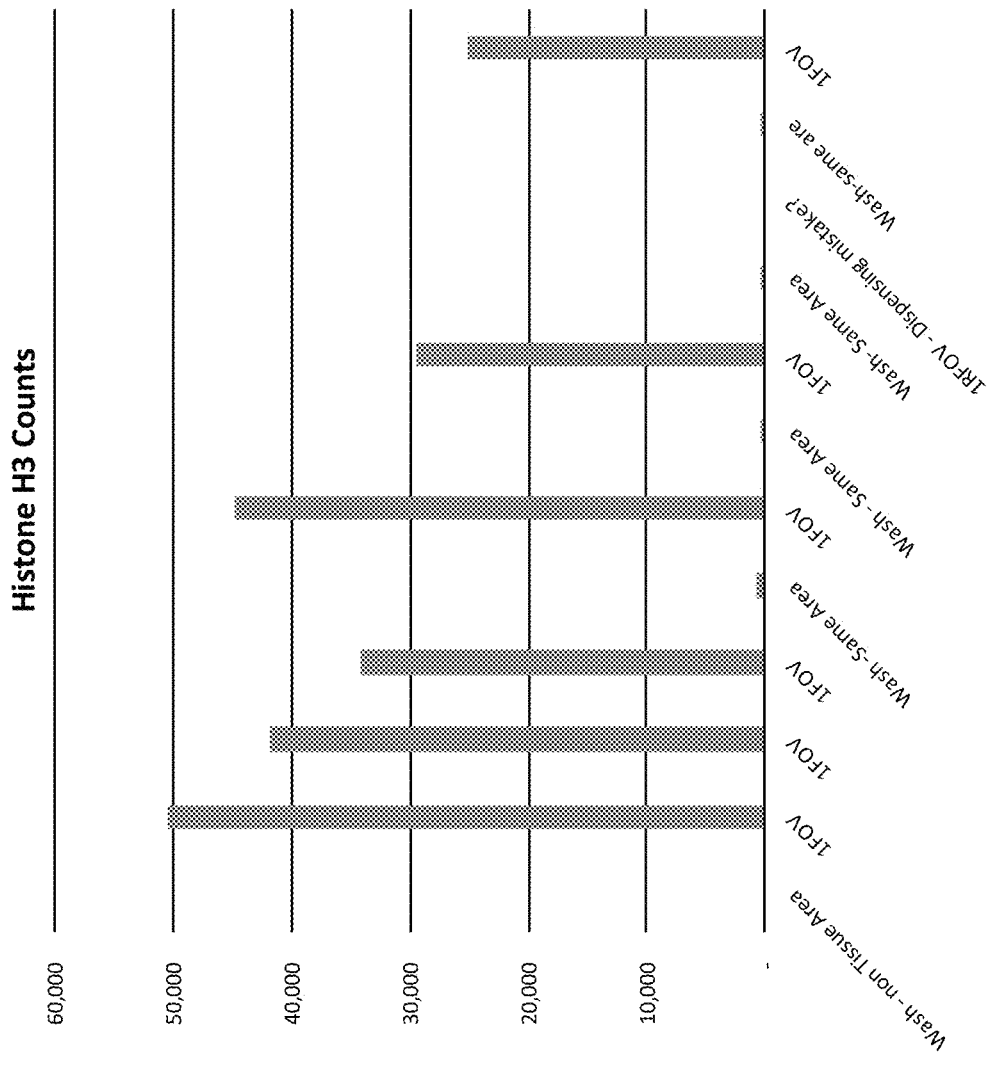
FIG. 46A and FIG. 46B show data from the embodiment of FIG. 45 in which eluent collection is through a capillary (micro-aspirator).
Figure 46B:
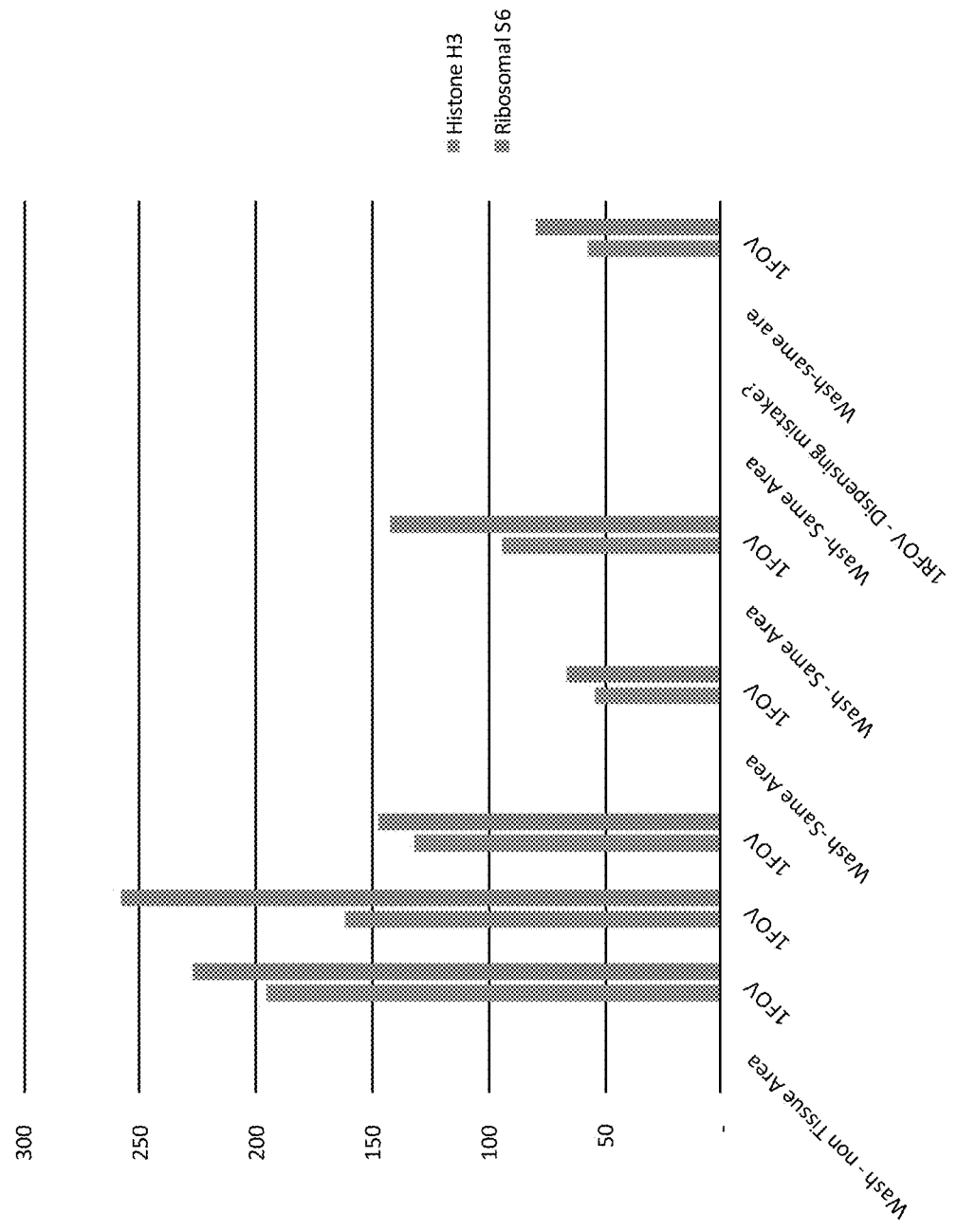

FIG. 45 includes photographs and a schematic showing an embodiment in which eluent collection is through a capillary (micro-aspirator). See also, FIG. 47. FIGS. 46A and B shows data from the embodiment of FIG. 45 in which eluent collection is through a capillary (micro-aspirator). This embodiment has a dramatic improvement in signal to noise: signal to noise ratio increases about 10 fold, compared to flow cell through hole elution and signal to noise ratio increases about 200 fold, compared to whole tissue elution. Here, the LOD area is approximately 60 μm×60 μm.

Figure 48:
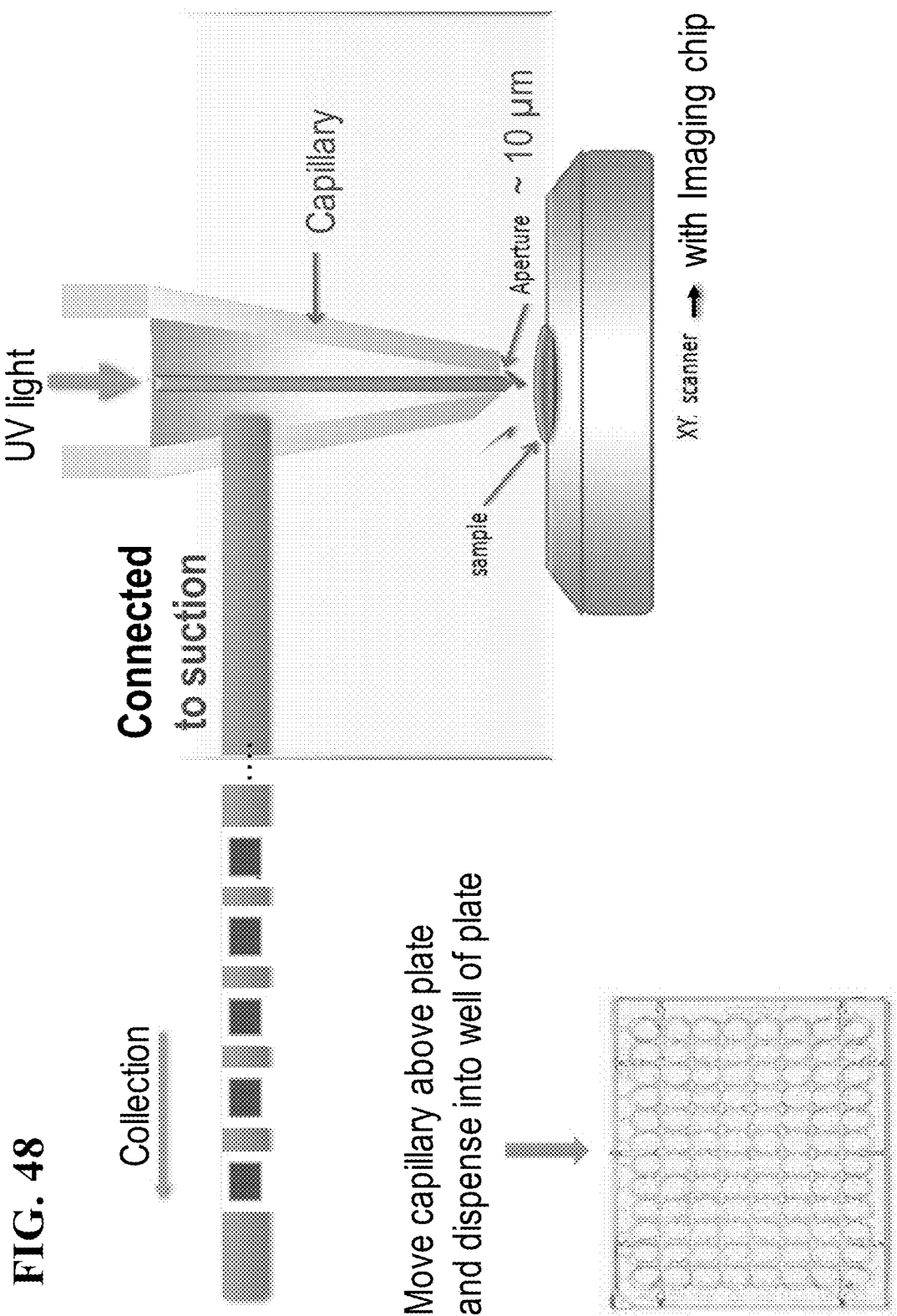
FIG. 48 is a schematic showing illumination and fluid collection through a combined capillary and lens.
Figure 49:
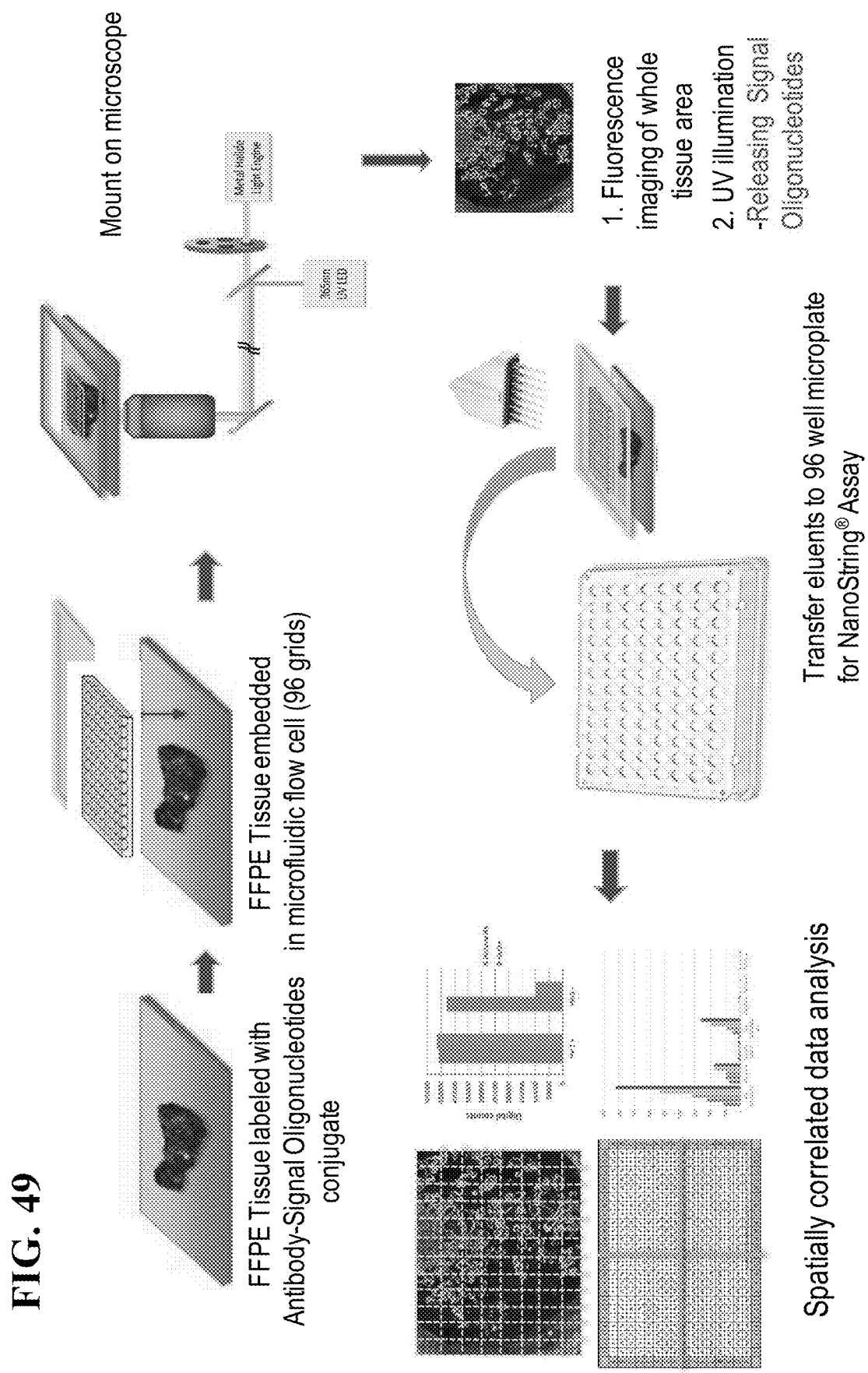
FIG. 49 is a schematic showing steps in an embodiment of a spatially-resolved FFPE tissue assay comprising a 96 well grid.

Example 14: A Device Comprising Both Illuminating and Elution Capabilities can Efficiently and Accurately Obtain Nucleic Acid and/or Protein Expression Data from a Defined Region of Interest FIG. 48 is a schematic showing illumination and fluid collection through a combined capillary and lens.

Figure 50:
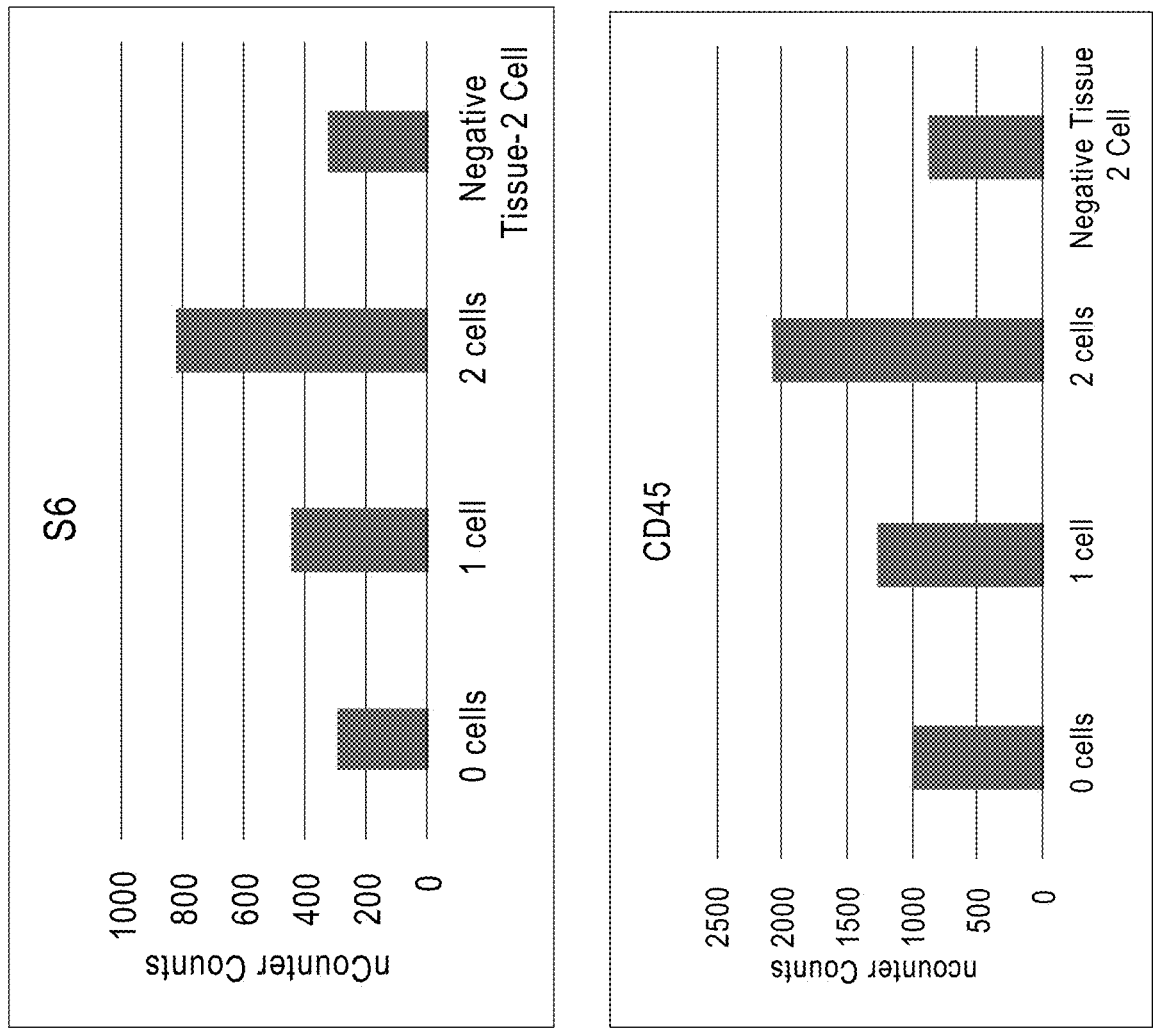
FIG. 50 shows protein expression data obtained from a single cell or two cells using the herein described methods and apparatuses.

Example 15: Protein Expression can be Detected and Quantified from a Single Cell FIG. 50 shows protein expression data obtained from a single cell or two cells using the herein described methods and apparatuses. In the top panel, S6 protein is detected and quantified from at least one cell and in the bottom panel, CD45 protein is detected and quantified from at least one cell.

Example 16: The Herein Described Methods and Apparatuses Provide an Accurate and Efficient Detection and Quantification of Spatially-Resolved, Multiplexed RNA Target and/or Protein Target Expression In situ hybridization (ISH) was performed to hybridize DNA oligo-based probes ("RNA probes"), each comprising a target-binding domain, a signal oligonucleotide, and a photo-cleavable linker, to an endogenous RNA. 5 μm FFPE HER2 3+ breast tissue sections were deparaffinized in xylene, partially rehydrated in graded ethanols, and incubated in 70% ethanol for 1 hour at room temperature. Then sections were incubated in 40 μg/ml proteinase K for 25 minutes at 37° C. Tissues were then incubated in 50% formamide/2×SSC for 15 minutes at room temperature and hybridized overnight at 37 C in a solution of 1 nM probes, 40% formamide, 1 mg/ml yeast tRNA, 10% dextran sulfate, and 0.2% BSA in 2×SSC. After hybridization, two stringent washes in 50% formamide/2×SSC were performed for 25 minutes each at 37° C. Sections were stained with TO-PRO®-3 (Thermo Fisher Scientific) fluorescent nucleic acid stain to visualize tissue morphology. Focused UV light, directed by a digital micromirror device, was then used to cleave DNA signal oligonucleotides from probes in a user-defined region of interest (ROI). For each tissue section, two ROIs comprised a tumorous tissue, two ROIs comprised normal tissue, and two ROIs comprised no tissue at all (histology slide itself). After cleavage, signal oligonucleotides were collected, hybridized to nCounter® Molecular Barcodes, and digitally counted by an nCounter® system from NanoString Technologies®. H&E was performed on tissue sections to verify tumorous and normal tissue ROIs.

On serial sections, standard immunohistochemistry (IHC) was performed using "Protein probes," each comprising an antibody as target-binding domain, a DNA signal oligonucleotide, and a photo-cleavable linker. Sections were then stained with an anti-rabbit Alexa 594 secondary antibody and TO-PRO®-3 (Thermo Fisher Scientific) fluorescent nucleic acid stain to visualize tissue morphology. Focused UV light, directed by a digital micromirror device (DMD), was then used to cleave DNA signal oligonucleotides from probes in a user-defined ROI. For each tissue section, two ROIs comprised tumorous tissue, one ROI comprised normal tissue, and two ROIs comprised no tissue at all (histology slide itself). ROIs were matched to the ROIs selected for ISH probe cleavage. Following cleavage, the signal oligonucleotides from protein targets were mixed with the signal oligonucleotides from RNA targets and all were quantitated as described above. H&E was performed on tissue sections to verify tumorous and normal tissue ROIs and to verify ROIs were correctly matched between ISH and IHC tissues.

Figure 51:
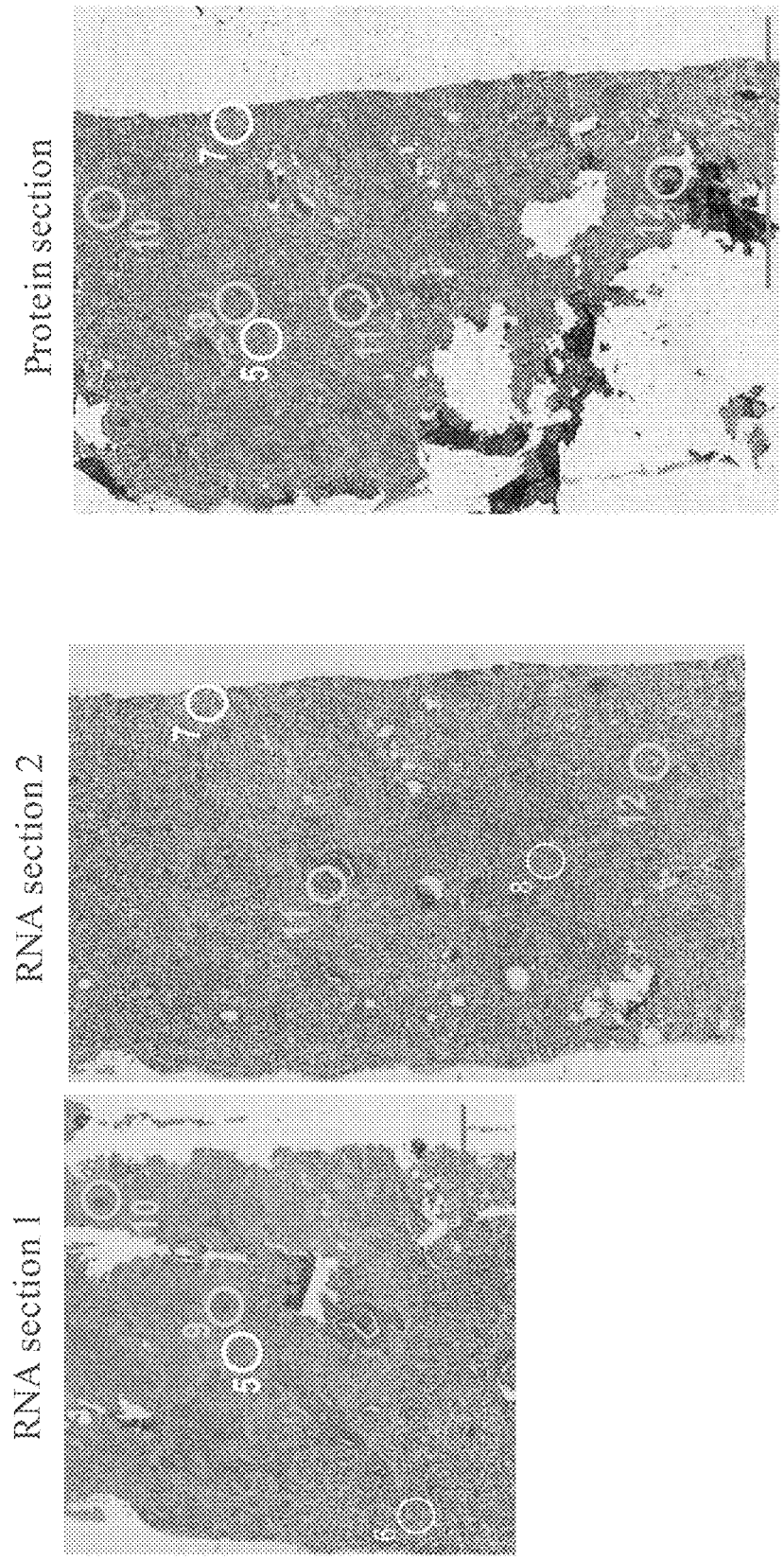
FIG. 51 identifies regions of interests located on serial sections from a single tumor sample.

FIG. 51 shows ROIs sampled from serial sections of the same tumor sample. Regions 1-4 are not shown in this image and, instead, were taken from portions of the tissue that did not contain tissue (negative controls—"No Tissue"). Regions 5-8 contained low numbers of tumor cells ("Normal Tissue"). Regions 9-12 contained high numbers of tumor cells ("Tumor").

Figure 52:
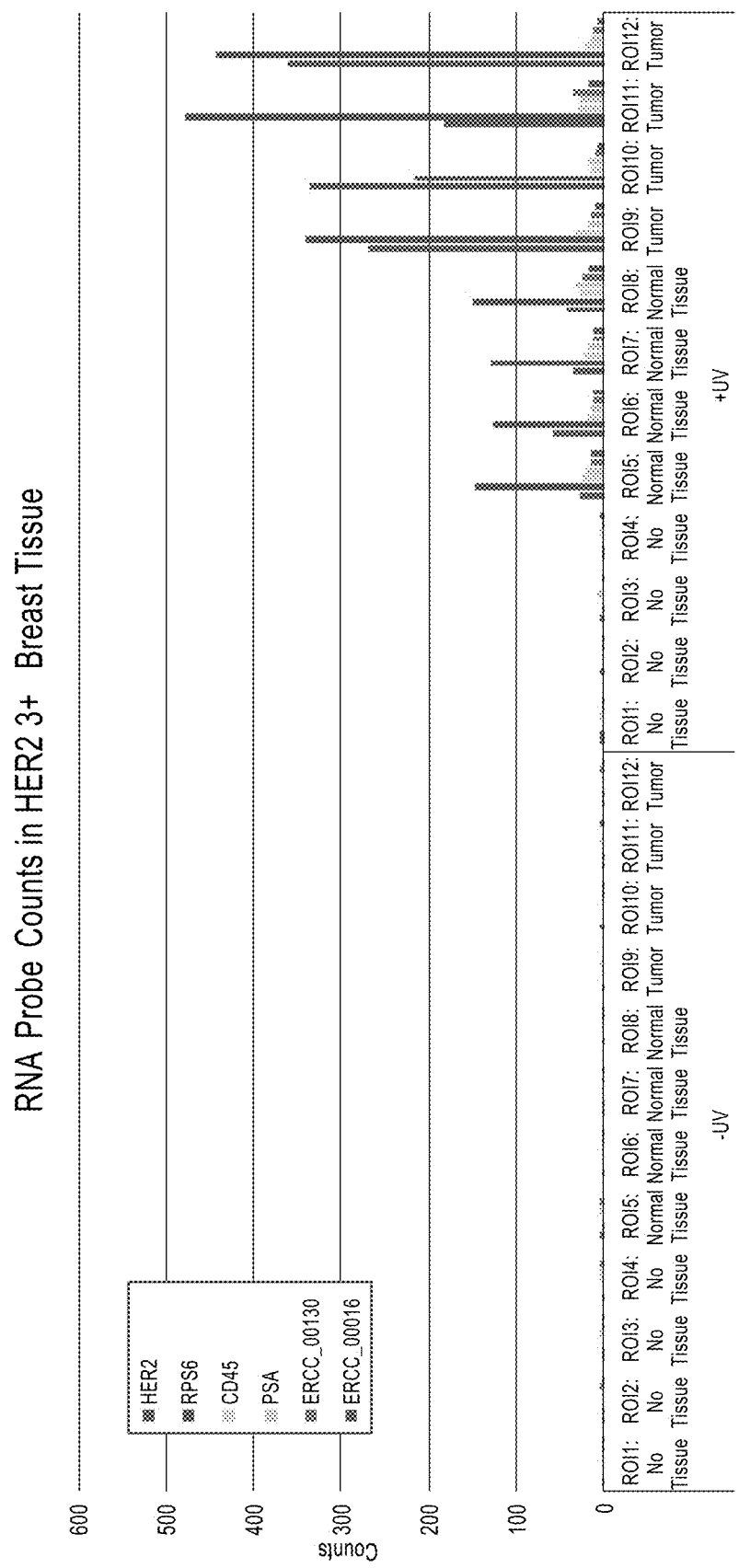
FIG. 52 shows counts obtained for six of the nine RNA probes included in the assay of Example 16.
Figure 53:
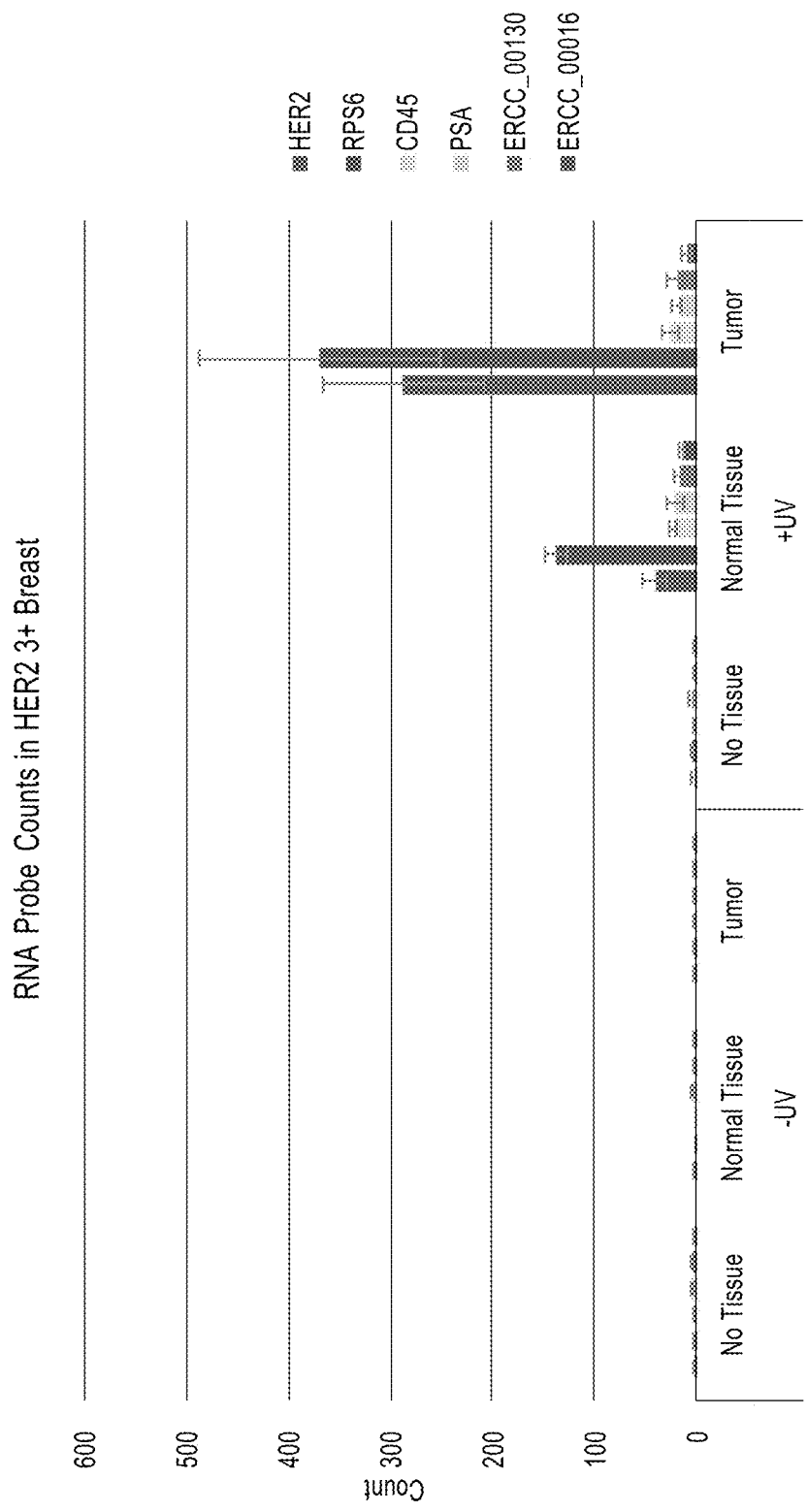
FIG. 53 shows the averages and standard deviations of counts shown in FIG. 52.

FIG. 52 shows counts obtained for six of the nine RNA probes included in this assay. For each ROI, a sample was collected prior to applying the UV illumination (the "−UV" set of data) and prior to collecting a plus UV sample from the same region (the "+UV" set of data). Background levels of counts are obtained when UV was not applied to the sample; thus showing the UV-dependence of an obtained signal. ROIs that were +UV, but not directed to tissue (i.e., ROIs 1-4—"No Tissue") gave background counts. Regions that were primarily normal tissue (i.e., ROIs 5-8—"Normal Tissue) gave low counts for the HER2 probe (orange bars on the graph). Regions that were primarily tumor tissue (i.e., ROIs 9-12—"Tumor") gave higher counts for HER2. A similar, but less dramatic, increase was seen for the Ribosome S6 probe (green bars in graph). Additional control probes targeted RNAs not expected to be expressed highly in this tissue type gave consistent counts that did not show differential levels between Normal and Tumor Tissue. These control probes were designed to target CD45, PSA (Prostate-Specific Antigen), and two unique ERCC sequences. For clarity, FIG. 53 shows the averages and standard deviations of data shown in FIG. 52.

Figure 54:
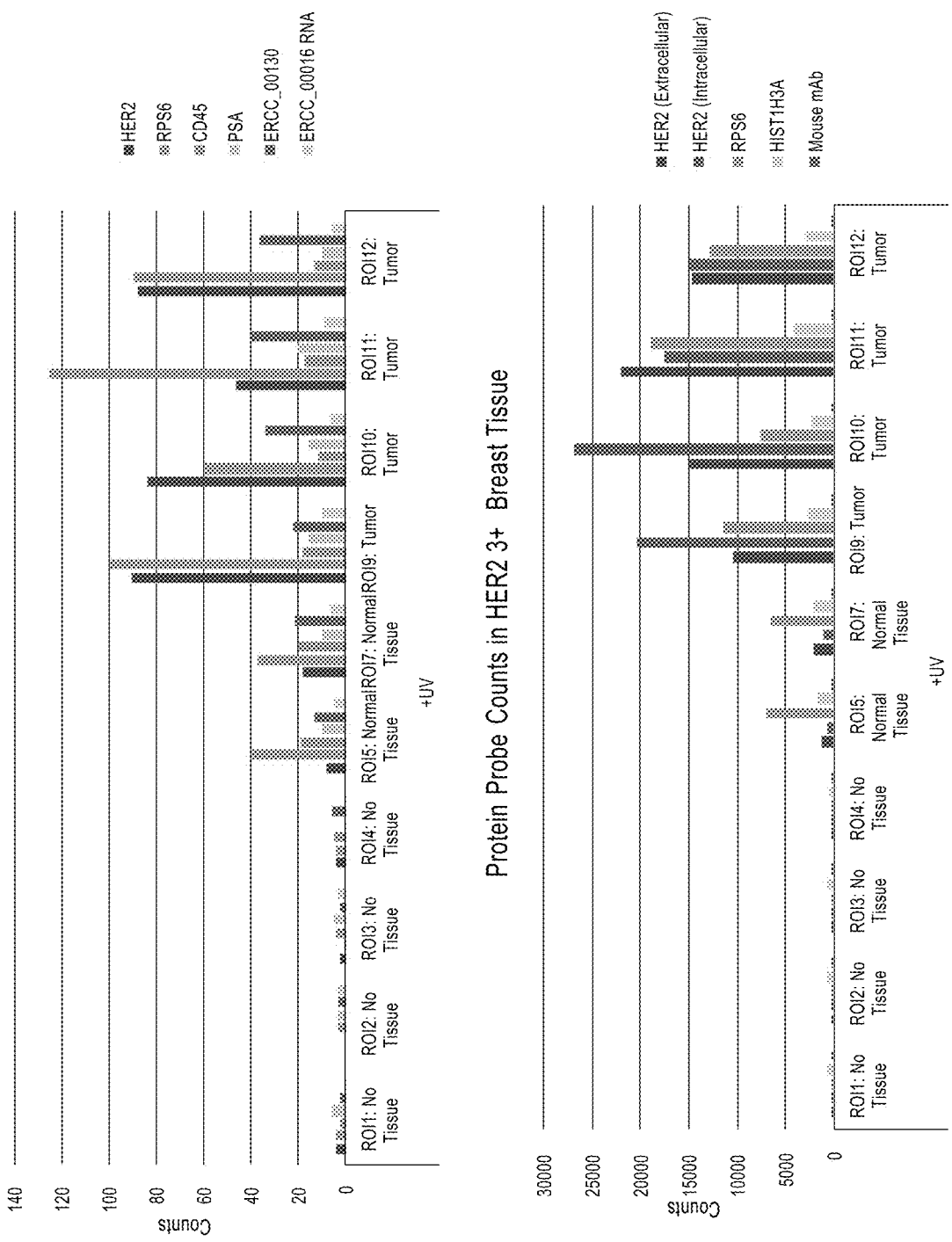
FIG. 54 shows RNA expression data and protein data for probes that were simultaneously hybridized to nCounter® Molecular Barcodes, and digitally counted by an nCounter® system from NanoString Technologies®.

These RNA probe samples were also run simultaneously with Protein probes that analyzed the sample regions of the tumor sample. For this, RNA and Protein probes were simultaneously hybridized to nCounter® Molecular Barcodes, and digitally counted by an nCounter® system from NanoString Technologies®. Counts for this assay are shown in FIG. 54. An increase in HER2 RNA probe counts (Red bars in top graph) and Protein probe counts (Red and orange bars in bottom graph) are seen in the Tumor regions compare to the normal regions. Only +UV samples are shown. The −UV control sample, as described above, are not shown in this graph because they gave background counts (similar to "No Tissue" counts). ROI 6 and ROI 8 were dropped from this analysis because matching Protein probe samples were not obtained. Thus, signal oligonucleotides from Protein probes and signal oligonucleotides from RNA probes can be detected and quantified together.

Example 17: Partially Double-Stranded Probes have Higher Signal-to-Noise Ratios when Compared to Single-Stranded Probes DNA probes (that recognize and bind to mRNA) were hybridized in situ, as described in Example 16, to RNA in 5 μm FFPE tissues. UV cleavage was performed on whole tissue sections, mounted on separate slides, for 3 minutes using a UV light box (gel box) in 2×SSC+0.1% Tween 20. After cleavage and release of the signal oligonucleotides, the signal oligonucleotides were collected by a pipette and detected as in Example 16. Single-stranded DNA probes, partially double-stranded DNA probes, and no probe controls counts are shown for HER2 3+ breast tissue and tonsil tissue in FIG. 55 (top graph). Signal-to-noise ratios were determined by dividing counts by average background counts (average ERCC counts); see, FIG. 55, bottom graph.

Example 18: Addition of Salmon Sperm DNA Improves Probe Hybridization

Figure 56:
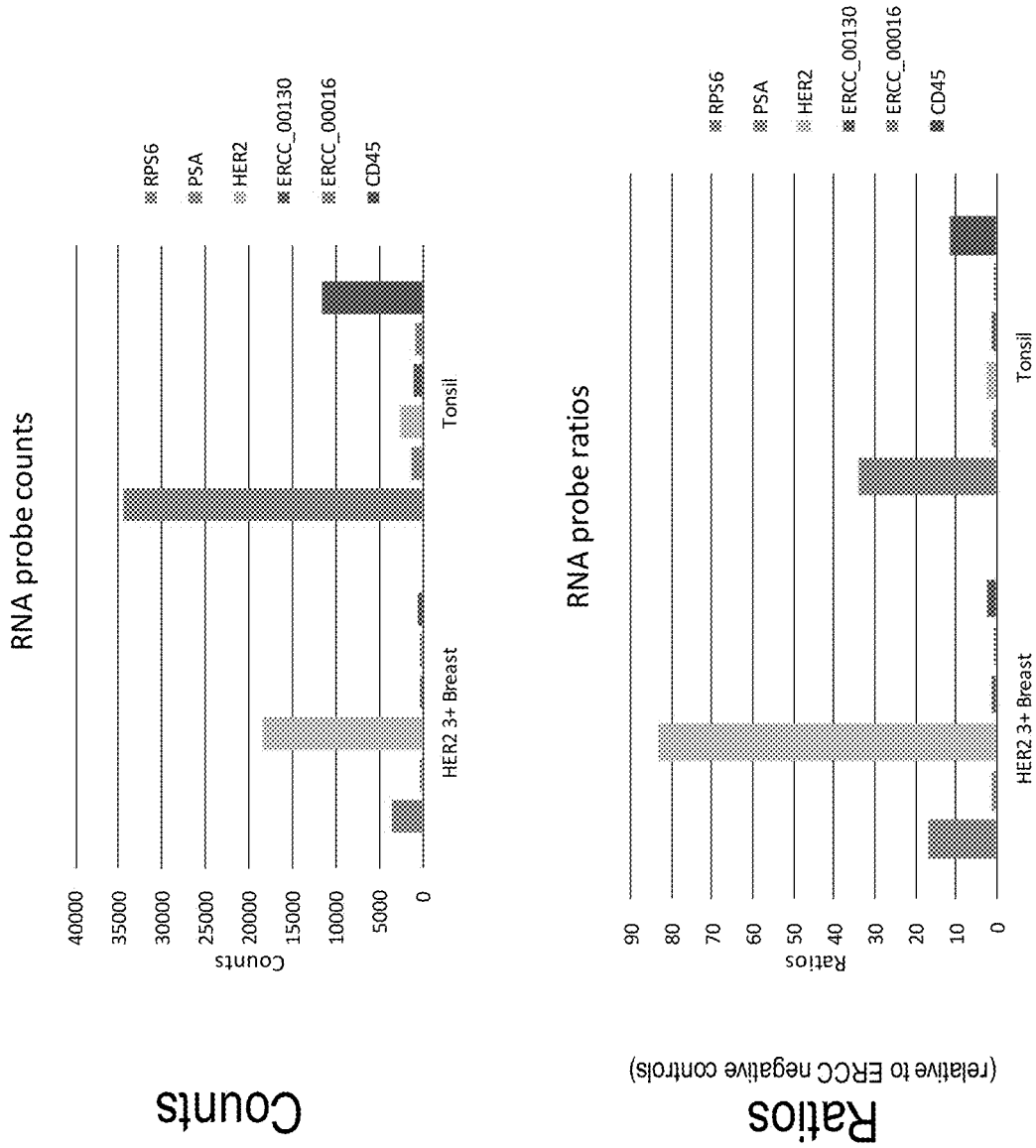
FIG. 56 shows RNA expression data obtained from probes hybridized in the present of salmon sperm DNA.

DNA probes (that recognize and bind to mRNA) were hybridized in situ, as described above, to RNA in 5 µm FFPE tissues. 1 mg/ml sonicated, denatured salmon sperm DNA was used instead of yeast tRNA during hybridization. Slides were hybridized with a solution of 1 nM probes, 40% formamide, 1 mg/ml sonicated, denatured salmon sperm DNA, 10% dextran sulfate, and 0.2% BSA in 2×SSC. UV cleavage and signal oligonucleotide collection and detection were performed as described in Example 17. Single stranded DNA probes are shown in HER2 3+ breast and tonsil (FIG. 56). Signal-to-noise ratios were determined by dividing counts by average background counts (average ERCC counts).

Example 19: PSA (Prostate-Specific Antigen) RNA Probe is Highly Specific

Figure 57:
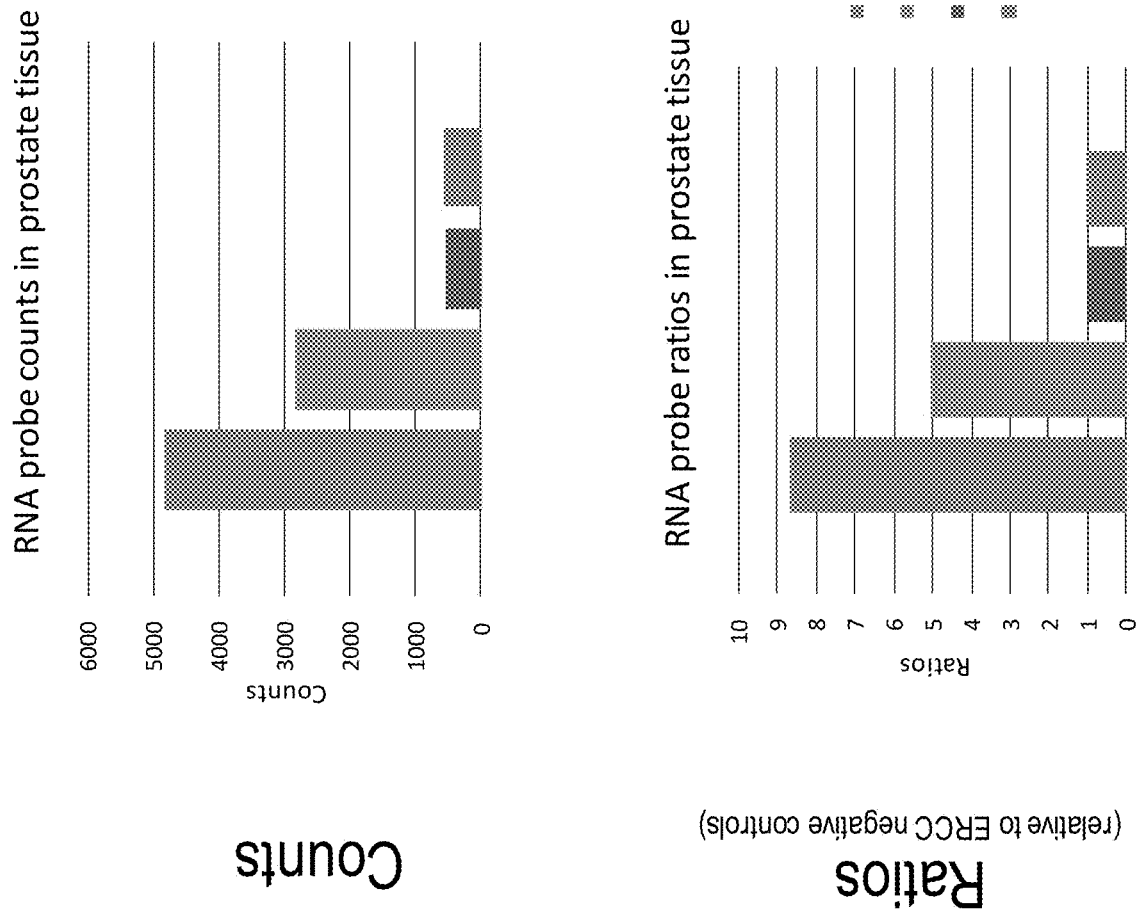
FIG. 57 shows RNA expression data from a probe specific to PSA (Prostate-Specific Antigen).

DNA probes (that recognize and bind to mRNA) were hybridized in situ, as described above, to RNA in 5 µm sections of FFPE prostate. A ten minute incubation in MES for at 97° C. was used instead of a one hour ethanol incubation. UV cleavage, signal oligonucleotide collection and detection, and signal-to-noise ratio calculations were performed as described in Example 17. Counts and ratios are shown in FIG. 57.

Example 20: Specificity of Probes Increase at Non-Standard, Sub-nM Concentrations Typically, in situ hybridization (ISH) probes that are used to recognize RNA are hybridized at 5 to 200 nM. Surprisingly, nucleic acid recognizing-probes of the present invention performed best at, or below, 0.2 nM, which is 25 to 1000-fold lower than standard ISH probe concentrations.

DNA probes were hybridized to RNA in situ, as described above, in 5 µm sections of FFPE HER2 3+ breast samples. Probes were used at 5, 1, 0.2, and 0.4 nM. UV cleavage, signal oligonucleotide collection and detection, and fold change calculation were performed as described in Example 17.

FIG. 58 shows that counts decreased with decreasing probe concentrations (top graph). However, unexpectedly, there was a significant gain in signal-to-noise when positive probe counts are compared to negative control probes, when probes are hybridized at sub-nM concentrations.

What is claimed is:

1. A method comprising:
   (1) contacting at least one nucleic acid target in a tissue sample with at least one probe comprising a target-binding domain, a signal oligonucleotide, and a photocleavable motif located between the target-binding domain and the signal oligonucleotide;
   (2) illuminating a specific location of the tissue sample with light sufficient to release the signal oligonucleotide;
   (3) collecting the released signal oligonucleotide by aspirating a solution proximal to the specific location that was illuminated, wherein the solution proximal to the specific location that was illuminated is located directly above the specific location that was illuminated, wherein the aspiration is performed using a capillary tube; and
   (4) identifying the released signal oligonucleotide, thereby detecting the at least one nucleic acid target in the specific location of the tissue sample that was illuminated.

2. The method of claim 1, wherein detecting comprises a polymerase reaction, a reverse transcriptase reaction, hybridization to an oligonucleotide microarray, mass spectrometry, hybridization to a fluorescent molecular beacon, a sequencing reaction, or molecular barcodes.

3. The method of claim 1, wherein detecting comprises determining the identity and the abundance of the at least one nucleic acid target.

4. The method of claim 1, wherein the at least one nucleic acid target comprises at least two distinct nucleic acid targets or at least two copies of the same nucleic acid target.

5. The method of claim 4, wherein detecting comprises comparing the abundance of each distinct nucleic acid target.

6. The method of claim 1, further comprising repeating at least steps (2)-(4) on at least a second specific location of the tissue sample.

7. The method of claim 6, wherein detecting comprises comparing the abundance of the at least one nucleic acid target in the specific location and in the at least second specific location.

8. The method of claim 6, wherein the specific location and the at least second specific location comprise the same cell type or distinct cell types.

9. The method of claim 1, wherein the tissue sample is directly immobilized to a surface or is indirectly immobilized to a surface.

10. The method of claim 1, wherein the tissue sample is a 2 to 1000 µm thick tissue section.

11. The method of claim 1, wherein the tissue section is obtained from a formalin-fixed paraffin embedded (FFPE) sample.

12. The method of claim 1, wherein the tissue sample is fixed or unfixed.

13. The method of claim 1, wherein the tissue sample is stained or labeled thereby allowing visualization of a sub-cellular, cellular, or tissue-related structure in the stained or labeled tissue sample.

14. The method of claim 1, wherein the signal oligonucleotide is a single-stranded nucleic acid or a partially double-stranded nucleic acid.

15. The method of claim 1, wherein a negative purification is used to remove intact probe molecules from the released signal oligonucleotides, wherein the negative purification comprises an affinity purification comprising contacting an intact probe with an immobilized oligonucleotide that is complementary to a portion of the intact probe or an immobilized antibody or protein-binding motif that recognizes and binds to a portion of the intact probe, wherein the intact probe's target binding domain comprises a universal purification tag or sequence that is partially complementary to the immobilized oligonucleotide or is capable of being recognized or bound by the immobilized antibody or protein-binding motif.

16. The method of claim 1, wherein the illumination is provided by a light source selected from the group consisting of an arc-lamp, a laser, a focused UV light source, and light emitting diode (LED).

17. The method of claim 1, wherein the light is UV light.

18. The method of claim 1, wherein the target-binding domain comprises a single-stranded nucleic acid or a partially double-stranded nucleic acid.

19. The method of claim 1, wherein the capillary tube comprises an optical device capable of transmitting light to the specific location of the tissue sample.

20. The method of claim 1, wherein the method further comprises illuminating a region of interest using a laser scanning device or a digital mirror device (DMD).

\* \* \* \* \*